United States Patent
Wu

(10) Patent No.: US 9,890,189 B2
(45) Date of Patent: *Feb. 13, 2018

(54) GEMCITABINE PRODRUGS AND USES THEREOF

(71) Applicant: BoYen Therapeutics, Inc., Taipei (TW)

(72) Inventor: Laurence I. Wu, Taipei (TW)

(73) Assignee: BoYen Therapeutics, Inc., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/369,187

(22) Filed: Dec. 5, 2016

(65) Prior Publication Data

US 2017/0107245 A1    Apr. 20, 2017

Related U.S. Application Data

(60) Continuation of application No. 14/599,166, filed on Jan. 16, 2015, now Pat. No. 9,540,410, which is a division of application No. 14/077,778, filed on Nov. 12, 2013, now Pat. No. 8,956,613.

(60) Provisional application No. 61/725,643, filed on Nov. 13, 2012.

(51) Int. Cl.
| | |
|---|---|
| A61K 39/395 | (2006.01) |
| C07H 19/06 | (2006.01) |
| A61K 31/7068 | (2006.01) |
| A61K 45/06 | (2006.01) |
| A61K 9/00 | (2006.01) |

(52) U.S. Cl.
CPC ........... *C07H 19/06* (2013.01); *A61K 9/0019* (2013.01); *A61K 9/0053* (2013.01); *A61K 31/7068* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,814,438 | A | 3/1989 | Armour et al. |
| 4,994,558 | A | 2/1991 | Armour et al. |
| 7,608,602 | B2 | 10/2009 | Gallop et al. |
| 8,956,613 | B2 | 2/2015 | Wu |
| 9,540,410 | B2 | 1/2017 | Wu |
| 2004/0142857 | A1 | 7/2004 | Gallop et al. |
| 2008/0021208 | A1 | 1/2008 | Gallop et al. |
| 2008/0103110 | A1 | 5/2008 | Klaveness et al. |
| 2009/0130214 | A1 | 5/2009 | Couvreur et al. |
| 2010/0016254 | A1 | 1/2010 | Gallop et al. |
| 2010/0160249 | A1 | 6/2010 | Couvreur et al. |
| 2011/0002991 | A1 | 1/2011 | Mickle et al. |
| 2012/0088908 | A1 | 4/2012 | Xue et al. |

FOREIGN PATENT DOCUMENTS

| | | |
|---|---|---|
| CN | 103130854 A | 6/2013 |
| EP | 0 986 570 B1 | 4/2003 |
| EP | 1 761 551 B1 | 8/2011 |
| WO | 98/32762 A1 | 7/1998 |
| WO | 01/021135 A2 | 3/2001 |
| WO | 01/021135 A3 | 3/2001 |
| WO | 2004/041203 A2 | 5/2004 |
| WO | 2004/041203 A3 | 5/2004 |
| WO | 2005/025552 A2 | 3/2005 |
| WO | 2005/025552 A3 | 3/2005 |

(Continued)

OTHER PUBLICATIONS

International Search Report corresponding to PCT/US2013/069640, dated Mar. 18, 2014, 10 pages.
CAS RN: 95058-81-4 (entered STN Mar. 3, 1985); see PTO-892 in parent U.S. Appl. No. 14/077,778.
International Preliminary Report on Patentability (Chapter II) corresponding to PCT/US2013/069640, dated Dec. 31, 2014, 25 pages.
Song et al., "Amino Acid Ester Prodrugs of the Anticancer Agent Gemcitabine: Synthesis, Bioconversion, Metabolic Bioevasion, and hPEPT1-Mediated Transport," Molecular Pharmaceutics, American Chemical Society, US, vol. 2, No. 2, Jan. 1, 2005, pp. 157-167, XP009168560.

(Continued)

*Primary Examiner* — Jared D Barsky
(74) *Attorney, Agent, or Firm* — Winston Hsu

(57) ABSTRACT

The present invention provides compounds according to formula I:

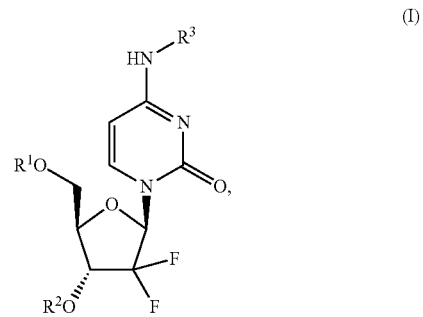

and pharmaceutically acceptable salts thereof. For compounds of formula I, $R^1$ and $R^2$ are independently selected from the group consisting of H, —C(=O)—(CH$_2$)$_2$-aryl, and —C(=O)—(CH$_2$)$_n$—C(=O)—NH-aryl. The subscript n is from 2 to 6. $R^3$ is selected from the group consisting of H and —C(=O)—O—$R^4$; and $R^4$ is selected from the group consisting of alkyl, substituted alkyl, alkenyl, substituted alkenyl, alkynyl, substituted alkynyl, arylalkyl, substituted arylalkyl, cycloheteroalkyl, substituted cycloheteroalkyl, heteroalkyl and substituted heteroalkyl. Compounds are provided wherein at least one of $R^1$ and $R^2$ is other than H. Pharmaceutical compositions, methods for inhibiting the growth of cancer cells, and methods for the treatment of cancer are also provided.

8 Claims, 1 Drawing Sheet

(56) References Cited

FOREIGN PATENT DOCUMENTS

| | | |
|---|---|---|
| WO | 2006/029081 A2 | 3/2006 |
| WO | 2006/029081 A3 | 3/2006 |
| WO | 2006/030217 A2 | 3/2006 |
| WO | 2006/030217 A3 | 3/2006 |
| WO | 2006/065525 A1 | 6/2006 |
| WO | 2006/090029 A1 | 8/2006 |
| WO | 2006/098628 A1 | 9/2006 |
| WO | 2007/009147 A2 | 1/2007 |
| WO | 2007/009147 A3 | 1/2007 |
| WO | 2007/149891 A2 | 12/2007 |
| WO | 2007/149891 A3 | 12/2007 |
| WO | 2008/080291 A1 | 7/2008 |
| WO | 2010/039039 A1 | 4/2010 |
| WO | 2010/042638 A2 | 4/2010 |
| WO | 2010/042638 A3 | 4/2010 |
| WO | 2010/121486 A1 | 10/2010 |
| WO | 2011/062503 A1 | 5/2011 |
| WO | 2012/045999 A1 | 4/2012 |
| WO | 2012/098557 A1 | 7/2012 |
| WO | 2013/019945 A2 | 2/2013 |
| WO | 2013/044811 A1 | 4/2013 |
| ZA | 98/0576 | 7/1998 |

OTHER PUBLICATIONS

European Patent Application No. 13855096.7, Extended European Search Report dated Mar. 3, 2016, 8 pages.
Singaporean Patent Application No. 11201503773S, Written Opinion dated Mar. 16, 2016, 5 pages.
*Singaporean Patent Application No. 11201503773S, Written Opinion dated Oct. 18, 2016, 4 pages.

GEMCITABINE PRODRUGS AND USES THEREOF

CROSS-REFERENCES TO RELATED APPLICATIONS

The application is a continuation of U.S. application Ser. No. 14/599,166, filed Jan. 16, 2015, allowed, which application is a divisional of U.S. application Ser. No. 14/077,778, filed Nov. 12, 2013, now U.S. Pat. No. 8,956,613, which claims the benefit of priority to U.S. Provisional Application Ser. No. 61/725,643, filed Nov. 13, 2012, each of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Gemcitabine is a nucleoside analogue that has been effectively used for the treatment of cancers including non-small cell lung cancer, pancreatic cancer, bladder cancer, ovarian cancer and breast cancer. Despite gemcitabine's demonstrated efficacy in a number of clinical situations, the drug is also associated with side effects such as flu-like symptoms, diarrhea, weakness, mouth sores, and shortness of breath. In order to maximize the benefits of gemcitabine-based chemotherapy regimens and improve safety and tolerability, new forms of gemcitabine are needed. The present invention, providing surprisingly effective gemcitabine derivatives, meets this and other needs.

BRIEF SUMMARY OF THE INVENTION

In one aspect, the invention provides compounds according to formula I:

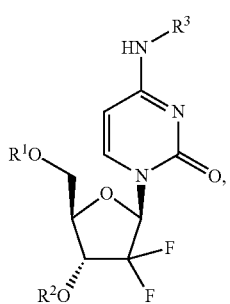

(I)

and pharmaceutically acceptable salts thereof. For compounds of formula I, $R^1$ and $R^2$ are independently selected from H, —C(=O)—(CH$_2$)$_2$-aryl, and —C(=O)—(CH$_2$)$_n$—C(=O)—NH-aryl, and at least one of $R^1$ and $R^2$ is other than H. The subscript n is from 2 to 6. $R^3$ is selected from H and —C(=O)—O—$R^4$; and $R^4$ is selected from alkyl, substituted alkyl, alkenyl, substituted alkenyl, alkynyl, substituted alkynyl, arylalkyl, substituted arylalkyl, cycloheteroalkyl, substituted cycloheteroalkyl, heteroalkyl and substituted heteroalkyl.

In a second aspect, the invention provides pharmaceutical compositions containing a pharmaceutically acceptable carrier and one or more compounds according to formula I as described above, prodrugs thereof, or pharmaceutically acceptable salts of the compounds and prodrugs.

In a third aspect, the invention provides methods for inhibiting the growth of cancer cells. The methods include contacting the cells with an effective amount of a compound of the invention.

In a fourth aspect, the invention provides methods for treating cancer. The methods include administering to the subject an effective amount of a pharmaceutical composition of the invention.

DETAILED DESCRIPTION OF THE INVENTION

I. Definitions

Figure 1:
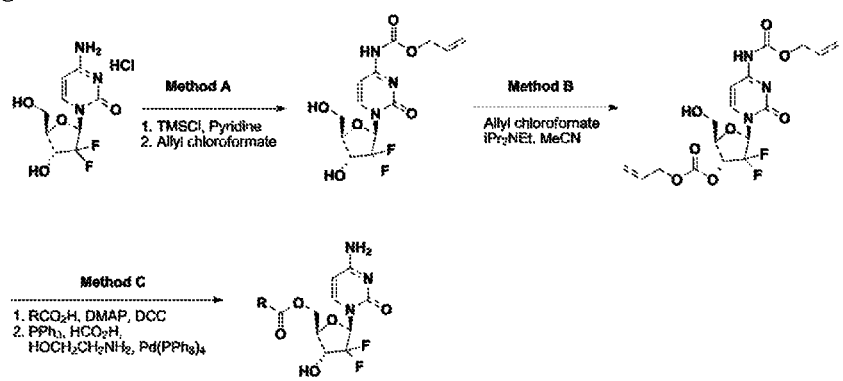
FIG. 1 shows a synthetic route for the preparation of 5'O-derivatized gemcitabine prodrugs.

As used herein, the term "prodrug" refers to a precursor compound that, following administration, releases a biologically active compound in vivo via a chemical or physiological process (e.g., a prodrug on reaching physiological pH or through enzyme action is converted to the biologically active compound). A prodrug itself may either lack or possess the desired biological activity.

As used herein, the term "salt" refers to an acid or base salt of a compound of the invention. Illustrative examples of pharmaceutically acceptable salts are mineral acid salts (prepared using hydrochloric acid, hydrobromic acid, phosphoric acid, and the like), organic acid salts (prepared using acetic acid, propionic acid, glutamic acid, citric acid, methanesulfonic acid, maleic acid, and the like), and quaternary ammonium salts (prepared using methyl iodide, ethyl iodide, and the like). It is understood that the pharmaceutically acceptable salts are non-toxic. Additional information on suitable pharmaceutically acceptable salts can be found in *Remington: The Science & Practice of Pharmacy*, 20th ed., Lippincott Williams & Wilkins, Philadelphia, Pa., 2000, which is incorporated herein by reference.

Salts of acidic compounds are formed with bases, namely cationic species such as alkali and alkaline earth metal cations (e.g., sodium, lithium, potassium, calcium, and magnesium ions), as well as ammonium cations (e.g., ammonium, trimethylammonium, diethylammonium, and tris-(hydroxymethyl)-methyl-ammonium ions). Salts of basic compounds are salts formed with mineral acids, organic carboxylic acids, organic sulfonic acids, and the like. The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. "Substituted aryl" groups can be substituted with one or more groups selected from halo, hydroxy, amino, alkylamino, amido, acyl, nitro, cyano, and alkoxy.

Aryl groups also include heteroaryl groups. "Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as in groups including, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrolyl, pyridinyl (2-, 3-, and 4-isomers), imidazolyl, pyrazolyl, triazolyl, tetrazolyl, pyrazinyl, pyrimidinyl, pyridazinyl, triazinyl (1,2,3-, 1,2,4- and 1,3,5-isomers), thiophenyl, furanyl, thiazolyl, isothiazolyl, oxazolyl, and isoxazolyl. The heteroaryl groups can also be fused to aromatic ring systems, such as a phenyl ring, to form members including, but not limited to, benzopyrroles such as indolyl and isoindolyl, benzopyridines such as quinolinyl and isoquinolinyl, benzopyrazinyl (quinoxaline), benzopyrimidinyl (quinazoline), benzopyridazines such as phthalazinyl and cinnolinyl, benzothiophenyl, and benzofuranyl. Other heteroaryl groups include heteroaryl rings linked by a bond, such as bipyridinyl. "Substituted heteroaryl" groups can be substituted with one or more groups selected from halo, hydroxy, amino, alkylamino, amido, acyl, nitro, cyano, and alkoxy.

As used herein, the term "alkyl" refers to a straight or branched, saturated, aliphatic radical having from 1 to about 10 carbon atoms. Alkyl can include any number of carbons, such as $C_{1-2}$, $C_{1-3}$, $C_{1-4}$, $C_{1-5}$, $C_{1-6}$, $C_{1-7}$, $C_{1-5}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms including, but not limited to, heptyl, octyl, nonyl, decyl, etc. "Substituted alkyl" groups can be substituted with one or more groups selected from halo, hydroxy, amino, alkylamino, amido, acyl, nitro, cyano, and alkoxy.

As used herein, the term "alkenyl" refers to a straight chain or branched hydrocarbon having at least 2 carbon atoms and at least one carbon-carbon double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. "Substituted alkenyl" groups can be substituted with one or more groups selected from halo, hydroxy, amino, alkylamino, amido, acyl, nitro, cyano, and alkoxy.

As used herein, the term "alkynyl" refers to either a straight chain or branched hydrocarbon having at least 2 carbon atoms and at least one carbon-carbon triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. "Substituted alkynyl" groups can be substituted with one or more groups selected from halo, hydroxy, amino, alkylamino, amido, acyl, nitro, cyano, and alkoxy.

As used herein, the term "arylalkyl" refers to a radical having an alkyl component and an aryl component, where the alkyl component links the aryl component to the point of attachment. The alkyl component is as defined above, except that the alkyl component is at least divalent (i.e., an alkylene), to link to the aryl component to the point of attachment. The alkyl component can include any number of carbons, such as $C_{1-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Examples of arylalkyl groups include, but are not limited to, benzyl and ethylbenzene. "Substituted arylalkyl" groups can be substituted with one or more groups selected from halo, hydroxy, amino, alkylamino, amido, acyl, nitro, cyano, and alkoxy.

As used herein, the term "cycloheteroalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as is groups including, but not limited to, —S(O)— and —S(O)$_2$—. Cycloheteroalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the cycloheteroalkyl groups, such as 1, 2, 3, or 4, or 1 to 2, 1 to 3, 1 to 4, 2 to 3, 2 to 4, or 3 to 4. The cycloheteroalkyl group can include groups such as aziridinyl, azetidinyl, pyrrolidinyl, piperidinyl, azepanyl, azocanyl, quinuclidinyl, pyrazolidinyl, imidazolidinyl, piperazinyl (1,2-, 1,3- and 1,4-isomers), oxiranyl, oxetanyl, tetrahydrofuranyl, oxanyl (tetrahydropyranyl), oxepanyl, thiiranyl, thietanyl, thiolanyl (tetrahydrothiophenyl), thianyl (tetrahydrothiopyranyl), oxazolidinyl, isoxalidinyl, thiazolidinyl, isothiazolidinyl, dioxolanyl, dithiolanyl, morpholino, thiomorpholino, dioxanyl, or dithianyl. The cycloheteroalkyl groups can also be fused to aromatic or non-aromatic ring systems to form members including, but not limited to, indolinyl. Cycloheteroalkyl groups can be unsubstituted or substituted. "Substituted cycloheteroalkyl" groups can be substituted with one or more groups selected from halo, hydroxy, amino, alkylamino, amido, acyl, nitro, cyano, alkoxy, and oxo.

As used herein, the term "heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as in groups including, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms. "Substituted heteroalkyl" groups can be substituted with one or more groups selected from halo, hydroxy, amino, alkylamino, amido, acyl, nitro, cyano, and alkoxy.

As used herein, the term "alkoxy" refers to an alkyl group, as defined herein, having an oxygen atom that connects the alkyl group to the point of attachment (i.e., alkyl-O—). Alkoxy groups can have any suitable number of carbon atoms, such as $C_{1-6}$. Alkoxy groups include, for example, methoxy, ethoxy, propoxy, isopropoxy, butoxy, 2-butoxy, isobutoxy, sec-butoxy, tert-butoxy, pentoxy, hexoxy, etc.

As used herein, the term "acyl," by itself or as part of another substituent, refers to a radical containing an alkyl group, as defined herein, bound to the carbon atom of a carbonyl group, the carbonyl carbon atom further being the point of attachment of the radical.

As used herein, the term "amino," by itself or as a part of another substituent, refers to a radical containing a nitrogen atom bound to two or three atoms selected from hydrogen and carbon, the nitrogen atom further being the point of attachment of the radical.

As used herein, the term "amido," by itself or as part of another substituent, refers to a radical containing an acyl group, as defined herein, bound to the nitrogen atom of an amino group, the carbonyl carbon atom or the nitrogen atom further being the point of attachment of the radical.

As used herein, the term "composition" is intended to encompass a product comprising the specified ingredients in the specified amounts, as well as any product, which results, directly or indirectly, from combination of the specified ingredients in the specified amounts. By "pharmaceutically acceptable" it is meant the carriers, diluents or excipients in the composition must be compatible with other ingredients and not deleterious to the recipient thereof.

As used herein, the term "pharmaceutically acceptable carrier" refers to a substance that aids the administration of an active agent to and absorption by a subject. Pharmaceutical carriers useful in the present invention include, but are not limited to, binders, fillers, disintegrants, lubricants, coatings, sweeteners, flavors and colors. One of skill in the art will recognize that other pharmaceutical carriers are useful in the present invention.

As used herein, the terms "treat", "treating" and "treatment" refer to any indicia of success in the treatment or amelioration of cancer or an injury, pathology, condition, or symptom (e.g., pain) related to cancer, including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "cancer" refers to conditions including solid cancers, lymphomas, and leukemias. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma, head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the term "administering" refers to oral, topical, parenteral, intraperitoneal, intramuscular, intralesional, intranasal, subcutaneous, or intrathecal administration of a compound or composition of the invention to a subject, as well as administration via suppository or implantation of a slow-release device, e.g., a mini-osmotic pump.

As used herein, the term "effective amount" refers to a dose of a compound or composition that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

II. Gemcitabine Prodrugs

In one aspect, the invention provides compounds according to formula I:

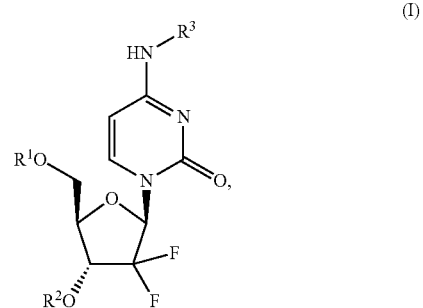

and pharmaceutically acceptable salts thereof. For compounds of formula I, $R^1$ and $R^2$ are independently selected from H, —C(=O)—(CH$_2$)$_2$—Ar and —C(=O)—(CH$_2$)$_n$—C(=O)—NH—Ar, wherein Ar is aryl or heteroaryl and at least one of $R^1$ and $R^2$ is other than H. The subscript n is from 2 to 6. $R^3$ is selected from H and —C(=O)—O—$R^4$; and $R^4$ is selected from alkyl, substituted alkyl, alkenyl, substituted alkenyl, alkynyl, substituted alkynyl, arylalkyl, substituted arylalkyl, cycloheteroalkyl, substituted cycloheteroalkyl, heteroalkyl and substituted heteroalkyl. In some embodiments, the invention provides prodrugs of compounds of formula I and pharmaceutically acceptable salts of the prodrugs.

In some embodiments, $R^1$ and $R^2$ are independently selected from H, —C(=O)—(CH$_2$)$_2$—Ar and —C(=O)—(CH$_2$)$_n$—C(=O)—NH-phenyl, wherein Ar is phenyl or 3-pyridyl; and the subscript n is 2, 4 or 6. In some embodiments, $R^2$ and $R^3$ are H. In some embodiments, $R^2$ is H and $R^1$ and $R^3$ are other than H. In some embodiments, $R^1$ is H and $R^2$ and $R^3$ are other than H. In some embodiments, $R^4$ is selected from alkyl and substituted alkyl when $R^3$ is other than H. In some embodiments, $R^4$ is $C_1$-$C_8$ alkyl when $R^3$ is other than H. In some embodiments, $R^4$ is $C_3$-$C_8$ heteroalkyl when $R^3$ is other than H.

In some embodiments, $R^2$ is H and $R^3$ is $C_{1-8}$ alkyloxycarbonyl or $C_{3-8}$ heteroalkyloxycarbonyl. In such embodiments, $R^1$ can be aryl-acyl, heteroaryl-acyl, arylamido-acyl, or heteroarylamido-acyl. In some embodiments, $R^1$ is selected from (3-aryl)propanoyl, (3-heteroaryl)propanoyl, 4-arylamino-4-oxo-butanoyl, 6-arylamino-6-oxo-hexanoyl, 8-arylamino-8-oxo-octanoyl, 4-heteroarylamino-4-oxo-butanoyl, 6-heteroarylamino-6-oxo-hexanoyl, and 8-heteroarylamino-8-oxo-octanoyl.

In some embodiments, $R^2$ is H and $R^3$ is alkyloxycarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^2$ is H and $R^3$ is ethoxycarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^2$ is H and $R^3$ is n-butyloxycarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^2$ is H and $R^3$ is isobutyloxycarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^2$ is H and $R^3$ is n-pentyloxycarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^2$ is H and $R^3$ is n-hexyloxycarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^2$ is H and $R^3$ is n-heptyloxycarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^2$ is H and $R^3$ is $C_{3-8}$ heteroalkylcarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^2$ is H and $R^3$ is (2-methoxy)ethyloxycarbonyl. In such embodiments, $R^1$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is $C_{1-8}$ alkyloxycarbonyl or $C_{3-8}$ heteroalkyloxycarbonyl. In such embodiments, $R^2$ can be aryl-acyl, heteroaryl-acyl, arylamido-acyl, or heteroarylamido-acyl. In some embodiments, $R^2$ is selected from (3-aryl)propanoyl, (3-heteroaryl)propanoyl, 4-arylamino-4-oxo-butanoyl, 6-arylamino-6-oxo-hexanoyl, 8-arylamino-8-oxo-octanoyl, 4-heteroarylamino-4-oxo-butanoyl, 6-heteroarylamino-6-oxo-hexanoyl, and 8-heteroarylamino-8-oxo-octanoyl.

In some embodiments, $R^1$ is H and $R^3$ is $C_{1-8}$ alkyloxycarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is ethoxycarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is n-butyloxycarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is isobutyloxycarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is n-pentyloxycarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is n-hexyloxycarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is n-heptyloxycarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is $C_{3-8}$ heteroalkylcarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

In some embodiments, $R^1$ is H and $R^3$ is (2-methoxy)ethyloxycarbonyl. In such embodiments, $R^2$ can be 3-phenyl-propanoyl, 3-(3-pyridyl)-propanoyl, 4-anilino-4-oxo-butanoyl, 6-anilino-6-oxo-hexanoyl, or 8-anilino-8-oxo-octanoyl.

Figure 2:
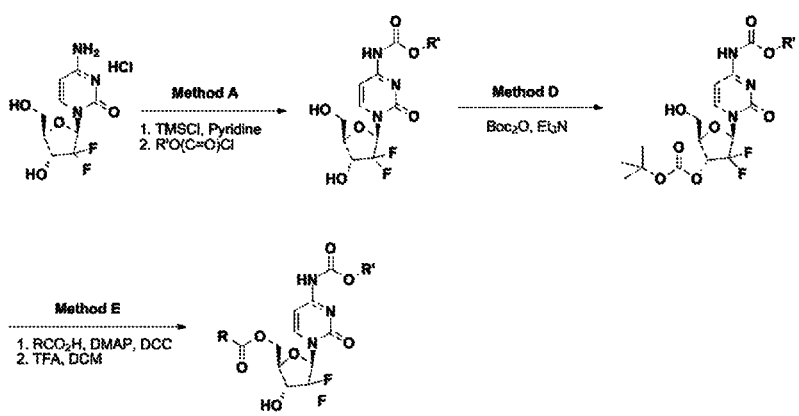
FIG. 2 shows a synthetic route for the preparation of N4-5'O-derivatized gemcitabine prodrugs.
Figure 3:
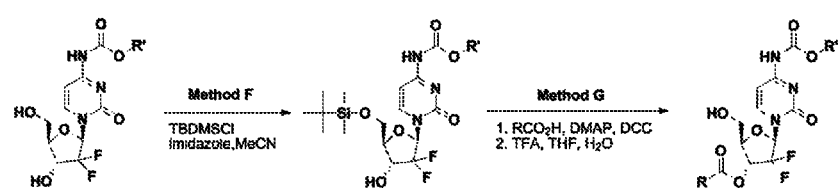
FIG. 3 shows a synthetic route for the preparation of 3'O—N4-derivatized gemcitabine prodrugs.

Compounds of the invention can be made by the methods depicted in FIGS. 1, 2, and 3. These schemes are merely illustrative of some methods by which the compounds of the invention can be synthesized, and various modifications to these schemes can be made and will be suggested to one skilled in the art having referred to this disclosure.

The starting materials and reagents used in preparing these compounds are either available from commercial suppliers or are prepared by methods known to those skilled in the art following procedures set forth in references such as Fieser and Fieser's *Reagents for Organic Synthesis*, Volumes 1-17 (John Wiley and Sons, 1991); Rodd's *Chemistry of Carbon Compounds*, Volumes 1-5 and Supplementals (Elsevier Science Publishers, 1989); *Organic Reactions*, Volumes 1-40 (John Wiley and Sons, 1991); March's *Advanced Organic Chemistry*, (John Wiley and Sons, 4th Edition) and Larock's *Comprehensive Organic Transformations* (VCH Publishers Inc., 1989).

The starting materials and the intermediates of the reaction can be isolated and purified if desired using conventional techniques including, but not limited to, filtration, distillation, crystallization, chromatography and the like. Such materials can be characterized using conventional means, including measuring physical constants and obtaining spectral data.

Unless specified to the contrary, the reactions described herein take place at atmospheric pressure over a temperature range of from about −78° C. to about 150° C. For example, reactions can be conducted at from about 0° C. to about 125° C., or at about room (or ambient) temperature, e.g., about 20° C.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups can be used in accordance with standard practice, for examples see T. W. Greene and P. G. M. Wuts in "*Protective Groups in Organic Chemistry*" John Wiley and Sons, 1999.

III. Pharmaceutical Compositions

In a second aspect, the invention provides pharmaceutical compositions containing one or more compounds according to formula I as described above, prodrugs thereof, or pharmaceutically acceptable salts of the compounds and prodrugs.

Accordingly, some embodiments of the invention provide pharmaceutical compositions containing any of the compounds of formula I described herein, or pharmaceutical salts thereof, as well as a pharmaceutically acceptable carrier. The compositions can also include prodrugs of compounds of formula I, or pharmaceutically acceptable salts of the prodrugs. For compositions containing compounds of formula (I), $R^1$ and $R^2$ are independently selected from H, —C(O)—$(CH_2)_2$—Ar and —C(=O)—$(CH_2)_n$—C(=O)—NH—Ar, wherein Ar is aryl or heteroaryl and at least one of $R^1$ and $R^2$ is other than H. The subscript n is from 2 to 6. $R^3$ is selected from H and —C(=O)—O—$R^4$; and $R^4$ is selected from alkyl, substituted alkyl, alkenyl, substituted alkenyl, alkynyl, substituted alkynyl, arylalkyl, substituted arylalkyl, cycloheteroalkyl, substituted cycloheteroalkyl, heteroalkyl and substituted heteroalkyl.

In some embodiments, $R^1$ and $R^2$ are independently selected from H, —C(=O)—$(CH_2)_2$—Ar and —C(=O)—$(CH_2)_n$—C(=O)—NH-phenyl, wherein Ar is phenyl or 3-pyridyl; and the subscript n is 2, 4 or 6. In some embodiments, $R^2$ and $R^3$ are H. In some embodiments, $R^2$ is H and $R^1$ and $R^3$ are other than H. In some embodiments, $R^1$ is H and $R^2$ and $R^3$ is other than H. In some embodiments, $R^4$ is selected from alkyl and substituted alkyl when $R^3$ is other than H.

The pharmaceutical compositions for the administration of the compounds of the invention can be prepared by any of the methods well known in the art of pharmacy and drug delivery. The compositions can be conveniently prepared and/or packaged in unit dosage form. Methods of preparing the compositions include the step of bringing the active ingredient into association with a carrier containing one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation.

The pharmaceutical compositions can be in the form of a sterile injectable aqueous or oleaginous suspension. This suspension can be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active materials in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, can also be present.

The pharmaceutical compositions of the invention may also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions containing the active ingredient can be in a form suitable for oral use, for example, as tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powder and effervescent tablets. Compositions intended for oral use can be prepared according to any method known to the art for the manufacture of pharmaceutical compositions and such compositions may contain one or more agents selected from sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients include, but are not limited to: inert diluents such as cellulose, silicon dioxide, aluminum oxide, calcium carbonate, sodium carbonate, glucose, mannitol, sorbitol, lactose, calcium phosphate and sodium phosphate; granulating and disintegrating agents such as corn starch and alginic acid; binding agents such as PVP, cellulose, PEG, starch, gelatin and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil). Additionally, emulsions can be prepared with a non-water miscible ingredients such as oils and stabilized with surfactants such as mono-diglycerides, PEG esters, and the like.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles, as well as eye-drops for opthalmological use.

The compounds of the invention can be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique. The term "deposited" means that the inhibitory agent is coated, adsorbed, placed, or otherwise incorporated into the device by methods known in the art. For example, the inhibitory agent can be embedded and released from within ("matrix type") or surrounded by and released through ("reservoir type") polymer materials that coat or span the medical device. In the later example, the inhibitory agent can be entrapped within the polymer materials or coupled to the polymer materials using one or more the techniques for generating such materials known in the art. In other formulations, the inhibitory agent can be linked to the surface of the medical device without the need for a coating by means of detachable bonds and release with time, can be removed by active mechanical or chemical processes, or are in a permanently immobilized form that presents the inhibitory agent at the implantation site.

IV. Methods of Inhibiting Cancer

In a third aspect, the invention provides methods for treating cancer in a subject. The methods include administering to the subject an effective amount of a compound or pharmaceutical composition of the invention. In therapeutic use for the treatment of cancer, the compounds and compositions of the present invention can be administered such that the initial dosage of a gemcitabine prodrug ranges from about 0.001 mg/kg to about 1000 mg/kg daily. A daily dose of about 0.01-500 mg/kg, or about 0.1-200 mg/kg, or about 1-100 mg/kg, or about 10-50 mg/kg, or about 10 mg/kg, or about 5 mg/kg, or about 2.5 mg/kg, or about 1 mg/kg can be used.

The dosages can be varied depending upon the requirements of the patient, the severity of the cancer being treated, and the gemcitabine prodrug being employed. For example, dosages can be empirically determined considering the type and stage of cancer diagnosed in a particular patient. The dose administered to a patient should be sufficient to result in a beneficial therapeutic response in the patient over time. The size of the dose will also be determined by the existence, nature, and extent of any adverse side-effects that accompany the administration of a particular gemcitabine prodrug in a particular patient. Determination of the proper dosage for a particular situation is within the skill of the typical practitioner. Generally, treatment is initiated with smaller dosages which are less than the optimum dose of the gemcitabine prodrug. Thereafter, the dosage is increased by small increments until the optimum effect under the circumstances is reached. The total daily dosage can be divided and administered in portions during the day.

The compositions can be administered alone in the methods of the invention, or in combination with other therapeutic agents. In some embodiments, the methods further include administering to the subject an anti-cancer agent. In certain instances, the methods include a combination of anti-cancer agents. Any suitable anti-cancer agent can be used in the methods of the invention. In some embodiments, the anti-cancer agent is selected from a conventional chemotherapeutic agent, a targeted therapeutic agent, and a radiotherapeutic agent.

Suitable conventional chemotherapeutic agents include, but are not limited to, anthracycline antibiotics, DNA synthesis inhibitors, alkylating agents, antifolate agents, metabolic inhibitors and combinations thereof. Examples of anthracycline antibiotics include, but are not limited to, doxorubicin, epirubicin, mitoxantrone and the like. Examples of DNA synthesis inhibitors include, but are not limited to, mitomycin C, 5FU (5-fluorouracil), capecitabine, irinotecan hydrochloride, thymitaq and the like. Examples of alkylating agents include, but are not limited to, cisplatin, carboplatin, oxaliplatin, mitoxantrone and the like. Examples of metabolic inhibitors include, but are not limited to, etoposide, rottlerin and the like. Examples of antifolate agents include, but are not limited to, nolatrexed and the like.

Targeted cancer therapies are medications which inhibit the growth of cancer cells by interfering with specific targeted molecules needed for carcinogenesis and cancer growth, rather than by simply interfering with rapidly dividing cells (e.g. with conventional chemotherapeutic agent). Targeted cancer therapy can include kinase inhibitors, angiogenesis inhibitors, epidermal growth factor receptor (EGFR)

inhibitors, HER2/neu receptors, or combinations thereof. Examples of kinase inhibitors include, but are not limited to, lapatinib, sorefenib, sunitinib, erotinib, ABT-869, ARQ 197 and the like. Examples of angiogenesis inhibitors include, but are not limited to, Avastin, Brivanib, Bevacizumab, Ramucirumab and the like. Examples of EGFR inhibitor include, but are not limited to, Cetuximab, Gefitinib and the like. Examples of HER2/neu receptor include, but are not limited to, Trastuzumab and the like.

Radiotherapeutic agents are those conventionally adopted in the therapeutic field of cancer treatment and include photons having enough energy for chemical bond ionization such as, for instance, alpha (α), beta (β), and gamma (γ) rays from radioactive nuclei as well as x-rays. The radiation may be high-LET (linear energy transfer) or low-LET. LET is the energy transferred per unit length of the distance. High LET is said to be densely ionizing radiation and Low LET is said to be sparsely ionizing radiation. Representative examples of high-LET are neutrons and alpha particles. Representative examples of low-LET are x-ray and gamma rays. Low LET radiation including both x-rays and γ rays is most commonly used for radiotherapy of cancer patients. The radiation may be used for external radiation therapy that is usually given on an outpatient basis or for internal radiation therapy that uses radiation that is placed very close to or inside the tumor. In case of internal radiation therapy, the radiation source is usually sealed in a small holder called an implant. Implants may be in the form of thin wires, plastic tubes called catheters, ribbons, capsules, or seeds. The implant is put directly into the body. Internal radiation therapy may require a hospital stay. The ionizing radiation source is provided as a unit dose of radiation and is preferably an x-ray tube since it provides many advantages, such as convenient adjustable dosing where the source may be easily turned on and off, minimal disposal problems, and the like. A unit dose of radiation is generally measured in gray (Gy). The ionizing radiation source may also comprise a radioisotope, such as a solid radioisotopic source (e.g., wire, strip, pellet, seed, bead, or the like), or a liquid radioisotopic filled balloon. In the latter case, the balloon has been specially configured to prevent leakage of the radioisotopic material from the balloon into the body lumen or blood stream. Still further, the ionizing radiation source may comprise a receptacle in the catheter body for receiving radioisotopic materials like pellets or liquids. The radioisotopic material may be selected to emit α, β and γ. Usually, α and β radiations are preferred since they may be quickly absorbed by the surrounding tissue and will not penetrate substantially beyond the wall of the body lumen being treated. Accordingly, incidental irradiation of the heart and other organs adjacent to the treatment region can be substantially eliminated. The total number of units provided will be an amount determined to be therapeutically effective by one skilled in treatment using ionizing radiation. This amount will vary with the subject and the type of malignancy or neoplasm being treated. The amount may vary but a patient may receive a dosage of about 30-75 Gy over several weeks.

Additional anti-cancer agents can include, but are not limited to, 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride. In some embodiments, the anticancer agent is selected from methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel. In some embodiments, the anticancer agent is selected from cisplatin, oxaliplatin, carboplatin, erlotinib, gefitinib, lapatinib, cetuximab, zalutumumab, minotuzumab, and matuzumab.

Compounds and compositions as described above can be administered via any suitable route when used in the methods of the invention. In some embodiments, administering the compound or composition is conducted orally. In some embodiments, administering the compound or composition is conducted parenterally. Other routes of administration can be useful in the methods of the invention.

A number of cancers can be treated according to the methods of the invention. Cancers contemplated for treatment using the methods of the invention include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, non-small cell lung cancer, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. Cancers also include blood-borne cancers, such as acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, and multiple myeloma. Cancer also includes acute and chronic leukemias such as lymphoblastic, myelogenous, lymphocytic, and myelocytic leukemias. Cancer also includes lymphomas such as Hodgkin's disease, non-Hodgkin's Lymphoma, Waldenström's macroglobulinemia, heavy chain disease, and polycythemia vera. Some embodiments of the invention provide methods for treating cancer as described above, wherein the cancer is selected from pancreatic cancer, non-small cell lung cancer, breast cancer, ovarian cancer, and bladder cancer.

In a related aspect, the invention provides methods for inhibiting the growth of cancer cells. The methods include contacting the cells with an effective amount of any of the compounds of the invention. In some embodiments, the methods further include contacting the cells with an anti-cancer agent. In some embodiments, the anti-cancer agent is selected from a conventional chemotherapeutic agent, a targeted therapeutic agent, a radiotherapeutic agent, and a mixture thereof. In some embodiments, the anti-cancer agent is selected from cisplatin, oxaliplatin, carboplatin, erlotinib, gefitinib, lapatinib, cetuximab, zalutumumab, minotuzumab, and matuzumab. In some embodiments, the cancer cells are selected from the group consisting of pancreatic cancer cells, non-small cell lung cancer cells, breast cancer cells, ovarian cancer cells, and bladder cancer cells.

V. Examples

Example 1

5'O-derivatized gemcitabine prodrugs can be prepared according to FIG. 1.

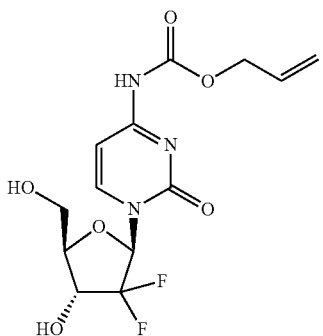

Method A: Preparation of 4-Allyloxycarbonylamino-1-[(2R,4R,5R)-3,3-difluoro-4-hydroxy-5-(hydroxymethyl)oxolan-2-yl]-1,2-dihydropyrimidin-2-one (1)

To a solution of gemcitabine hydrochloride (1.2 g, 4 mmol) in 12 mL pyridine, chlorotrimethylsilane (2.54 mL, 20 mmol) was added at 0° C.; after stirring for 2 h, allyl chloroformate (0.43 mL, 4 mmol) was added at 0° C. The reaction mixture was allowed to warm to RT, and heated at 45° C. overnight, then cooled to 30-35° C. when 12 mL of absolute EtOH was added. The reaction mixture was reheated at 45° C. for 0.5 h, and following the addition of 6 mL of H$_2$O, was heated at 45° C. for 5 h, then cooled to RT and concentrated in vacuo. The residue was partitioned between EtOAc and water; The organic layer was separated, and the aqueous layer was again extracted with EtOAc. The organic extracts were combined and washed with saturated aqueous CuSO$_4$ solution, saturated aqueous NaHCO$_3$ solution and brine, dried over Na$_2$SO$_4$ and concentrated in vacuo. Purification by flash column chromatography (5:1→10:1 EtOAc/Hexane) afforded 1 (white solid, 70% yield): $^1$H NMR (400 MHz, DMSO-d$_6$) δ11.00 (s, 1H), 8.26-8.28 (d, 1H), 7.13-7.15 (d, 1H), 6.34-6.37 (d, 1H), 6.18-6.22 (t, 1H), 5.95-6.02 (m, 1H), 5.38-5.43 (d, 1H), 5.34 (t, 1H), 5.27-5.30 (d, 1H), 4.67-4.69 (d, 2H), 4.20-4.25 (m, 1H), 3.90-3.95 (m, 1H), 3.82-3.86 (m, 1H), 3.66-3.72 (m, 1H); MS (HR-ESI): m/z 346.0857 [M−H]$^-$.

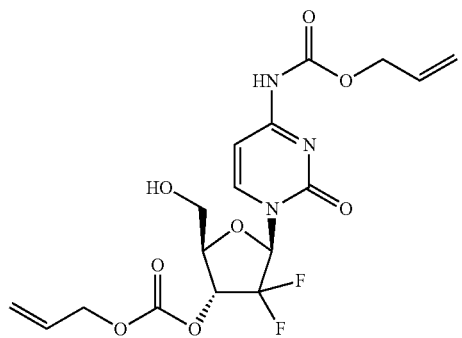

Method B: Preparation of 4-Allyloxycarbonylamino-1-[(2R,4R,5R)-4-allyloxycarbonyloxy-3,3-difluoro-5-(hydroxymethyl)oxolan-2-yl]-1,2-dihydropyrimidin-2-one (2)

Allyl chloroformate (0.23 mL, 2.2 mmol) was added to a solution of 1 (694 mg, 2 mmol), N,N-diisopropylethylamine (0.7 mL, 4 mmol) in 20 mL MeCN at 0° C. The reaction mixture was stirred at 0° C. for 4 h and concentrated in vacuo. The crude residue was purified by flash column chromatography (2:1→4:1 EtOAc/Hexane) to give 2 (white solid, 65% yield): $^1$H NMR (400 MHz, DMSO-d$_6$) δ11.05 (s, 1H), 8.19-8.22 (d, 1H), 7.16-7.18 (d, 1H), 6.32-6.37 (t, 1H), 5.93-6.05 (m, 2H), 5.43 (s, 1H), 5.27-5.39 (m, 5H), 4.74-4.75 (d, 2H), 4.67-4.69 (d, 2H), 4.31-4.33 (m, 1H), 3.82-3.84 (m, 1H), 3.73-3.76 (m, 1H).

Method C: Preparation of 4-Amino-1-[(2R,4R,5R)-3,3-difluoro-4-hydroxy-5-(3-phenylpropanoyloxymethyl)oxolan-2-yl]-1,2-dihydropyrimidin-2-one (3)

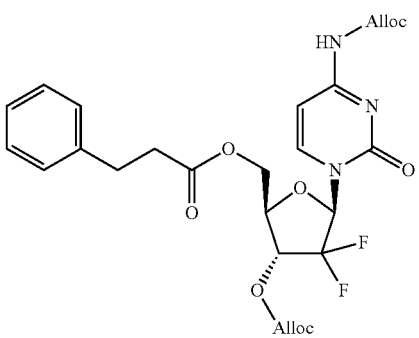

Preparation of 4-Allyloxycarbonylamino-1-[(2R,4R,5R)-4-allyloxycarbonyloxy-3,3-difluoro-5-(3-phenylpropanoyloxymethyl)oxolan-2-yl]-1,2-dihydropyrimidin-2-one (3a)

A solution of 2 (150 mg, 0.35 mmol), 3-phenylpropanoic acid (57 mg, 0.38 mmol), 4-dimethylaminopyridine (8 mg, 0.07 mmol) in 4 mL dimethoxyethane, N,N'-dicyclohexylcarbodiimide (158 mg, 0.77 mmol) was added at 0° C., the reaction mixture was stirred overnight at RT, and after filtering off the resulting precipitates was then concentrated in vacuo. Purification by flash column chromatography (1:2→1:1 EtOAc/Hexane) provided 3a (colorless oil, 51% yield): $^1$H NMR (400 MHz, DMSO-$d_6$) δ11.05 (s, 1H), 8.06-8.08 (d, 1H), 7.16-7.33 (m, 6H), 6.35 (t, 1H), 5.95-6.02 (m, 2H), 5.43-5.44 (dd, 2H), 5.38-5.40 (dd, 1H), 5.27-5.33 (t, 2H), 4.73-4.74 (d, 2H), 4.68-4.70 (d, 2H), 4.47-4.51 (d, 2H), 4.43-4.45 (m, 1H), 2.87-2.92 (t, 2H), 2.70-2.75 (t, 2H).

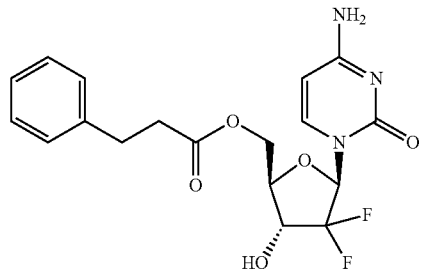

Preparation of 4-Amino-1-[(2R,4R,5R)-3,3-difluoro-4-hydroxy-5-(3-phenylpropanoyloxymethyl)oxolan-2-yl]-1,2-dihydropyrimidin-2-one (3)

A solution of 3a (100 mg, 0.18 mmol), triphenylphosphine (19 mg, 0.07 mmol), ethanolamine (0.02 mL, 0.36 mmol) and formic acid (0.03 mL, 0.67 mmol) in 5 mL of 2:2:1 THF/MeCN/H$_2$O was degassed by bubbling under N$_2$ for 1 min, palladium tetrakis(triphenylphosphine) (41 mg, 0.04 mmol) was added; Then the resulting reaction mixture was stirred 1 h at RT, concentrated in vacuo, extracted with EtOAc. The organic extracts were washed with brine, dried over Na$_2$SO$_4$, concentrated, then purified by flash column chromatography (1:1 Acetone/CH$_2$Cl$_2$) afforded 3 (colorless solid, 33% yield): $^1$H NMR (400 MHz, DMSO-$d_6$) δ7.52-7.55 (d, 1H), 7.42-7.45 (d, 2H), 7.22-7.31 (m, 5H), 6.41-6.44 (d, 1H), 6.19-6.23 (t, 1H), 5.80-5.84 (d, 1H), 4.34-4.43 (m, 1H), 4.29-4.33 (m, 1H), 4.22 (s, 1H), 3.99-4.05 (m, 1H), 2.89-2.91 (t, 2H), 2.72-2.75 (t, 2H); MS (HR-ESI): m/z 396.1373 [M+H]$^+$.

Example 2

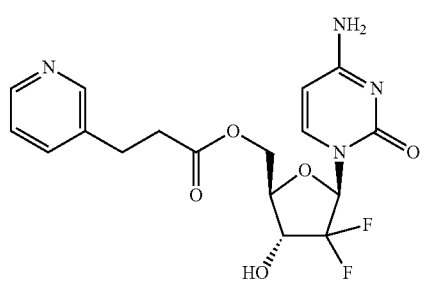

Preparation of 4-Amino-1-[(2R,4R,5R)-3,3-difluoro-4-hydroxy-5-(3-(3-pyridyl)propanoyloxymethyl)oxolan-2-yl]-1,2-dihydropyrimidin-2-one (4)

Using Method C and 3-(3-pyridyl)propanoic acid, 2 was converted to 4 (white solid, 53% yield): $^1$H NMR (400 MHz, DMSO-$d_6$) δ8.51 (s, 1H), 8.43-8.44 (d, 1H), 7.69-7.71 (d, 1H), 7.53-7.55 (d, 1H), 7.45-7.47 (d, 2H), 7.31-7.34 (m, 1H), 6.46 (s, 1H), 6.20 (s, 1H), 5.82-5.84 (d, 1H), 4.39-4.42 (d, 1H), 4.30-4.34 (m, 1H), 4.21 (m, 1H), 4.00-4.03 (t, 1H), 2.90-2.93 (t, 2H), 2.76-2.80 (t, 2H).

Example 3

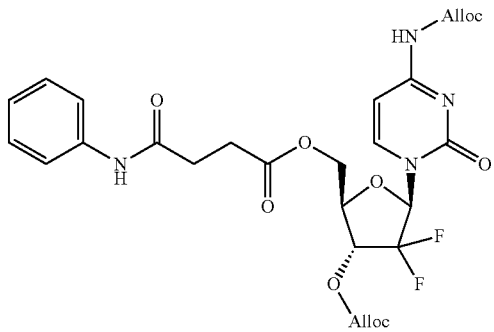

Preparation of 4-Allyloxycarbonylamino-1-[(2R,4R,5R)-4-allyloxycarbonyloxy-5-((4-anilino-4-oxobutanoyloxy)methyl)-3,3-difluoro-oxolan-2-yl]-1,2-dihydropyrimidin-2-one (5a)

Using Method C and 4-anilino-4-oxo-butanoic acid, 2 was converted to 5a (colorless oil, 84% yield): $^1$H NMR (400 MHz, DMSO-$d_6$) δ11.06 (s, 1H), 10.02 (s, 1H), 8.09-8.11 (d, 1H), 7.59-7.61 (d, 2H), 7.28-7.32 (t, 2H), 7.04 (t, 1H), 5.96-6.00 (m, 4H), 5.30-5.43 (m, 5H), 4.73-4.75 (m, 2H), 4.67-4.69 (d, 2H), 4.54 (s, 2H), 4.40-4.42 (m, 1H), 2.69 (s, 4H).

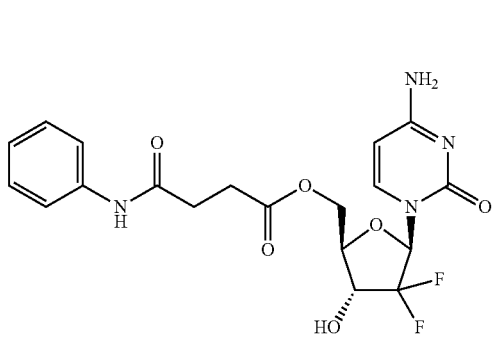

Preparation of 4-Amino-1-[(2R,4R,5R)-5-((4-anilino-4-oxo-butanoyloxy)methyl)-3,3-difluoro-4-hydroxy-oxolan-2-yl]-1,2-dihydropyrimidin-2-one (5)

Using Method C, 5a was converted to 5 (yellow solid, 10% yield): $^1$H NMR (400 MHz, DMSO-d$_6$) δ10.02 (s, 1H), 7.48-7.53 (t, 3H), 7.42-7.45 (d, 2H), 7.29-7.37 (t, 2H), 7.03-7.08 (t, 1H), 6.42-6.45 (d, 1H), 6.20-6.23 (t, 1H), 5.80-5.85 (d, 1H), 4.42-4.47 (dd, 1H), 4.30-4.35 (m, 1H), 4.23 (s, 1H), 4.01-4.06 (m, 1H), 2.67-2.69 (m, 4H); MS (HR-ESI): m/z 461.1248 [M+Na]$^+$.

Example 4

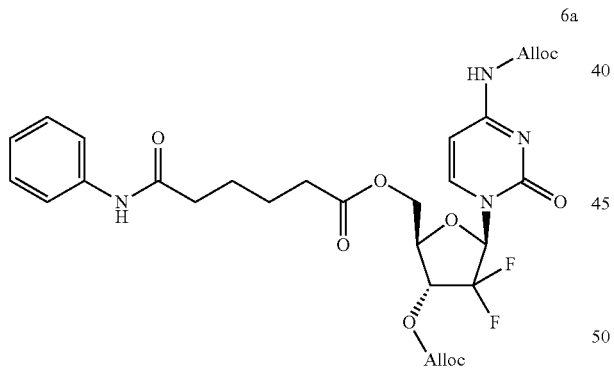

Preparation of 4-Allyloxycarbonylamino-1-[(2R,4R, 5R)-4-allyloxycarbonyloxy-5-(((6-anilino-6-oxo-hexanoyloxy)methyl)-3,3-difluoro-oxolan-2-yl]-1,2-dihydropyrimidin-2-one (6a)

Using Method C and 6-anilino-6-oxo-hexanoic acid, 2 was converted to 6a (colorless oil, 61% yield): $^1$H NMR (400 MHz, DMSO-d$_6$) δ11.04 (s, 1H), 9.87 (s, 1H), 8.08-8.10 (d, 1H), 7.59-7.62 (d, 2H), 7.28-7.33 (t, 2H), 7.17-7.19 (d, 1H), 7.02-7.04 (t, 1H), 6.35-6.39 (t, 1H), 5.94-6.02 (m, 2H), 5.38-5.43 (d, 3H), 5.26-5.34 (dd, 2H), 4.72-4.75 (d, 2H), 4.67-4.69 (d, 2H), 4.52-4.54 (d. 2H), 4.43-4.50 (m, 1H), 2.41-2.45 (t, 2H), 2.32-2.36 (t, 2H), 1.63 (s, 4H).

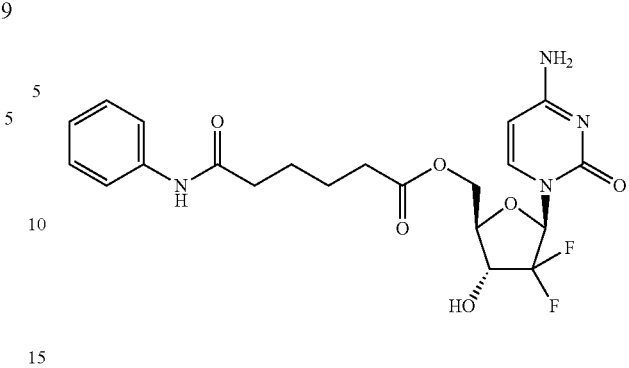

Preparation of 4-Amino-1-[(2R,4R,5R)-5-((6-anilino-6-oxo-hexanoyloxy)methyl)-3,3-difluoro-4-hydroxy-oxolan-2-yl]-1,2-dihydropyrimidin-2-one (6)

Using Method C, 6a was converted to 6 (white solid, 38% yield): $^1$H NMR (400 MHz, DMSO-d$_6$) δ9.88 (s, 1H), 7.60-7.63 (d, 2H), 7.54-7.57 (d, 1H), 7.41-7.44 (d, 2H), 7.29-7.34 (t, 2H), 7.03-7.07 (t, 1H), 6.42-6.44 (d, 1H), 6.19-6.21 (t, 1H), 5.83-5.85 (d, 1H), 4.40-4.45 (dd, 1H), 4.30-4.35 (m, 1H), 4.22 (s, 1H), 4.01-4.07 (m, 1H), 2.43-2.47 (t, 2H), 2.33-2.37 (t, 2H), 1.62-1.65 (t, 4H); MS (HR-ESI): m/z 489.1558 [M+Na]$^+$.

Example 5

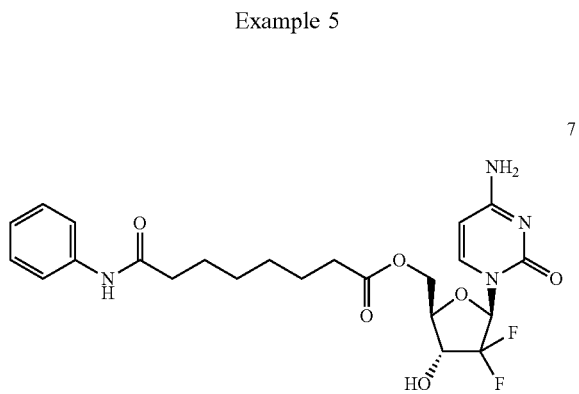

Preparation of 4-Amino-1-[(2R,4R,5R)-5-((8-anilino-8-oxo-octanoyloxy)methyl)-3,3-difluoro-4-hydroxy-oxolan-2-yl]-1,2-dihydropyrimidin-2-one (7)

Using Method C and 8-anilino-8-oxo-octanoic acid, 2 was converted to 7 (white solid, 53% yield): $^1$H NMR (200 MHz, DMSO-d$_6$) δ9.88 (s, 1H), 7.59-7.64 (d, 2H), 7.53-7.57 (d, 1H), 7.45 (s, 2H), 7.27-7.35 (t, 2H), 7.01-7.08 (t, 1H), 6.44-6.47 (d, 1H), 6.16-6.25 (t, 1H), 5.81-5.85 (d, 1H), 4.38-4.40 (d, 1H), 4.33-4.36 (d, 1H), 4.26 (s, 1H), 4.01-4.08 (m, 1H), 2.36-2.44 (t, 2H), 2.29-2.36 (t, 2H) 1.58-1.61 (d, 4H), 1.34 (s, 4H).

Example 6

N4-5'O-derivatized gemcitabine prodrugs can be synthesized according to FIG. 2.

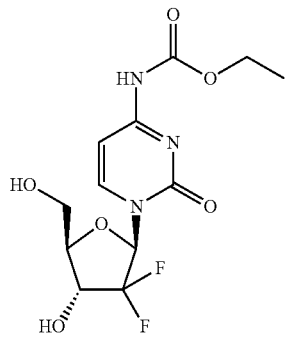

8

Preparation of 1-[(2R,4R,5R)-3,3-Difluoro-4-hydroxy-5-(hydroxy-methyl)oxolan-2-yl]-1,2-dihydro-4-(ethoxycarbonylamino)pyrimidin-2-one (8)

Using Method A and ethyl chloroformate, gemcitabine hydrochloride was converted to 8 (white solid, 64% yield): $^1$H NMR (400 MHz, DMSO-d$_6$) δ10.88 (s, 1H), 8.24-8.27 (d, 1H), 7.13-7.16 (d, 1H), 6.34-6.37 (d, 1H), 6.18-6.22 (t, 1H), 5.32-5.36 (t, 1H), 4.17-4.23 (m, 3H), 3.90-3.94 (m, 1H), 3.82-3.86 (m, 1H), 3.65-3.72 (m, 1H), 1.25-1.29 (t, 3H); MS (HR-ESI): m/z 334.0853 [M−H]$^-$.

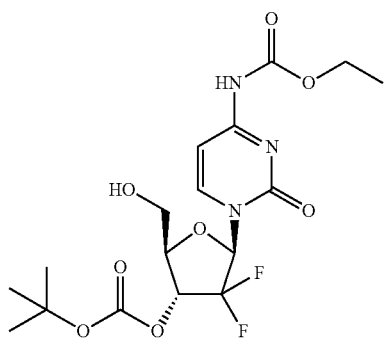

9

Method D: Preparation of 1-[(2R,4R,5R)-4-tert-Butyloxycarbonyloxy-3,3-difluoro-5-(hydroxymethyl)oxolan-2-yl]-1,2-dihydro-4-(ethoxycarbonylamino)-pyrimidin-2-one (9)

To a solution of 8 (2 g, 5.97 mmol) in 20 mL of MeCN, Et$_3$N (2.5 mL, 17.90 mmol) and di-tert-butyl dicarbonate (1.51 mL, 6.56 mmol) were added. The resulting reaction mixture was stirred for 6 h at RT and concentrated in vacuo. The crude residue was purified by flash column chromatography (1:2→2:1 EtOAc/Hexane) to give 1.84 g of 9 (white solid, 70% yield): $^1$H NMR (400 MHz, DMSO-d$_6$) δ10.90 (s, 1H), 8.17-8.19 (d, 1H), 7.16-7.18 (d, 1H), 6.29-6.34 (t, 1H), 5.34-5.37 (t, 1H), 5.23-5.25 (m, 1H), 4.27-4.29 (m, 1H), 4.20-4.23 (m, 2H), 3.81-3.84 (m, 1H), 3.68-3.73 (m, 1H), 1.50 (s, 9H), 1.26-1.29 (t, 3H).

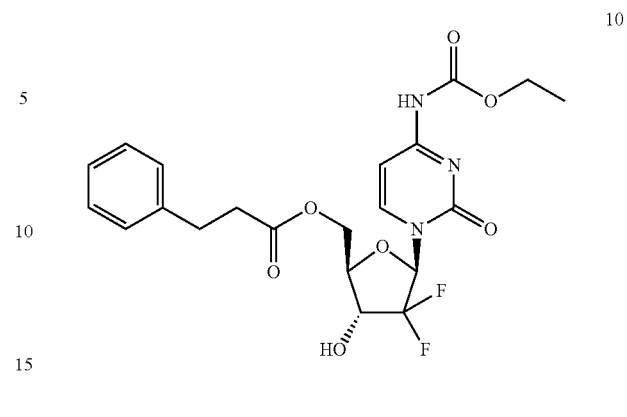

10

Method E: Preparation of 1-[(2R,4R,5R)-3,3-Difluoro-4-hydroxy-5-(3-phenylpropanoyloxymethyl)oxolan-2-yl]-1,2-dihydro-4-(ethoxycarbonylamino)-pyrimidin-2-one (10)

To a mixture of 9 (150 mg, 0.35 mmol), 3-phenylpropanoic acid (57 mg, 0.38 mmol), 4-dimethylaminopyridine (8 mg, 0.07 mmol) and 4 mL of dimethoxyethane, N,N'-dicyclohexylcarbodiimide (158 mg, 0.77 mmol) was added at 0° C. The reaction mixture was stirred overnight at RT and, after filtering off the resulting precipitates, was then concentrated in vacuo. Purification by flash column chromatography (1:1 EtOAc/Hexane) provided 109 mg of colorless oil. To a solution of this colorless oil (109 mg, 0.19 mmol) in 2 mL of CH$_2$Cl$_2$, 2 mL of trifluoroacetic acid was added. Then the resulting reaction mixture was stirred for 1 h at RT, concentrated in vacuo and extracted with EtOAc. The organic extract was washed with brine, dried over Na$_2$SO$_4$, concentrated, then purified by flash column chromatography (2:1 EtOAc/Hexane) to give 83 mg of 10 (colorless oil, 92% yield): $^1$H NMR (400 MHz, DMSO-d$_6$) δ10.89 (s, 1H), 7.99-8.02 (d, 1H), 7.15-7.33 (m, 6H), 6.49-6.52 (d, 1H), 6.21-6.26 (t, 1H), 4.34-4.46 (m, 2H), 4.17-4.28 (m, 3H), 4.04-4.13 (m, 1H), 2.88-2.93 (t, 2H), 2.74-2.77 (t, 2H), 1.26-1.29 (t, 3H); MS (HR-ESI) m/z 490.1405 [M+H]$^+$.

Example 7

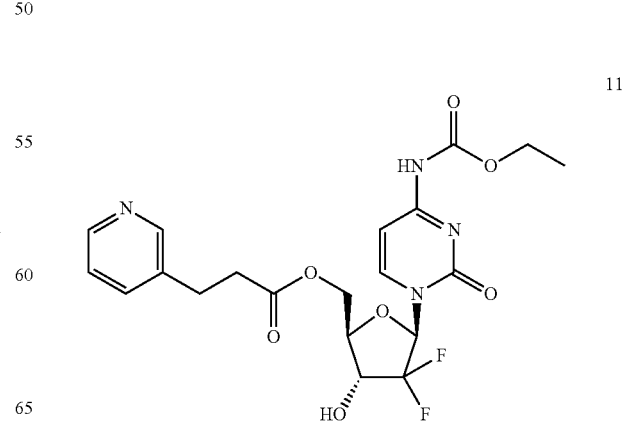

11

Preparation of 1-[(2R,4R,5R)-3,3-Difluoro-4-hydroxy-5-(3-(3-pyridyl)-propanoyloxymethyl)oxolan-2-yl]-1,2-dihydro-4-(ethoxycarbonylamino)-pyrimidin-2-one (11)

Using Method E and 3-(3-pyridyl)propanoic acid, 9 was converted to 11 (yellow solid, 73% yield): $^1$H NMR (400 MHz, DMSO-$d_6$) δ10.89 (s, 1H), 8.50 (s, 1H), 8.42-8.45 (m, 1H), 7.99-8.02 (d, 1H), 7.69-7.72 (d, 1H), 7.31-7.35 (m, 1H), 7.15-7.18 (d, 1H), 6.50-6.52 (d, 1H), 6.21-6.26 (t, 1H), 4.34-4.46 (m, 2H), 4.17-4.24 (m, 3H), 4.04-4.12 (m, 1H), 2.90-2.95 (t, 2H), 2.78-2.82 (t, 2H), 1.25-1.29 (t, 3H); MS (FAB) m/z 469.1528 [M+H]$^+$.

Example 8

Preparation of 1-[(2R,4R,5R)-5-((6-Anilino-6-oxo-hexanoyloxy)methyl)-3,3-difluoro-4-hydroxy-oxolan-2-yl]-1,2-dihydro-4-(ethoxycarbonylamino)-pyrimidin-2-one (13)

Using Method E and 6-anilino-6-oxo-hexanoic acid, 9 was converted to 13 (white solid, 56% yield): $^1$H NMR (400 MHz, DMSO-$d_6$) δ10.88 (s, 1H), 9.88 (s, 1H), 8.02-8.05 (d, 1H), 7.59-7.65 (d, 2H), 7.29-7.35 (t, 2H), 7.16-7.19 (d, 1H), 7.03-7.07 (t, 1H), 6.50-6.53 (d, 1H), 6.23-6.26 (t, 1H), 4.35-4.47 (m, 2H), 4.18-4.35 (m, 3H), 4.05-4.08 (d, 1H), 2.44-2.46 (t, 2H), 2.34-2.36 (t, 2H), 1.63 (s, 4H), 1.24-1.28 (t, 3H); MS (HR-ESI) m/z 561.1762 [M+Na]$^+$.

Example 10

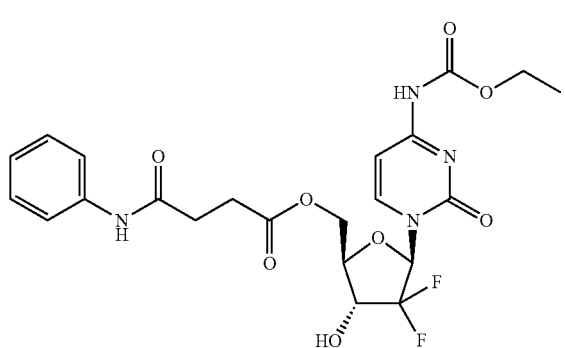

12

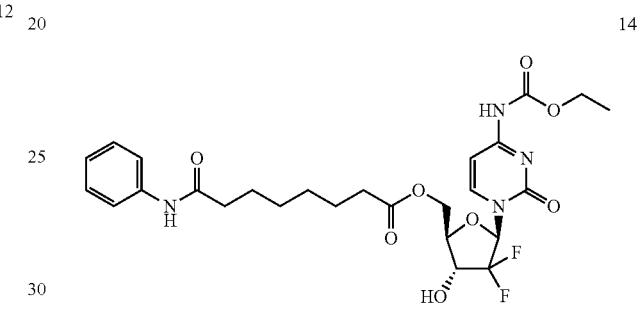

14

Preparation of 1-[(2R,4R,5R)-5-((4-Anilino-4-oxo-butanoyloxy)methyl)-3,3-difluoro-4-hydroxy-oxolan-2-yl]-1,2-dihydro-4-(ethoxycarbonylamino)-pyrimidin-2-one (12)

Using Method E and 4-anilino-4-oxo-butanoic acid, 9 was converted to 12 (white solid, 88% yield): $^1$H NMR (400 MHz, DMSO-$d_6$) δ10.89 (s, 1H), 10.03 (s, 1H), 8.04-8.06 (d, 1H), 7.59-7.61 (d, 2H), 7.28-7.32 (t, 2H), 7.18-7.21 (d, 1H), 7.02-7.06 (t, 1H), 6.52-6.54 (d, 1H), 6.21-6.26 (t, 1H), 4.47-4.51 (d, 1H), 4.37-4.40 (m, 1H), 4.34 (s, 1H), 4.11-4.23 (m, 3H), 2.66-2.73 (m, 4H), 1.24-1.29 (t, 3H).

Example 9

Preparation of 1-[(2R,4R,5R)-5-((8-Anilino-8-oxo-octanoyloxy)methyl)-3,3-difluoro-4-hydroxy-oxolan-2-yl]-1,2-dihydro-4-(ethoxycarbonylamino)-pyrimidin-2-one (14)

Using Method E and 8-anilino-8-oxo-octanoic acid, 9 was converted to 14 (white solid, 66% yield): $^1$H NMR (400 MHz, DMSO-$d_6$) δ10.88 (s, 1H), 9.85 (s, 1H), 8.02-8.04 (d, 1H), 7.60-7.63 (d, 2H), 7.28-7.33 (t, 2H), 7.16-7.19 (d, 1H), 7.02-7.07 (t, 1H), 6.50-6.53 (d, 1H), 6.22-6.27 (t, 1H), 4.34-4.47 (m, 2H), 4.11-4.30 (m, 4H), 2.39-2.44 (t, 2H), 2.30-2.34 (t, 2H), 1.57-1.64 (m, 4H), 1.33-1.36 (t, 4H), 1.24-1.28 (t, 3H); MS (HR-ESI) m/z 565.2112 [M−H]$^-$.

Example 11

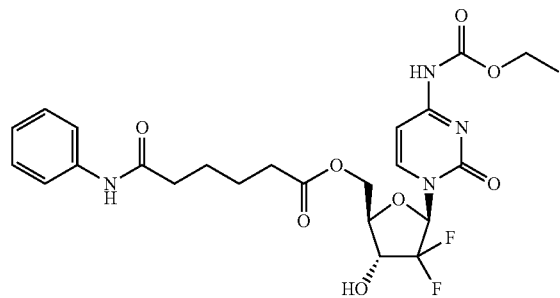

13

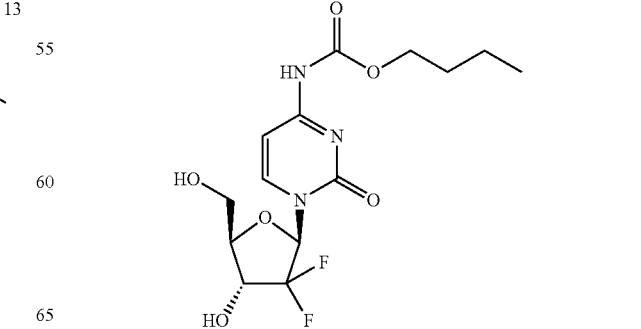

15

Preparation of 4-(Butyloxycarbonylamino)-1-[(2R, 4R,5R)-3,3-difluoro-4-hydroxy-5-(hydroxymethyl) oxolan-2-yl]-1,2-dihydropyrimidin-2-one (15)

Using Method A and butyl chloroformate, gemcitabine hydrochloride was converted to 15 (white solid, 91% yield): $^1$H NMR (200 MHz, DMSO-$d_6$) δ10.87 (s, 1H), 8.23-8.27 (d, 1H), 7.11-7.15 (d, 1H), 6.37 (s, 1H), 6.16-6.23 (t, 1H), 5.33 (s, 1H), 4.12-4.18 (t, 2H), 3.65-3.95 (m, 4H), 1.44-1.66 (m, 2H), 1.33-1.40 (m, 2H), 0.93-0.97 (t, 3H).

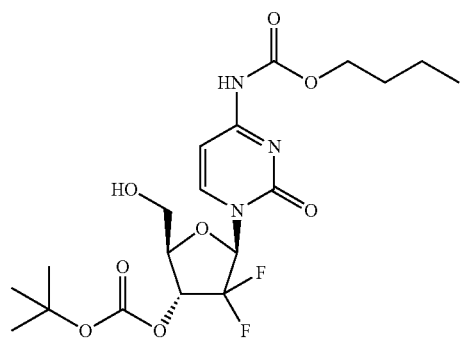

Preparation of 4-(Butyloxycarbonylamino)-1-[(2R, 4R,5R)-4-tert-butyloxycarbonyloxy-3,3-difluoro-5-(hydroxymethyl)oxolan-2-yl]-1,2-dihydropyrimidin-2-one (16)

Using Method D, 15 was converted to 16 (white solid, 62% yield): $^1$H NMR (200 MHz, DMSO-$d_6$) δ10.92 (s, 1H), 8.16-8.20 (d, 1H), 7.14-7.19 (d, 1H), 6.27-6.36 (t, 1H), 5.33-5.40 (t, 1H), 5.17-5.30 (m, 1H), 4.24-4.31 (m, 1H), 4.12-4.19 (t, 2H), 3.64-3.88 (m, 2H), 1.54-1.70 (m, 2H), 1.49 (s, 9H), 1.33-1.48 (m, 2H), 0.90-0.98 (t, 3H).

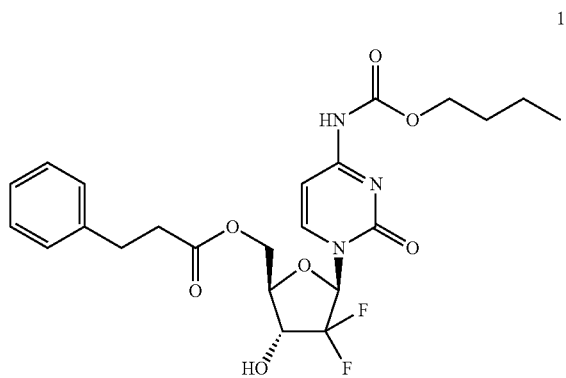

Preparation of 4-(Butyloxycarbonylamino)-1-[(2R, 4R,5R)-3,3-difluoro-4-hydroxy-5-(3-phenylpropanoyloxymethyl)oxolan-2-yl]-1,2-dihydropyrimidin-2-one (17)

Using Method E and 3-phenylpropanoic acid, 16 was converted to 17 (yellow oil, 72% yield): $^1$H NMR (200 MHz, DMSO-$d_6$) δ10.92 (s, 1H), 7.99-8.03 (d, 1H), 7.25-7.31 (t, 5H), 7.14-7.18 (d, 1H), 6.51 (s, 1H), 6.19-6.28 (t, 1H), 4.38-4.40 (d, 2H), 4.01-4.19 (m, 4H), 2.87-2.94 (t, 2H), 2.71-2.78 (t, 2H), 1.59-1.66 (m, 2H), 1.33-1.45 (m, 2H), 0.90-0.97 (t, 3H).

Example 12

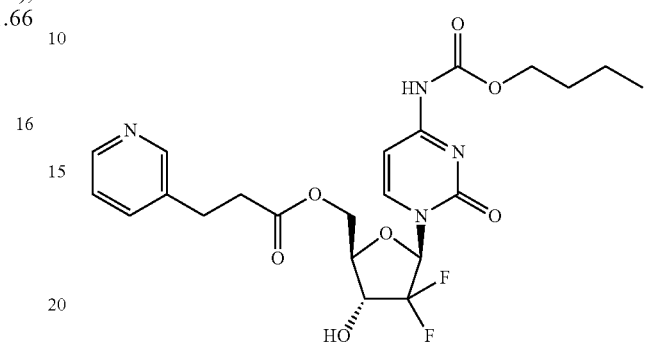

Preparation of 4-(Butyloxycarbonylamino)-1-[(2R, 4R,5R)-3,3-difluoro-4-hydroxy-5-(3-(3-pyridyl)propanoyloxymethyl)oxolan-2-yl]-1,2-dihydro-pyrimidin-2-one (18)

Using Method E and 3-(3-pyridyl)propanoic acid, 16 was converted to 18 (white solid, 77% yield): $^1$H NMR (200 MHz, DMSO-$d_6$) δ10.91 (s, 1H), 8.50-8.51 (d, 1H), 8.41-8.45 (m, 1H), 7.99-8.03 (d, 1H), 7.67-7.74 (m, 1H), 7.29-7.36 (m, 1H), 7.13-7.17 (d, 1H), 6.51-6.54 (d, 1H), 6.19-6.27 (t, 1H), 4.40 (s, 2H), 4.12-4.19 (t, 4H), 2.89-2.92 (d, 2H), 2.80-2.83 (d, 2H), 1.56-1.66 (m, 2H), 1.33-1.45 (m, 2H), 0.90-0.97 (t, 3H).

Example 13

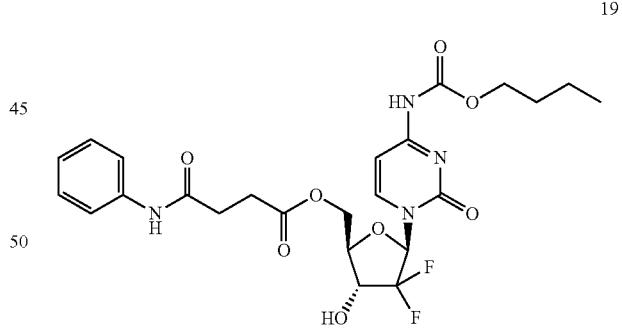

Preparation of 1-[(2R,4R,5R)-5-((4-Anilino-4-oxo-butanoyloxy)methyl)-3,3-difluoro-4-hydroxy-oxolan-2-yl]-4-(butyloxycarbonylamino)-1,2-dihydro-pyrimidin-2-one (19)

Using Method E and 4-anilino-4-oxo-butanoic acid, 16 was converted to 19 (white solid, 90% yield): $^1$H NMR (200 MHz, DMSO-$d_6$) δ10.89 (s, 1H), 10.03 (s, 1H), 8.03-8.07 (d, 1H), 7.58-7.62 (d, 2H), 7.26-7.34 (t, 2H), 7.17-7.20 (d, 1H), 7.00-7.08 (t, 1H), 6.51 (s, 1H), 6.19-6.28 (t, 1H), 4.27-4.53 (m, 3H), 4.12-4.19 (t, 3H), 2.70 (s, 4H), 1.59-1.67 (t, 2H), 1.33-1.44 (t, 2H), 0.90-0.97 (t, 3H).

Example 14

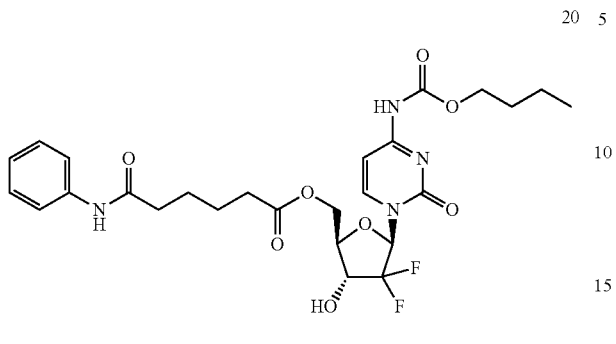 [SMILES: CCCCCOC(=O)Nc1ccn([C@@H]2O[C@H](COC(=O)CCCCC(=O)Nc3ccccc3)[C@@H](O)C2(F)F)c(=O)n1]

Preparation of 1-[(2R,4R,5R)-5-((6-Anilino-6-oxo-hexanoyloxy)methyl)-3,3-difluoro-4-hydroxy-oxo-lan-2-yl]-4-(butyloxycarbonylamino)-1,2-dihydro-pyrimidin-2-one (20)

Using Method E and 6-anilino-6-oxo-hexanoic acid, 16 was converted to 20 (yellow oil, 93% yield): $^1$H NMR (200 MHz, DMSO-$d_6$) δ10.90 (s, 1H), 9.90 (s, 1H), 8.01-8.05 (d, 1H), 7.59-7.63 (d, 2H), 7.26-7.34 (t, 2H), 7.15-7.18 (d, 1H), 7.01-7.08 (t, 1H), 6.51 (s, 1H), 6.20-6.29 (t, 1H), 4.39-4.42 (s, 2H), 4.08-4.18 (m, 4H), 2.46 (s, 2H), 2.35 (s, 2H), 1.62 (s, 8H), 0.89-0.96 (t, 3H).

Example 15

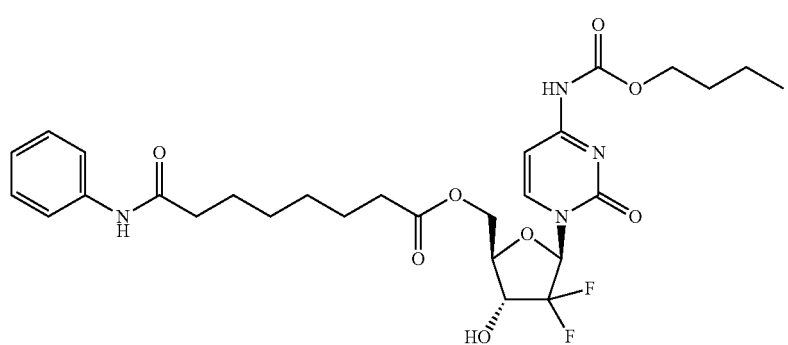

Preparation of 1-[(2R,4R,5R)-5-((8-Anilino-8-oxo-octanoyloxy)methyl)-3,3-difluoro-hydroxy-oxolan-2-yl]-4-(butyloxycarbonylamino)-1,2-dihydro-pyrimidin-2-one (21)

Using Method E and 8-anilino-8-oxo-octanoic acid, 16 was converted to 21 (colorless oil, 90% yield): $^1$H NMR (200 MHz, DMSO-$d_6$) δ10.92 (s, 1H), 9.87 (s, 1H), 8.01-8.05 (d, 1H), 7.59-7.63 (d, 2H), 7.27-7.34 (t, 2H), 7.15-7.19 (d, 1H), 7.00-7.08 (t, 1H), 6.51 (s, 1H), 6.21-6.29 (t, 1H), 4.32-4.49 (m, 2H), 4.08-4.18 (m, 4H), 2.36-2.45 (t, 2H), 2.24-2.32 (t, 2H), 1.58-1.62 (d, 4H), 1.36 (s, 4H), 0.89-0.96 (t, 3H).

Example 16

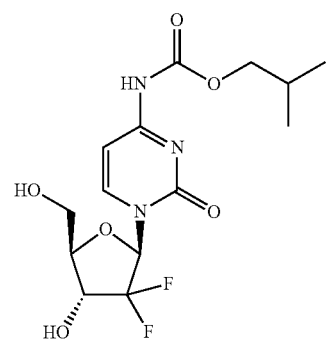

Preparation of 1-[(2R,4R,5R)-3,3-Difluoro-4-hydroxy-5-(hydroxy-methyl)oxolan-2-yl]-1,2-dihydro-4-(2-methylpropyloxycarbonylamino)pyrimidin-2-one (22)

Using Method A and isobutyl chloroformate, gemcitabine hydrochloride was converted to 22 (white solid, 97% yield): $^1$H NMR (500 MHz, DMSO-$d_6$) δ10.88 (s, 1H), 8.25-8.26 (d, 1H), 7.12-7.14 (d, 1H), 6.35 (s, 1H), 6.19-6.22 (t, 1H), 5.33 (s, 1H), 4.22-4.24 (d, 1H), 3.91-3.96 (m, 3H), 3.83-3.85 (d, 1H), 3.68-3.70 (d, 1H), 1.91-1.97 (m, 1H), 0.94-0.95 (d, 6H).

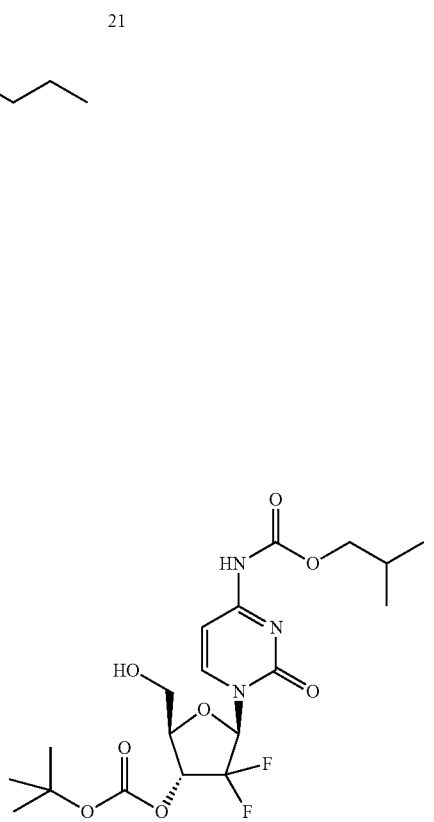

Preparation of 1-[(2R,4R,5R)-4-tert-Butyloxycarbonyloxy-3,3-difluoro-5-(hydroxymethyl)oxolan-2-yl]-1,2-dihydro-4-(2-methylpropyloxy-carbonylamino)pyrimidin-2-one (23)

Using Method D, 22 was converted to 23 (white solid, 61% yield): $^1$H NMR (500 MHz, DMSO-$d_6$) δ10.93 (s, 1H), 8.18-8.19 (d, 1H), 7.16-7.17 (d, 1H), 6.30-6.34 (t, 1H), 5.34-5.37 (t, 1H), 5.21-5.25 (m, 1H), 4.26-4.29 (m, 1H), 3.94-3.96 (d, 2H), 3.81-3.83 (d, 1H), 3.69-3.74 (d, 1H), 1.92-1.98 (m, 1H), 1.49 (s, 9H), 0.94-0.96 (d, 6H).

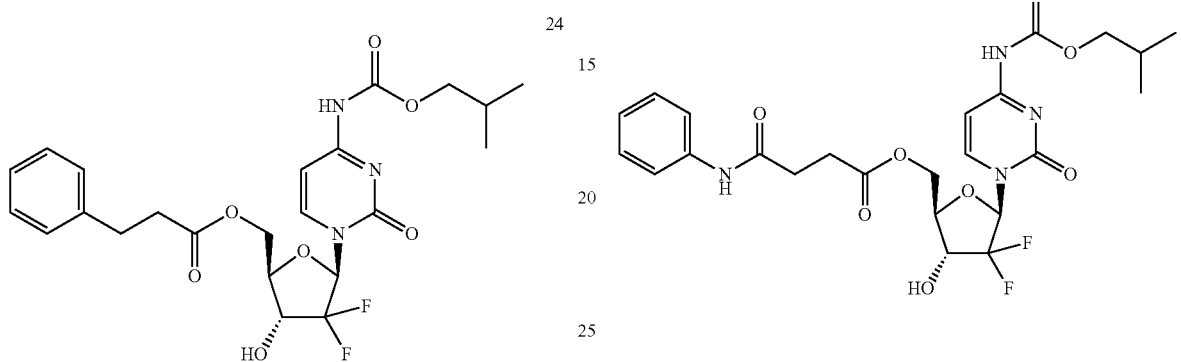

24

Preparation of 1-[(2R,4R,5R)-3,3-Difluoro-4-hydroxy-5-(3-phenyl-propanoyloxymethyl)oxolan-2-yl]-1,2-dihydro-4-(2-methylpropyloxycarbonyl-amino)pyrimidin-2-one (24)

Using Method E and 3-phenylpropanoic acid, 23 was converted to 24 (colorless oil, 61% yield): $^1$H NMR (500 MHz, DMSO-$d_6$) δ10.93 (s, 1H), 8.00-8.02 (d, 1H), 7.15-7.31 (m, 5H), 6.52 (m, 1H), 6.22-6.25 (t, 1H), 4.35-4.44 (m, 2H), 4.25-4.27 (d, 1H), 4.05-4.10 (m, 2H), 3.94-3.96 (d, 2H), 2.89-2.92 (t, 2H), 2.74-2.77 (t, 2H), 1.92-1.97 (m, 1H), 0.94-0.96 (d, 6H).

Example 17

25

Preparation of 1-[(2R,4R,5R)-3,3-Difluoro-4-hydroxy-5-(3-(3-pyridyl)-propanoyloxymethyl)oxolan-2-yl]-1,2-dihydro-4-(2-methylpropyloxycarbonyl-amino)pyrimidin-2-one (25)

Using Method E and 3-(3-pyridyl)propanoic acid, 23 was converted to 25 (white solid, 78% yield): $^1$H NMR (200 MHz, DMSO-$d_6$) δ10.94 (s, 1H), 8.50 (s, 1H), 8.42-8.44 (d, 1H), 7.99-8.03 (d, 1H), 7.69-7.73 (m, 1H), 7.29-7.36 (m, 1H), 7.13-7.17 (d, 1H), 6.51-6.54 (d, 1H), 6.19-6.28 (t, 1H), 4.40 (s, 2H), 4.12-4.19 (t, 4H), 2.89-2.92 (d, 2H), 2.79-2.83 (d, 2H), 1.91-1.98 (t, 1H), 0.93-0.96 (d, 6H).

Example 18

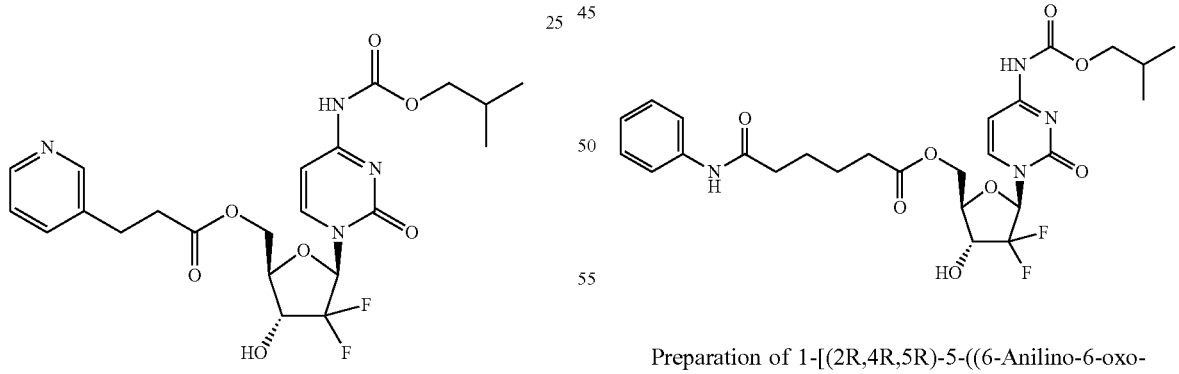

26

Preparation of 1-[(2R,4R,5R)-5-((4-Anilino-4-oxo-butanoyloxy)methyl)-3,3-difluoro-4-hydroxy-oxolan-2-yl]-1,2-dihydro-4-(2-methylpropyloxycarbonyl-amino)pyrimidin-2-one (26)

Using Method E and 4-anilino-4-oxo-butanoic acid, 23 was converted to 26 (white solid, 78% yield): $^1$H NMR (200 MHz, DMSO-$d_6$) δ10.93 (s, 1H), 10.03 (s, 1H), 8.03-8.07 (d, 1H), 7.58-7.62 (d, 2H), 7.26-7.34 (t, 2H), 7.16-7.18 (d, 1H), 7.00-7.08 (t, 1H), 6.51-6.54 (d, 1H), 6.20-6.28 (t, 1H), 4.10-4.52 (m, 4H), 3.92-3.96 (d, 2H), 2.69 (s, 4H), 1.91-1.98 (t, 1H), 0.93-0.96 (d, 6H).

Example 19

27

Preparation of 1-[(2R,4R,5R)-5-((6-Anilino-6-oxo-hexanoyloxy)methyl)-3,3-difluoro-4-hydroxy-oxolan-2-yl]-1,2-dihydro-4-(2-methylpropyloxycarbonyl-amino)pyrimidin-2-one (27)

Using Method E and 6-anilino-6-oxo-hexanoic acid, 23 was converted to 27 (white solid, 83% yield): $^1$H NMR (200 MHz, DMSO-$d_6$) δ10.93 (s, 1H), 9.89 (s, 1H), 8.02-8.06 (d, 1H), 7.59-7.63 (d, 2H), 7.27-7.34 (t, 2H), 7.14-7.18 (d, 1H), 7.01-7.08 (t, 1H), 6.51-6.54 (d, 1H), 6.21-6.29 (t, 1H), 4.12-4.48 (m, 4H), 3.91-3.95 (d, 2H), 2.43-2.49 (t, 2H), 2.32-2.38 (t, 2H), 1.90-1.97 (t, 1H), 1.63 (s, 4H), 0.92-0.95 (d, 6H).

Example 20

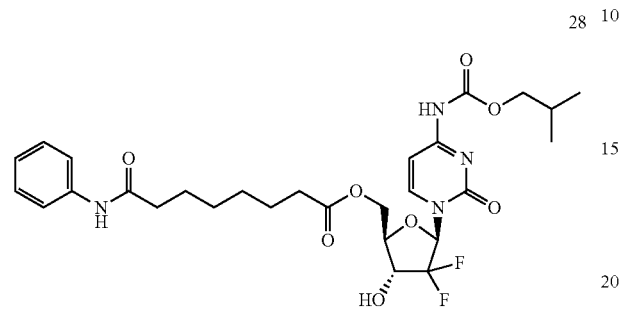

Preparation of 1-[(2R,4R,5R)-5-((8-Anilino-8-oxo-octanoyloxy)methyl)-3,3-difluoro-4-hydroxy-oxolan-2-yl]-1,2-dihydro-4-(2-methylpropyloxycarbonyl-amino)pyrimidin-2-one (28)

Using Method E and 8-anilino-8-oxo-octanoic acid, 23 was converted to 28 (white solid, 45% yield): $^1$H NMR (500 MHz, DMSO-d$_6$) δ10.93 (s, 1H), 9.86 (s, 1H), 8.02-8.04 (d, 1H), 7.60-7.62 (d, 2H), 7.29-7.32 (t, 2H), 7.15-7.17 (d, 1H), 7.03-7.06 (t, 1H), 6.52 (m, 1H), 6.23-6.26 (t, 1H), 4.43-4.45 (d, 1H), 4.35-4.39 (m, 1H), 4.26-4.28 (m, 1H), 4.12-4.14 (t, 1H), 3.93-3.94 (d, 2H), 2.40-2.43 (t, 2H), 2.30-2.33 (t, 2H), 1.92-1.96 (m, 1H), 1.57-1.59 (m, 4H), 1.34 (m, 4H), 0.93-0.94 (d, 6H).

Example 21

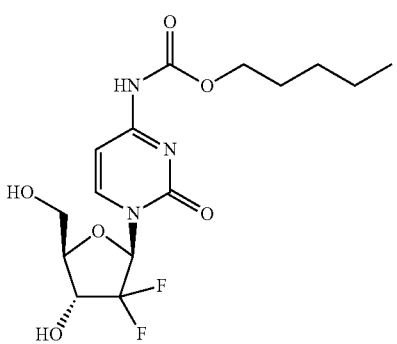

Preparation of 1-[(2R,4R,5R)-3,3-Difluoro-4-hydroxy-5-(hydroxy-methyl)oxolan-2-yl]-1,2-dihydro-4-(pentyloxycarbonylamino)pyrimidin-2-one (29)

Using Method A and pentyl chloroformate, gemcitabine hydrochloride was converted to 29 (white solid, 95% yield): $^1$H NMR (200 MHz, DMSO-d$_6$) δ10.87 (s, 1H), 8.23-8.27 (d, 1H), 7.11-7.15 (d, 1H), 6.34-6.37 (d, 1H), 6.16-6.24 (t, 1H), 5.34 (s, 1H), 4.11-4.18 (t, 3H), 3.82-3.94 (m, 2H), 3.57-3.72 (m, 1H), 1.61-1.68 (t, 2H), 1.34-1.38 (t, 4H), 0.88-0.95 (t, 3H).

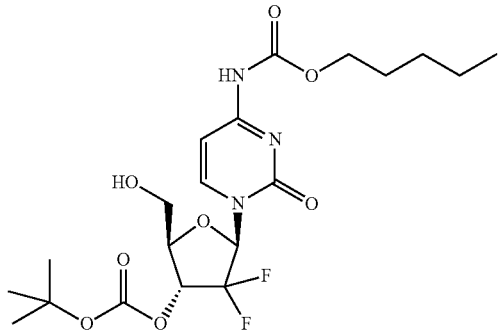

Preparation of 1-[(2R,4R,5R)-4-tert-Butyloxycarbonyloxy-3,3-difluoro-5-(hydroxymethyl)oxolan-2-yl]-1,2-dihydro-4-(pentyloxycarbonylamino)-pyrimidin-2-one (30)

Using Method D, 29 was converted to 30 (white solid, 73% yield): $^1$H NMR (200 MHz, DMSO-d$_6$) δ10.91 (s, 1H), 8.16-8.20 (d, 1H), 7.14-7.18 (d, 1H), 6.27-6.36 (t, 1H), 5.34-5.39 (t, 1H), 5.17-5.30 (m, 1H), 4.26-4.29 (m, 1H), 4.12-4.18 (t, 2H), 3.71-3.79 (m, 2H), 1.61-1.68 (t, 2H), 1.49 (s, 9H), 1.34-1.38 (t, 4H), 0.88-0.95 (t, 3H).

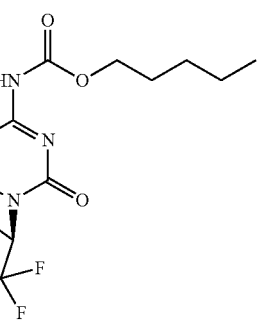

Preparation of 1-[(2R,4R,5R)-3,3-Difluoro-4-hydroxy-5-(3-phenyl-propanoyloxymethyl)oxolan-2-yl]-1,2-dihydro-4-(pentyloxycarbonylamino)-pyrimidin-2-one (31)

Using Method E and 3-phenylpropanoic acid, 30 was converted to 31 (yellow oil, 97% yield): $^1$H NMR (200 MHz, DMSO-d$_6$) δ10.91 (s, 1H), 7.98-8.02 (d, 1H), 7.20-7.30 (m, 5H), 7.13-7.17 (d, 1H), 6.54 (m, 1H), 6.19-6.27 (t, 1H), 4.08-4.40 (m, 6H), 2.87-2.94 (t, 2H), 2.71-2.78 (t, 2H), 1.61-1.67 (t, 2H), 1.33-1.37 (t, 4H), 0.88-0.94 (t, 3H).

Example 22

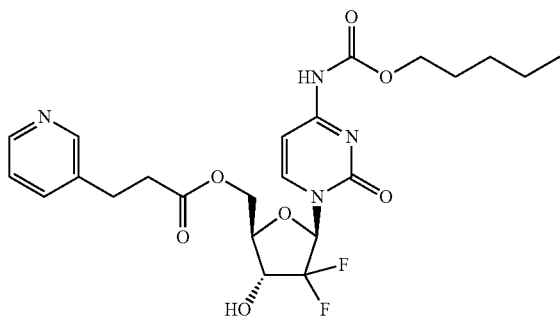

32

Preparation of 1-[(2R,4R,5R)-3,3-Difluoro-4-hydroxy-5-(3-(3-pyridyl)-propanoyloxymethyl)oxolan-2-yl]-1,2-dihydro-4-(pentyloxycarbonylamino)-pyrimidin-2-one (32)

Using Method E and 3-(3-pyridyl)propanoic acid, 30 was converted to 32 (white solid, 97% yield): $^1$H NMR (200 MHz, DMSO-$d_6$) δ10.91 (s, 1H), 8.50-8.51 (d, 1H), 8.42-8.45 (m, 1H), 7.99-8.03 (d, 1H), 7.68-7.74 (m, 1H), 7.30-7.36 (m, 1H), 7.14-7.17 (d, 1H), 6.51-6.54 (d, 1H), 6.19-6.28 (t, 1H), 4.23-4.41 (m, 3H), 4.07-4.08 (t, 3H), 2.89-2.97 (t, 2H), 2.75-2.83 (t, 2H), 1.61-1.68 (t, 2H), 1.30-1.37 (t, 4H), 0.88-0.95 (t, 3H).

Example 23

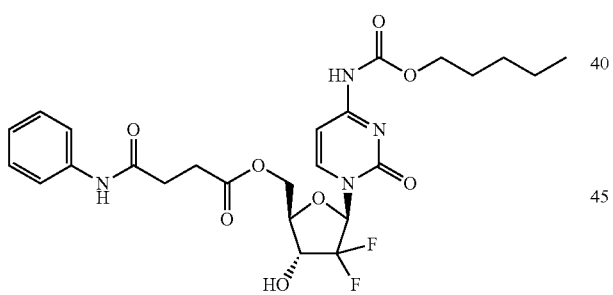

33

Preparation of 1-[(2R,4R,5R)-5-((4-Anilino-4-oxo-butanoyloxy)methyl)-3,3-difluoro-4-hydroxy-oxolan-2-yl]-1,2-dihydro-4-(pentyloxycarbonylamino)-pyrimidin-2-one (33)

Using Method E and 4-anilino-4-oxo-butanoic acid, 30 was converted to 33 (yellow solid, 87% yield): $^1$H NMR (200 MHz, DMSO-$d_6$) δ10.91 (s, 1H), 10.03 (s, 1H), 8.03-8.07 (d, 1H), 7.58-7.62 (d, 2H), 7.26-7.34 (t, 2H), 7.17-7.20 (d, 1H), 7.00-7.08 (t, 1H), 6.52 (m, 1H), 6.20-6.28 (t, 1H), 4.21-4.52 (m, 3H), 4.11-4.17 (t, 3H), 2.70 (s, 4H), 1.61-1.67 (t, 2H), 1.34-1.37 (t, 4H), 0.88-0.95 (t, 3H).

Example 24

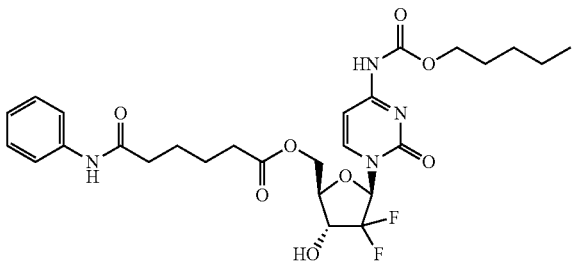

34

Preparation of 1-[(2R,4R,5R)-5-((6-Anilino-6-oxo-hexanoyloxy)methyl)-3,3-difluoro-4-hydroxy-oxolan-2-yl]-1,2-dihydro-4-(pentyloxycarbonylamino)-pyrimidin-2-one (34)

Using Method E and 6-anilino-6-oxo-hexanoic acid, 30 was converted to 34 (white solid, 81% yield): $^1$H NMR (200 MHz, DMSO-$d_6$) δ10.91 (s, 1H), 9.89 (s, 1H), 8.02-8.05 (d, 1H), 7.59-7.63 (d, 2H), 7.27-7.34 (t, 2H), 7.15-7.18 (d, 1H), 7.01-7.08 (t, 1H), 6.53 (m, 1H), 6.21-6.29 (t, 1H), 4.26-4.48 (m, 3H), 4.08-4.17 (t, 3H), 2.46-2.53 (t, 2H), 2.32-2.35 (t, 2H), 1.63 (s, 6H), 1.33-1.36 (t, 4H), 0.87-0.94 (t, 3H).

Example 25

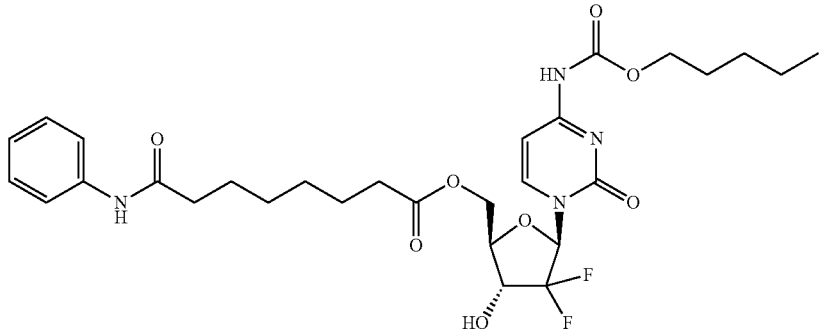

35

Preparation of 1-[(2R,4R,5R)-5-((8-Anilino-8-oxo-octanoyloxy)methyl)-3,3-difluoro-4-hydroxy-oxolan-2-yl]-1,2-dihydro-4-(pentyloxycarbonylamino)-pyrimidin-2-one (35)

Using Method E and 8-anilino-8-oxo-octanoic acid, 30 was converted to 35 (white solid, 86% yield): $^1$H NMR (200 MHz, DMSO-d$_6$) δ10.91 (s, 1H), 9.87 (s, 1H), 8.01-8.05 (d, 1H), 7.59-7.63 (d, 2H), 7.27-7.34 (t, 2H), 7.15-7.19 (d, 1H), 7.01-7.08 (t, 1H), 6.51-6.54 (d, 1H), 6.21-6.29 (t, 1H), 4.24-4.48 (m, 3H), 4.08-4.17 (t, 3H), 2.38-2.45 (t, 2H), 2.28-2.36 (t, 2H), 1.60-1.61 (d, 6H), 1.33-1.36 (t, 8H), 0.87-0.94 (t, 3H).

Example 26

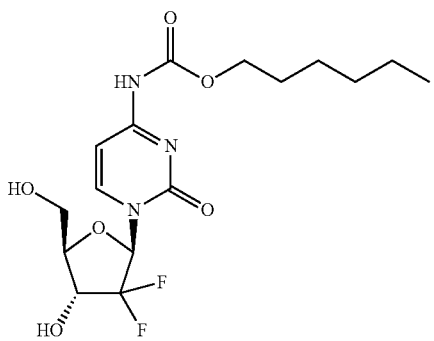

Preparation of 1-[(2R,4R,5R)-3,3-Difluoro-4-hydroxy-5-(hydroxy-methyl)oxolan-2-yl]-1,2-dihydro-4-(hexyloxycarbonylamino)pyrimidin-2-one (36)

Using Method A and hexyl chloroformate, gemcitabine hydrochloride was converted to 36 (white solid, 99% yield): $^1$H NMR (200 MHz, DMSO-d$_6$) δ10.88 (s, 1H), 8.23-8.28 (d, 1H), 7.11-7.15 (d, 1H), 6.34-6.37 (d, 1H), 6.16-6.24 (t, 1H), 5.34 (s, 1H), 4.21-4.26 (m, 1H), 4.10-4.18 (t, 2H), 3.65-3.94 (m, 3H), 1.60-1.67 (t, 2H), 1.31-1.33 (t, 6H), 0.87-0.94 (t, 3H).

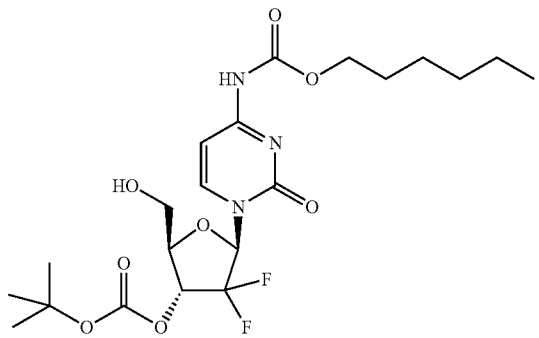

Preparation of 1-[(2R,4R,5R)-4-tert-Butyloxycarbonyloxy-3,3-difluoro-5-(hydroxymethyl)oxolan-2-yl]-1,2-dihydro-4-(hexyloxycarbonylamino)-pyrimidin-2-one (37)

Using Method D, 36 was converted to 37 (white solid, 76% yield): $^1$H NMR (200 MHz, DMSO-d$_6$) δ10.93 (s, 1H), 8.15-8.20 (d, 1H), 7.14-7.18 (d, 1H), 6.27-6.36 (t, 1H), 5.36 (s, 1H), 5.17-5.26 (m, 1H), 4.24-4.31 (m, 1H), 4.11-4.18 (t, 2H), 3.66-3.86 (m, 2H), 1.60-1.67 (t, 2H), 1.49 (s, 9H), 1.31-1.33 (d, 6H), 0.87-0.94 (t, 3H).

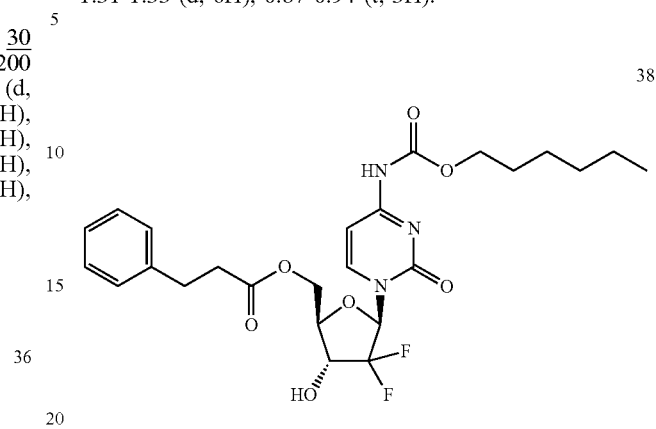

Preparation of 1-[(2R,4R,5R)-3,3-Difluoro-4-hydroxy-5-(3-phenyl-propanoyloxymethyl)oxolan-2-yl]-1,2-dihydro-4-(hexyloxycarbonylamino)-pyrimidin-2-one (38)

Using Method E and 3-phenylpropanoic acid, 37 was converted to 38 (yellow oil, 82% yield): $^1$H NMR (200 MHz, DMSO-d$_6$) δ10.91 (s, 1H), 7.98-8.03 (d, 1H), 7.20-7.31 (m, 5H), 7.13-7.17 (d, 1H), 6.51 (s, 1H), 6.19-6.27 (t, 1H), 4.24-4.48 (m, 3H), 4.11-4.18 (t, 3H), 2.87-2.95 (t, 2H), 2.70-2.78 (t, 2H), 1.60-1.67 (t, 2H), 1.31-1.33 (d, 6H), 0.87-0.94 (t, 3H).

Example 27

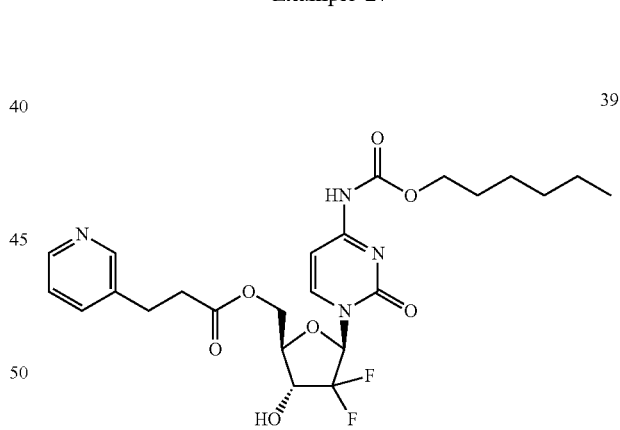

Preparation of 1-[(2R,4R,5R)-3,3-Difluoro-4-hydroxy-5-(3-(3-pyridyl)-propanoyloxymethyl)oxolan-2-yl]-1,2-dihydro-4-(hexyloxycarbonylamino)-pyrimidin-2-one (39)

Using Method E and 3-(3-pyridyl)propanoic acid, 37 was converted to 39 (white solid, 86% yield): $^1$H NMR (200 MHz, DMSO-d$_6$) δ10.91 (s, 1H), 8.49-8.51 (d, 1H), 8.41-8.45 (m, 1H), 7.99-8.03 (d, 1H), 7.67-7.74 (m, 1H), 7.29-7.36 (m, 1H), 7.13-7.17 (d, 1H), 6.53 (s, 1H), 6.19-6.27 (t, 1H), 4.24-4.48 (m, 3H), 4.04-4.18 (t, 3H), 2.88-2.97 (t, 2H), 2.75-2.83 (t, 2H), 1.60-1.67 (t, 2H), 1.31-1.32 (d, 6H), 0.87-0.94 (t, 3H).

Example 28

Preparation of 1-[(2R,4R,5R)-5-((4-Anilino-4-oxo-butanoyloxy)methyl)-3,3-difluoro-4-hydroxy-oxolan-2-yl]-1,2-dihydro-4-(hexyloxycarbonylamino)-pyrimidin-2-one (40)

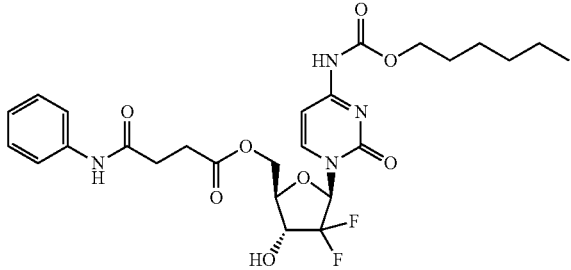

Using Method E and 4-anilino-4-oxo-butanoic acid, 37 was converted to 40 (white solid, 81% yield): $^1$H NMR (200 MHz, DMSO-$d_6$) δ10.90 (s, 1H), 10.03 (s, 1H), 8.03-8.07 (d, 1H), 7.58-7.62 (d, 2H), 7.26-7.34 (t, 2H), 7.17-7.20 (d, 1H), 7.00-7.08 (t, 1H), 6.51-6.54 (d, 1H), 6.19-6.27 (t, 1H), 4.47-4.52 (d, 1H), 4.22-4.40 (m, 2H), 4.11-4.17 (t, 3H), 2.70 (s, 4H), 1.60-1.67 (t, 2H), 1.31-1.32 (d, 6H), 0.87-0.94 (t, 3H).

Example 29

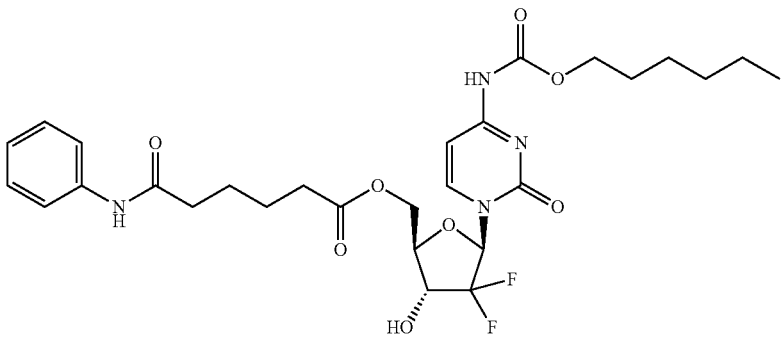

Preparation of 1-[(2R,4R,5R)-5-((6-Anilino-6-oxo-hexanoyloxy)methyl)-3,3-difluoro-4-hydroxy-oxolan-2-yl]-1,2-dihydro-4-(hexyloxycarbonylamino)-pyrimidin-2-one (41)

Using Method E and 6-anilino-6-oxo-hexanoic acid, 37 was converted to 41 (yellow solid, 73% yield): $^1$H NMR (200 MHz, DMSO-$d_6$) δ10.91 (s, 1H), 9.90 (s, 1H), 8.01-8.05 (d, 1H), 7.59-7.63 (d, 2H), 7.27-7.34 (t, 2H), 7.14-7.18 (d, 1H), 7.01-7.08 (t, 1H), 6.53 (m, 1H), 6.20-6.29 (t, 1H), 4.38-4.48 (d, 2H), 4.26-4.32 (d, 1H), 4.10-4.17 (t, 3H), 2.42-2.49 (t, 2H), 2.31-2.39 (t, 2H), 1.63 (s, 6H), 1.31-1.32 (d, 6H), 0.87-0.93 (t, 3H).

Example 30

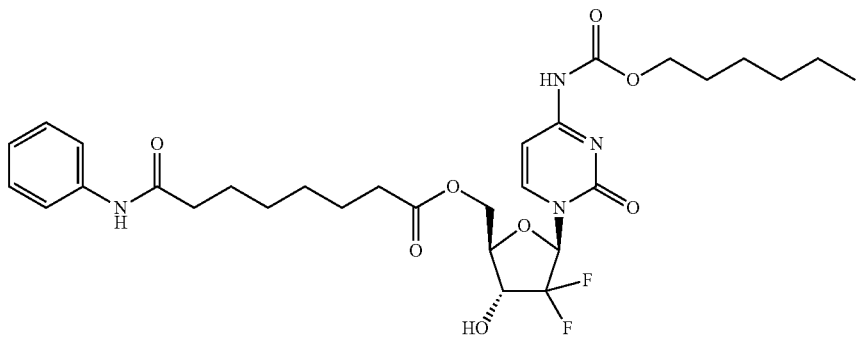

Preparation of 1-[(2R,4R,5R)-5-((8-Anilino-8-oxo-octanoyloxy)methyl)-3,3-difluoro-4-hydroxy-oxolan-2-yl]-1,2-dihydro-4-(hexyloxycarbonylamino)-pyrimidin-2-one (42)

Using Method E and 8-anilino-8-oxo-octanoic acid, 37 was converted to 42 (white solid, 85% yield): ¹H NMR (200 MHz, DMSO-$d_6$) δ10.90 (s, 1H), 9.86 (s, 1H), 8.01-8.05 (d, 1H), 7.59-7.63 (d, 2H), 7.27-7.34 (t, 2H), 7.14-7.18 (d, 1H), 7.00-7.08 (t, 1H), 6.53 (m, 1H), 6.21-6.29 (t, 1H), 4.26-4.39 (m, 3H), 4.08-4.17 (t, 3H), 2.38-2.45 (t, 2H), 2.28-2.35 (t, 2H), 1.59-1.62 (d, 6H), 1.31-1.32 (d, 10H), 0.86-0.93 (t, 3H).

Example 31

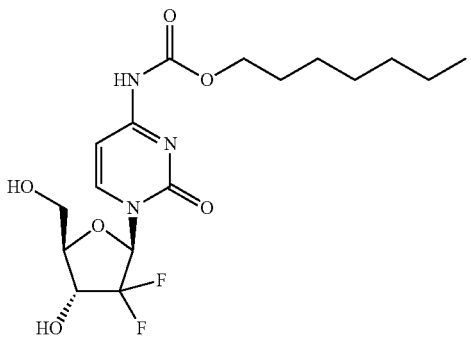

Preparation of 1-[(2R,4R,5R)-3,3-Difluoro-4-hydroxy-5-(hydroxy-methyl)oxolan-2-yl]-1,2-dihydro-4-(heptyloxycarbonylamino)pyrimidin-2-one (43)

Using Method A and heptyl chloroformate, gemcitabine hydrochloride was converted to 43 (white solid, 93% yield): ¹H NMR (200 MHz, DMSO-$d_6$) δ10.87 (s, 1H), 8.24-8.28 (d, 1H), 7.12-7.16 (d, 1H), 6.33-6.37 (d, 1H), 6.16-6.24 (t, 1H), 5.31-5.36 (t, 1H), 4.19-4.33 (m, 1H), 4.10-4.17 (t, 2H), 3.63-3.94 (m, 3H), 1.60-1.66 (t, 2H), 1.29-1.31 (t, 8H), 0.86-0.92 (t, 3H).

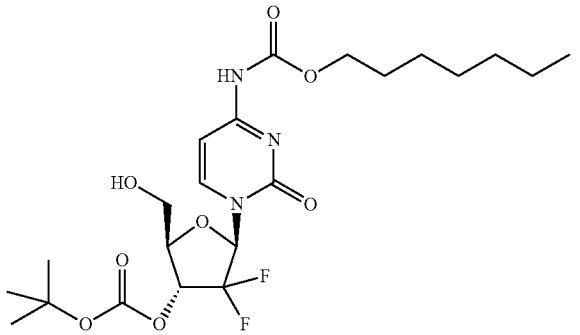

Preparation of 1-[(2R,4R,5R)-4-tert-Butyloxycarbonyloxy-3,3-difluoro-5-(hydroxymethyl)oxolan-2-yl]-1,2-dihydro-4-(heptyloxycarbonylamino)-pyrimidin-2-one (44)

Using Method D, 43 was converted to 44 (white solid, 72% yield): ¹H NMR (200 MHz, DMSO-$d_6$) δ10.91 (s, 1H), 8.16-8.20 (d, 1H), 7.14-7.18 (d, 1H), 6.27-6.36 (t, 1H), 5.34-5.39 (t, 1H), 5.17-5.30 (m, 1H), 4.26-4.29 (t, 1H), 4.11-4.18 (t, 2H), 3.64-3.86 (m, 2H), 1.61-1.67 (t, 2H), 1.49 (s, 9H), 1.29-1.31 (t, 8H), 0.86-0.93 (t, 3H).

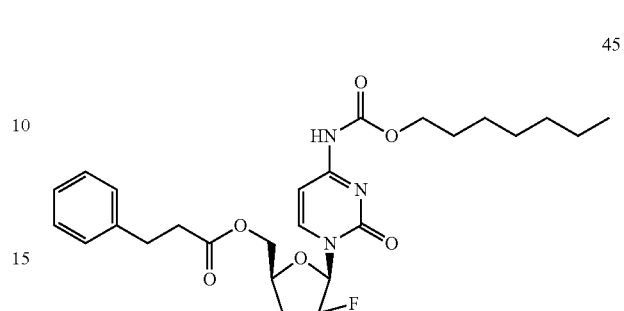

Preparation of 1-[(2R,4R,5R)-3,3-Difluoro-4-hydroxy-5-(3-phenyl-propanoyloxymethyl)oxolan-2-yl]-1,2-dihydro-4-(heptyloxycarbonylamino)-pyrimidin-2-one (45)

Using Method E and 3-phenylpropanoic acid, 44 was converted to 45 (yellow oil, 96% yield): ¹H NMR (200 MHz, DMSO-$d_6$) δ10.91 (s, 1H), 7.99-8.03 (d, 1H), 7.20-7.31 (m, 5H), 7.14-7.18 (d, 1H), 6.52 (s, 1H), 6.20-6.28 (t, 1H), 4.25-4.48 (m, 3H), 4.12-4.18 (t, 3H), 2.87-2.95 (t, 2H), 2.70-2.78 (t, 2H), 1.60-1.67 (t, 2H), 1.30-1.33 (d, 8H), 0.86-0.93 (t, 3H).

Example 32

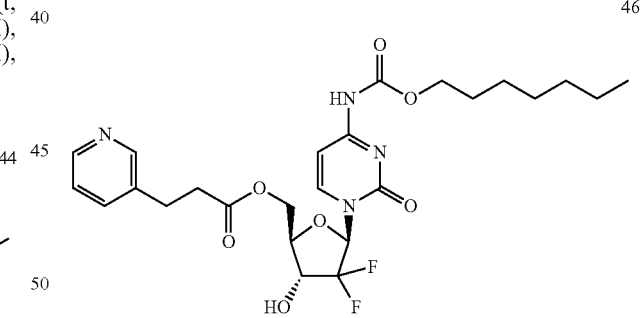

Preparation of 1-[(2R,4R,5R)-3,3-Difluoro-4-hydroxy-5-(3-(3-pyridyl)-propanoyloxymethyl)oxolan-2-yl]-1,2-dihydro-4-(heptyloxycarbonylamino)-pyrimidin-2-one (46)

Using Method E and 3-(3-pyridyl)propanoic acid, 44 was converted to 46 (white solid, 47% yield): ¹H NMR (200 MHz, DMSO-$d_6$) δ10.91 (s, 1H), 8.50-8.51 (d, 1H), 8.42-8.45 (m, 1H), 7.99-8.03 (d, 1H), 7.68-7.73 (m, 1H), 7.29-7.36 (m, 1H), 7.14-7.17 (d, 1H), 6.50-6.53 (d, 1H), 6.19-6.28 (t, 1H), 4.24-4.47 (m, 3H), 4.10-4.18 (t, 3H), 2.89-2.97 (t, 2H), 2.75-2.83 (t, 2H), 1.60-1.67 (t, 2H), 1.30-1.33 (d, 8H), 0.86-0.93 (t, 3H).

Example 33

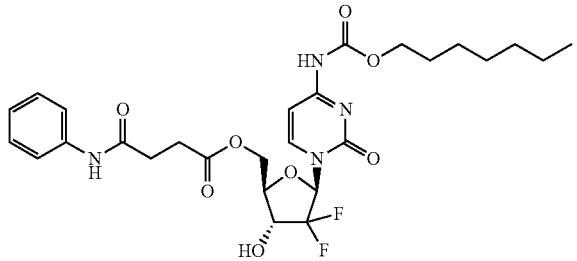

Preparation of 1-[(2R,4R,5R)-5-((4-Anilino-4-oxo-butanoyloxy)methyl)-3,3-difluoro-4-hydroxy-oxolan-2-yl]-1,2-dihydro-4-(heptyloxycarbonylamino)-pyrimidin-2-one (47)

Using Method E and 4-anilino-4-oxo-butanoic acid, 44 was converted to 47 (white solid, 92% yield): $^1$H NMR (200 MHz, DMSO-$d_6$) δ10.89 (s, 1H), 10.02 (s, 1H), 8.03-8.06 (d, 1H), 7.58-7.62 (d, 2H), 7.26-7.34 (t, 2H), 7.17-7.20 (d, 1H), 7.00-7.07 (t, 1H), 6.50-6.54 (d, 1H), 6.20-6.28 (t, 1H), 4.22-4.53 (m, 3H), 4.11-4.17 (t, 3H), 2.70 (s, 4H), 1.60-1.67 (t, 2H), 1.30-1.31 (d, 8H), 0.86-0.93 (t, 3H).

Example 34

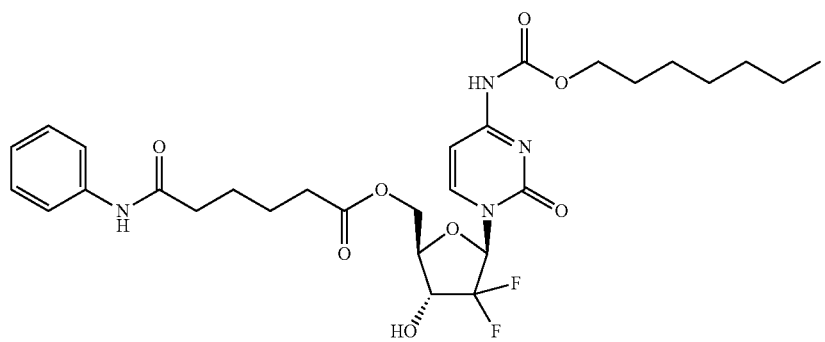

Preparation of 1-[(2R,4R,5R)-5-((6-Anilino-6-oxo-hexanoyloxy)methyl)-3,3-difluoro-4-hydroxy-oxolan-2-yl]-1,2-dihydro-4-(heptyloxycarbonylamino)-pyrimidin-2-one (48)

Using Method E and 6-anilino-6-oxo-hexanoic acid, 44 was converted to 48 (white solid, 90% yield): $^1$H NMR (200 MHz, DMSO-$d_6$) δ10.89 (s, 1H), 9.89 (s, 1H), 8.01-8.05 (d, 1H), 7.59-7.63 (d, 2H), 7.27-7.34 (t, 2H), 7.14-7.18 (d, 1H), 7.01-7.08 (t, 1H), 6.51-6.54 (d, 1H), 6.21-6.29 (t, 1H), 4.25-4.48 (d, 3H), 4.10-4.17 (t, 3H), 2.42-2.49 (t, 2H), 2.32-2.39 (t, 2H), 1.64 (s, 6H), 1.31 (s, 8H), 0.86-0.93 (t, 3H).

Example 35

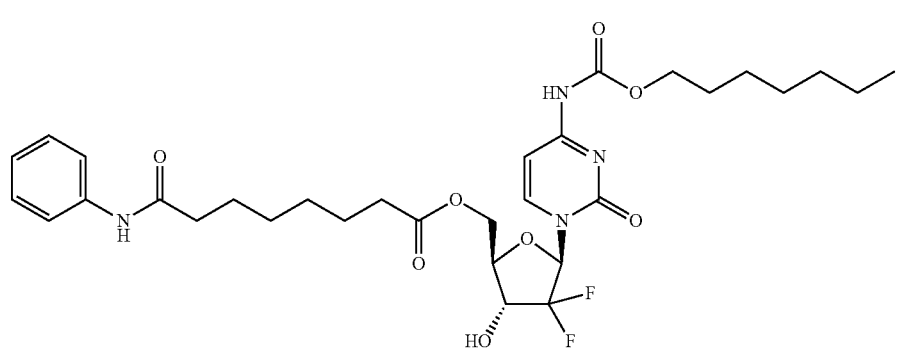

Preparation of 1-[(2R,4R,5R)-5-((8-Anilino-8-oxo-octanoyloxy)methyl)-3,3-difluoro-4-hydroxy-oxolan-2-yl]-1,2-dihydro-4-(heptyloxycarbonylamino)-pyrimidin-2-one (49)

Using Method E and 8-anilino-8-oxo-octanoic acid, 44 was converted to 49 (white solid, 90% yield): $^1$H NMR (200 MHz, DMSO-$d_6$) δ10.90 (s, 1H), 9.86 (s, 1H), 8.01-8.05 (d, 1H), 7.59-7.63 (d, 2H), 7.27-7.34 (t, 2H), 7.15-7.19 (d, 1H), 7.00-7.08 (t, 1H), 6.51-6.54 (d, 1H), 6.21-6.29 (t, 1H), 4.21-4.48 (m, 3H), 4.10-4.17 (t, 3H), 2.38-2.45 (t, 2H), 2.28-2.36 (t, 2H), 1.59-1.62 (d, 6H), 1.30-1.34 (d, 12H), 0.86-0.92 (t, 3H).

Example 36

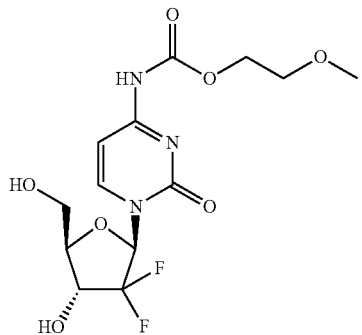

50

Preparation of 1-[(2R,4R,5R)-3,3-Difluoro-4-hydroxy-5-(hydroxy-methyl)oxolan-2-yl]-1,2-dihydro-4-(2-methoxyethyloxycarbonylamino)-pyrimidin-2-one (50)

Using Method A and 2-methoxyethyl chloroformate, gemcitabine hydrochloride was converted to 50 (white solid, 60% yield): $^1$H NMR (500 MHz, DMSO-$d_6$) δ10.92 (s, 1H), 8.25-8.27 (d, 1H), 7.11-7.13 (d, 1H), 6.30-6.32 (t, 1H), 6.18-6.22 (t, 1H), 5.32-5.35 (t, 1H), 4.23-4.26 (m, 2H), 4.13-4.22 (m, 1H), 3.86-3.90 (m, 1H), 3.78-3.81 (m, 1H), 3.62-3.66 (m, 1H), 3.54-3.57 (m, 2H), 3.32 (s, 3H).

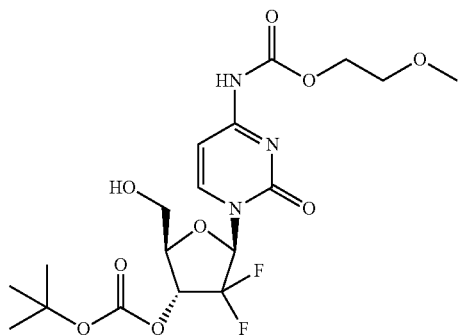

51

Preparation of 1-[(2R,4R,5R)-4-tert-Butyloxycarbonyloxy-3,3-difluoro-5-(hydroxymethyl)oxolan-2-yl]-1,2-dihydro-4-(2-methoxyethyloxy-carbonylamino)pyrimidin-2-one (51)

Using Method D, 50 was converted to 51 (white solid, 62% yield): $^1$H NMR (500 MHz, DMSO-$d_6$) δ10.97 (s, 1H), 8.18-8.19 (d, 1H), 7.15-7.16 (d, 1H), 6.30-6.33 (t, 1H), 5.35-5.37 (t, 1H), 5.21-5.26 (m, 1H), 4.27-4.30 (m, 3H), 3.81-3.83 (m, 1H), 3.69-3.74 (m, 1H), 3.59-3.61 (t, 2H), 3.31 (s, 3H), 1.50 (s, 9H).

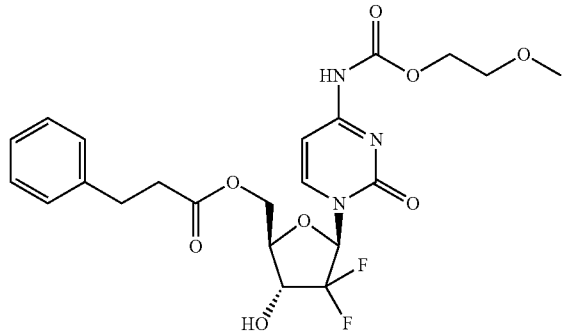

52

Preparation of 1-[(2R,4R,5R)-3,3-Difluoro-4-hydroxy-5-(3-phenyl-propanoyloxymethyl)oxolan-2-yl]-1,2-dihydro-4-(2-methoxyethyloxycarbonyl-amino)pyrimidin-2-one (52)

Using Method E and 3-phenylpropanoic acid, 51 was converted to 52 (white solid, 88% yield): $^1$H NMR (500 MHz, DMSO-$d_6$) δ10.96 (s, 1H), 8.00-8.01 (d, 1H), 7.26-7.32 (m, 4H), 7.20-7.23 (t, 1H), 7.14-7.15 (d, 1H), 6.52 (s, 1H), 6.22-6.25 (t, 1H), 4.37-4.44 (m, 2H), 4.28-4.30 (m, 3H), 4.10-4.12 (m, 1H), 3.59-3.60 (t, 2H), 3.31 (s, 3H), 2.89-2.92 (t, 2H), 2.73-2.76 (t, 2H).

Example 37

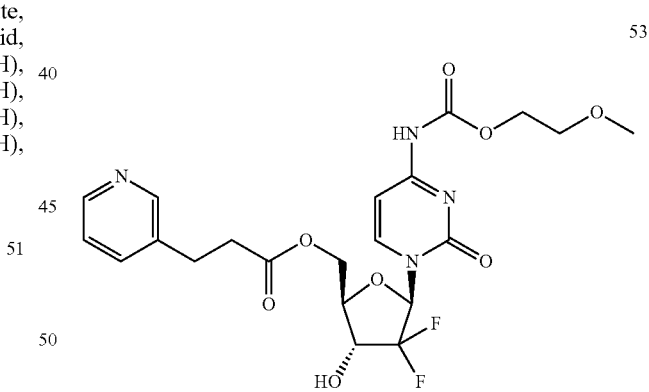

53

Preparation of 1-[(2R,4R,5R)-3,3-Difluoro-4-hydroxy-5-(3-(3-pyridyl)-propanoyloxymethyl)oxolan-2-yl]-1,2-dihydro-4-(2-methoxyethyloxycarbonyl-amino)pyrimidin-2-one (53)

Using Method E and 3-(3-pyridyl)propanoic acid, 51 was converted to 53 (white solid, 13% yield): $^1$H NMR (500 MHz, DMSO-$d_6$) δ10.97 (s, 1H), 8.51 (s, 1H), 8.44 (s, 1H), 8.00-8.02 (d, 1H), 7.70-7.71 (d, 1H), 7.32-7.33 (t, 1H), 7.13-7.15 (d, 1H), 6.51-6.52 (d, 1H), 6.22-6.25 (t, 1H), 4.35-4.44 (m, 2H), 4.28-4.30 (m, 3H), 4.06-4.11 (m, 1H), 3.59-3.60 (t, 2H), 3.31 (s, 3H), 2.91-2.94 (t, 2H), 2.78-2.81 (t, 2H).

Example 38

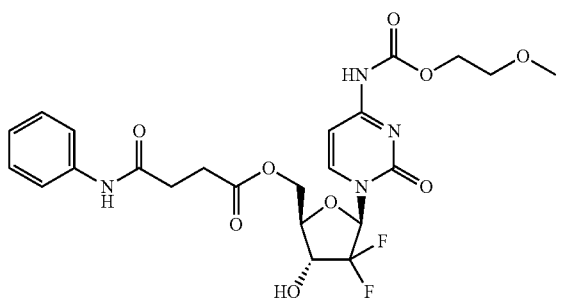

54

Preparation of 1-[(2R,4R,5R)-5-((4-Anilino-4-oxo-butanoyloxy)methyl)-3,3-difluoro-4-hydroxy-oxolan-2-yl]-1,2-dihydro-4-(2-methoxyethyloxycarbonyl-amino)pyrimidin-2-one (54)

Using Method E and 4-anilino-4-oxo-butanoic acid, 51 was converted to 54 (white solid, 84% yield): $^1$H NMR (400 MHz, DMSO-$d_6$) δ10.97 (s, 1H), 10.03 (s, 1H), 8.04-8.06 (d, 1H), 7.59-7.61 (d, 2H), 7.28-7.32 (t, 2H), 7.17-7.19 (d, 1H), 7.02-7.06 (t, 1H), 6.52-6.54 (d, 1H), 6.22-6.26 (t, 1H), 4.47-4.51 (m, 1H), 4.34-4.39 (m, 1H), 4.27-4.30 (t, 3H), 4.11-4.15 (m, 1H), 3.58-3.60 (m, 2H), 3.31 (s, 3H), 2.68-2.73 (m, 4H).

Example 39

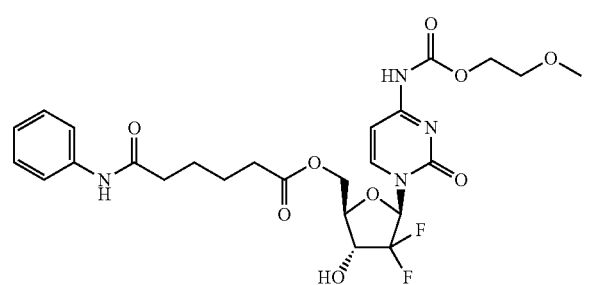

55

Preparation of 1-[(2R,4R,5R)-5-((6-Anilino-6-oxo-hexanoyloxy)methyl)-3,3-difluoro-4-hydroxy-oxolan-2-yl]-1,2-dihydro-4-(2-methoxyethyloxycarbonyl-amino)pyrimidin-2-one (55)

Using Method E and 6-anilino-6-oxo-hexanoic acid, 51 was converted to 55 (colorless oil, 86% yield): $^1$H NMR (500 MHz, DMSO-$d_6$) δ10.91 (s, 1H), 9.84 (s, 1H), 7.98-8.00 (d, 1H), 7.56-7.58 (d, 2H), 7.25-7.29 (t, 2H), 7.10-7.12 (d, 1H), 6.99-7.03 (t, 1H), 6.48 (m, 1H), 6.18-6.22 (t, 1H), 4.32-4.43 (m, 2H), 4.23-4.25 (m, 3H), 4.07-4.11 (m, 1H), 3.54-3.56 (m, 2H), 3.27 (s, 3H), 2.40-2.44 (t, 2H), 2.29-2.33 (t, 2H), 1.59-1.61 (t, 4H).

Example 40

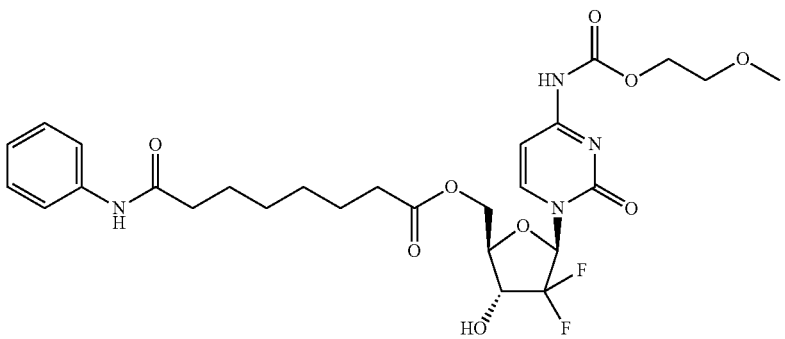

56

Preparation of 1-[(2R,4R,5R)-5-((8-Anilino-8-oxo-octanoyloxy)methyl)-3,3-difluoro-4-hydroxy-oxolan-2-yl]-1,2-dihydro-4-(2-methoxyethyloxycarbonyl-amino)pyrimidin-2-one (56)

Using Method E and 8-anilino-8-oxo-octanoic acid, 51 was converted to 56 (colorless oil, 80% yield): $^1$H NMR (500 MHz, DMSO-$d_6$) δ10.97 (s, 1H), 9.87 (s, 1H), 8.03-8.05 (d, 1H), 7.61-7.63 (d, 2H), 7.29-7.33 (t, 2H), 7.15-7.17 (d, 1H), 7.04-7.08 (t, 1H), 6.54 (m, 1H), 6.24-6.28 (t, 1H), 4.36-4.47 (m, 2H), 4.28-4.30 (m, 3H), 4.12-4.16 (m, 1H), 3.58-3.61 (m, 2H), 3.32 (s, 3H), 2.41-2.44 (t, 2H), 2.31-2.35 (t, 2H), 1.58-1.64 (t, 4H), 1.34-1.37 (m, 4H).

N4-3'O-derivatized gemcitabine prodrugs can be synthesized according to FIG. 3.

Example 41

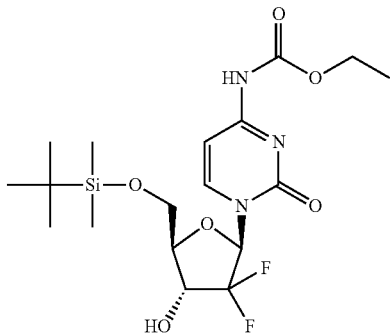

57

Method F: Preparation of 1-[(2R,4R,5R)-5-tert-Butyldimethylsilyloxy-methyl-3,3-difluoro-4-hydroxy-oxolan-2-yl]-1,2-dihydro-4-(ethoxycarbonylamino)pyrimidin-2-one (57)

tert-Butyldimethylsilyl chloride (737 mg, 4.89 mmol) was added to a solution of 8 (1.367 g, 4.08 mmol) in 8 mL of pyridine at 0° C. under $N_2$. The reaction mixture was stirred overnight at RT, diluted with $H_2O$, then extracted with EtOAc. The organic extract was washed with saturated aqueous $CuSO_4$ solution, and brine, dried over $Na_2SO_4$ and concentrated in vacuo. The residue was purified by flash column chromatography (1:1→3:1 EtOAc/Hexane) to give 1.4 g of 57 (white solid, 76% yield): $^1$H NMR (400 MHz, DMSO-$d_6$) δ10.90 (s, 1H), 8.14-8.16 (d, 1H), 7.14-7.16 (d, 1H), 6.42-6.43 (d, 1H), 6.20-6.23 (t, 1H), 4.17-4.23 (m, 3H), 3.98-4.08 (m, 2H), 3.87-3.90 (m, 1H), 1.25-1.28 (t, 3H), 0.94 (s, 9H), 0.14 (s, 6H).

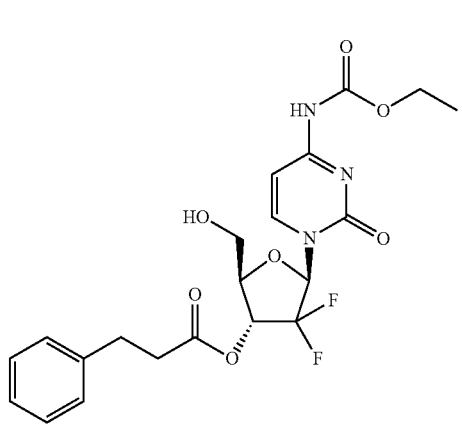

58

Method G: Preparation of 1-[(2R,4R,5R)-3,3-Difluoro-5-hydroxymethyl-4-(3-phenylpropanoyloxy)oxolan-2-yl]-1,2-dihydro-4-(ethoxycarbonylamino)-pyrimidin-2-one (58)

To a mixture of 57 (143 mg, 0.32 mmol), 3-phenylpropanoic acid (853 mg, 0.35 mmol), 4-dimethylaminopyridine (8 mg, 0.06 mmol) and 4 mL of dimethoxyethane, N,N'-dicyclohexylcarbodiimide (144 mg, 0.70 mmol) was added at 0° C. The reaction mixture was stirred overnight at RT and, after filtering off the resulting precipitates, was then concentrated in vacuo. Purification by flash column chromatography (1:2 EtOAc/Hexane) provided 112 mg of a colorless oil. To a solution of this colorless oil (112 mg, 0.19 mmol) in 2.5 mL of THF at 0° C. was added a mixture of trifluoroacetic acid (0.27 mL, 3.47 mmol) and 0.27 mL of water. The reaction mixture was stirred at 0° C. for 5 h, quenched with saturated aqueous $NaHCO_3$ solution and extracted with EtOAc. The extract was washed with water and brine, dried over $Na_2SO_4$ and concentrated in vacuo. Purification by flash column chromatography (2:1 EtOAc/Hexane) afforded 58 (white solid, 48% yield): $^1$H NMR (400 MHz, DMSO-$d_6$) δ 10.90 (s, 1H), 8.20-8.22 (d, 1H), 7.21-7.35 (m, 5H), 7.16-7.19 (d, 1H), 6.29-6.34 (t, 1H), 5.37-5.44 (m, 1H), 5.31-5.34 (t, 1H), 4.18-4.25 (m, 3H), 3.76-3.80 (m, 1H), 3.59-3.66 (m, 1H), 2.92-2.97 (t, 2H), 2.82-2.86 (t, 2H), 1.27-1.30 (t, 3H); MS (HR-ESI) m/z 490.1402 [M+Na]$^+$.

Example 42

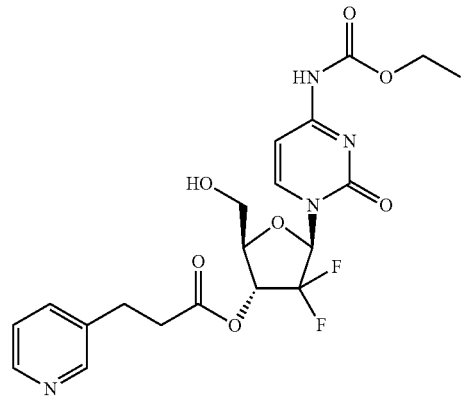

59

Preparation of 1-[(2R,4R,5R)-3,3-Difluoro-5-hydroxymethyl-4-(3-(3-pyridyl)propanoyloxy)oxolan-2-yl]-1,2-dihydro-4-(ethoxycarbonylamino)-pyrimidin-2-one (59)

Using Method G and 3-(3-pyridyl)propanoic acid, 57 was converted to 59 (white solid, 73% yield): $^1$H NMR (400 MHz, DMSO-$d_6$) δ10.90 (s, 1H), 8.52 (s, 1H), 8.44-8.46 (d, 1H), 8.19-8.22 (d, 1H), 7.71-7.74 (d, 1H), 7.33-7.37 (t, 1H), 7.15-7.18 (d, 1H), 6.29-6.32 (t, 1H), 5.34-5.42 (m, 1H), 5.31-5.33 (t, 1H), 4.17-4.26 (m, 3H), 3.77-3.81 (d, 1H), 3.62-3.66 (m, 1H), 2.93-2.96 (t, 2H), 2.90-2.91 (t, 2H), 1.25-1.29 (t, 3H).

Example 43

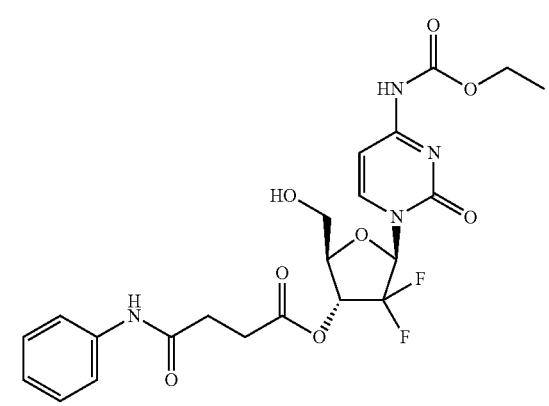

60

Preparation of 1-[(2R,4R,5R)-4-(4-Anilino-4-oxobutanoyloxy)-3,3-difluoro-5-hydroxymethyl-oxolan-2-yl]-1,2-dihydro-4-(ethoxycarbonylamino)-pyrimidin-2-one (60)

Using Method G and 4-anilino-4-oxo-butanoic acid, 57 was converted to 60 (white solid, 87% yield): $^1$H NMR (400 MHz, DMSO-$d_6$) δ10.90 (s, 1H), 10.06 (s, 1H), 8.22-8.23

(d, 1H), 7.60-7.61 (d, 2H), 7.29-7.34 (t, 2H), 7.14-7.18 (t, 1H), 7.04-7.08 (t, 1H), 6.33-6.37 (t, 1H), 5.40-5.47 (m, 1H), 5.34-5.37 (t, 1H), 4.26-4.29 (m, 1H), 4.18-4.23 (m, 2H), 3.80-3.86 (m, 1H), 3.66-3.72 (m, 1H), 2.78-2.82 (t, 2H), 2.69-2.72 (t, 2H), 1.25-1.29 (t, 3H).

Example 44

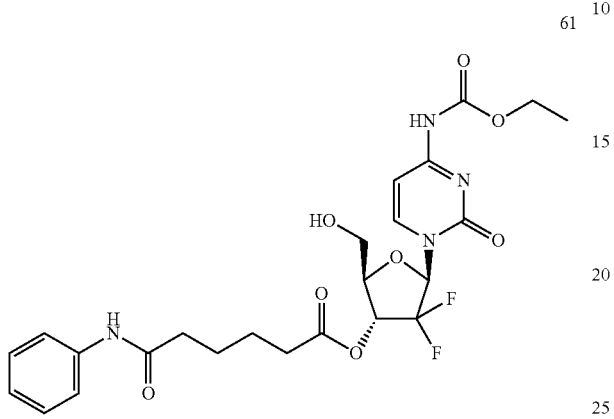

Preparation of 1-[(2R,4R,5R)-4-(6-Anilino-6-oxo-hexanoyloxy)-3,3-difluoro-5-hydroxymethyl-oxolan-2-yl]-1,2-dihydro-4-(ethoxycarbonylamino)-pyrimidin-2-one (61)

Using Method G and 6-anilino-6-oxo-hexanoic acid, 57 was converted to 61 (white solid, 32% yield): $^1$H NMR (500 MHz, DMSO-$d_6$) δ10.91 (s, 1H), 9.90 (s, 1H), 8.20-8.22 (d, 1H), 7.60-7.63 (d, 2H), 7.30-7.33 (t, 2H), 7.16-7.18 (d, 1H), 7.03-7.07 (t, 1H), 6.30-6.34 (t, 1H), 5.39-5.45 (m, 1H), 5.34 (s, 1H), 4.26-4.28 (t, 1H), 4.18-4.23 (m, 2H), 3.81-3.83 (d, 1H), 3.68-3.71 (m, 1H), 2.54 (s, 2H), 2.37 (s, 2H), 1.65 (s, 4H), 1.25-1.29 (t, 3H).

Example 45

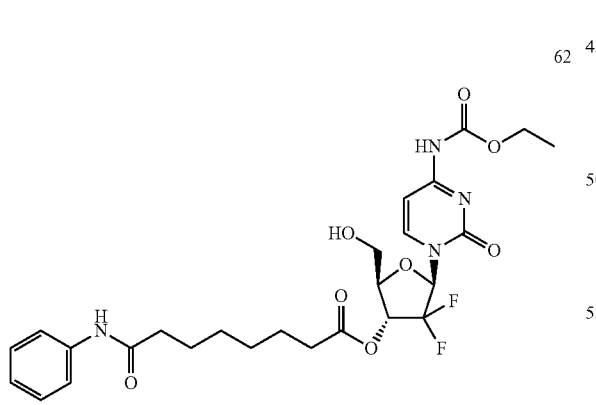

Preparation of 1-[(2R,4R,5R)-4-(8-Anilino-8-oxo-octanoyloxy)-3,3-difluoro-5-hydroxymethyl-oxolan-2-yl]-1,2-dihydro-4-(ethoxycarbonylamino)-pyrimidin-2-one (62)

Using Method G and 8-anilino-8-oxo-octanoic acid, 57 was converted to 62 (white solid, 47% yield): $^1$H NMR (400 MHz, DMSO-$d_6$) δ10.89 (s, 1H), 9.87 (s, 1H), 8.20-8.23 (d, 1H), 7.60-7.63 (d, 2H), 7.29-7.34 (t, 2H), 7.16-7.19 (d, 1H), 7.03-7.07 (t, 1H), 6.29-6.35 (t, 1H), 5.38-5.44 (m, 1H), 5.34 (s, 1H), 4.25-4.29 (m, 1H), 4.18-4.24 (m, 2H), 3.80-3.84 (m, 1H), 3.67-3.71 (m, 1H), 2.47-2.52 (t, 2H), 2.31-2.35 (t, 2H), 1.60-1.64 (t, 4H), 1.36 (s, 4H), 1.25-1.30 (t, 3H); MS (HR-ESI) m/z 567.2266 [M+H]$^+$.

Example 46

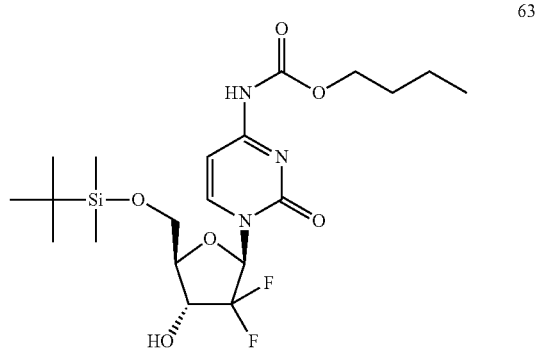 [SMILES: CCCCOC(=O)Nc1ccn([C@@H]2O[C@H](CO[Si](C)(C)C(C)(C)C)[C@@H](O)C2(F)F)c(=O)n1]

Preparation of 1-[(2R,4R,5R)-5-tert-Butyldimethyl-silyloxymethyl-3,3-difluoro-4-hydroxy-oxolan-2-yl]-4-butyloxycarbonylamino-1,2-dihydro-pyrimidin-2-one (63)

Using Method F, 15 was converted to 63 (colorless oil, 88% yield): $^1$H NMR (500 MHz, DMSO-$d_6$) δ10.90 (s, 1H), 8.14-8.15 (d, 1H), 7.13-7.15 (d, 1H), 6.43-6.44 (d, 1H), 6.20-6.23 (t, 1H), 4.18 (m, 1H), 4.14-4.17 (t, 2H), 3.98-4.04 (m, 2H), 3.87-3.90 (m, 1H), 1.60-1.65 (m, 2H), 1.37-1.41 (m, 2H), 0.94 (s, 9H), 0.94 (t, 3H), 0.14 (s, 6H).

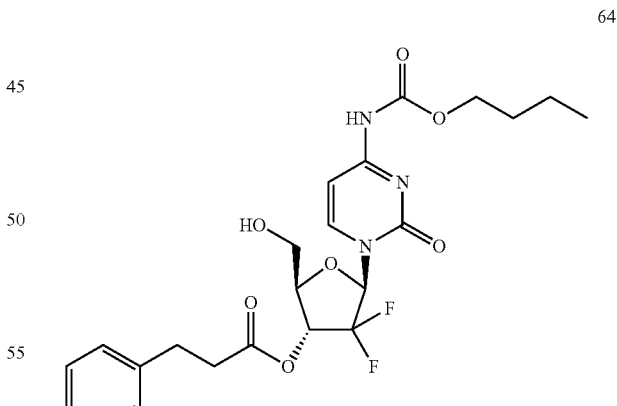

Preparation of 4-Butyloxycarbonylamino-1-[(2R,4R,5R)-3,3-difluoro-5-hydroxymethyl-4-(3-phenylpropanoyloxy)oxolan-2-yl]-1,2-dihydropyrimidin-2-one (64)

Using Method G and 3-phenylpropanoic acid, 63 was converted to 64 (white solid, 69% yield): $^1$H NMR (500

MHz, DMSO-d$_6$) δ10.90 (s, 1H), 8.20-8.22 (d, 1H), 7.23-7.34 (m, 5H), 7.15-7.17 (d, 1H), 6.29-6.33 (t, 1H), 5.37-5.43 (m, 1H), 5.33-5.35 (t, 1H), 4.22-4.25 (m, 1H), 4.14-4.17 (t, 2H), 3.77-3.79 (d, 1H), 3.60-3.65 (m, 1H), 2.92-2.96 (m, 2H), 2.82-2.85 (t, 2H), 1.62-1.64 (m, 2H), 1.38-1.42 (m, 2H), 0.92-0.95 (t, 3H).

Example 47

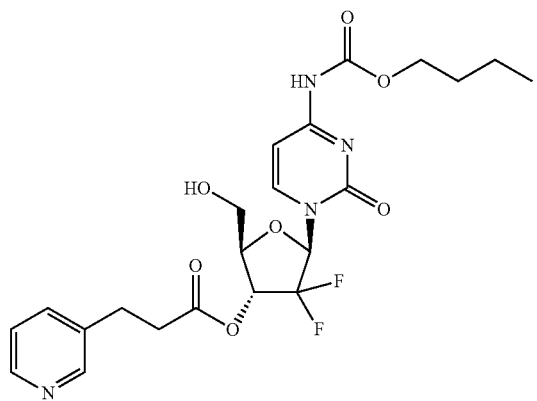

Preparation of 4-Butyloxycarbonylamino-1-[(2R,4R,5R)-3,3-difluoro-5-hydroxymethyl-4-(3-(3-pyridyl)propanoyloxy)oxolan-2-yl]-1,2-dihydro-pyrimidin-2-one (65)

Using Method G and 3-(3-pyridyl)propanoic acid, 63 was converted to 65 (white solid, 44% yield): $^1$H NMR (500 MHz, DMSO-d$_6$) δ10.92 (s, 1H), 8.52 (s, 1H), 8.46 (s, 1H), 8.20-8.21 (d, 1H), 7.72-7.73 (d, 1H), 7.34-7.36 (m, 1H), 7.15-7.17 (d, 1H), 6.29-6.33 (t, 1H), 5.40-5.42 (m, 1H), 5.33-5.35 (t, 1H), 4.24-4.25 (t, 1H), 4.15-4.17 (t, 2H), 3.78-3.80 (m, 1H), 3.62-3.66 (m, 1H), 2.94-2.97 (t, 2H), 2.88-2.91 (t, 2H), 1.61-1.64 (t, 2H), 1.39-1.42 (t, 2H), 0.92-0.95 (t, 3H).

Example 48

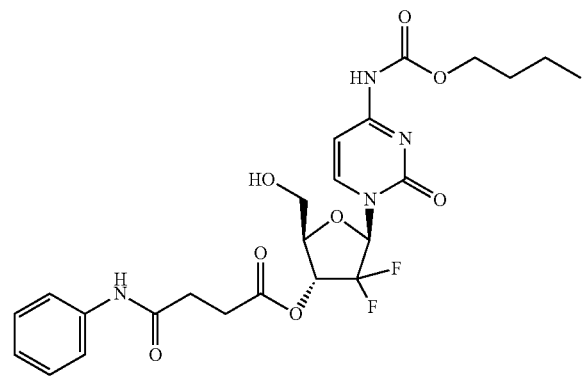

Preparation of 1-[(2R,4R,5R)-4-(4-Anilino-4-oxo-butanoyloxy)-3,3-difluoro-5-hydroxymethyl-oxolan-2-yl]-4-butyloxycarbonylamino-1,2-dihydro-pyrimidin-2-one (66)

Using Method G and 4-anilino-4-oxo-butanoic acid, 63 was converted to 66 (white solid, 87% yield): $^1$H NMR (200 MHz, DMSO-d$_6$) δ10.91 (s, 1H), 10.06 (s, 1H), 8.20-8.24 (d, 1H), 7.59-7.62 (d, 2H), 7.28-7.36 (t, 2H), 7.14-7.18 (d, 1H), 7.02-7.09 (t, 1H), 6.29-6.37 (t, 1H), 5.32-5.59 (m, 2H), 4.25-4.29 (m, 1H), 4.12-4.19 (t, 2H), 3.79-3.88 (m, 1H), 3.66-3.74 (m, 1H), 2.77-2.79 (d, 2H), 2.71-2.73 (d, 2H), 1.59-1.66 (t, 2H), 1.33-1.44 (m, 2H), 0.90-0.97 (t, 3H).

Example 49

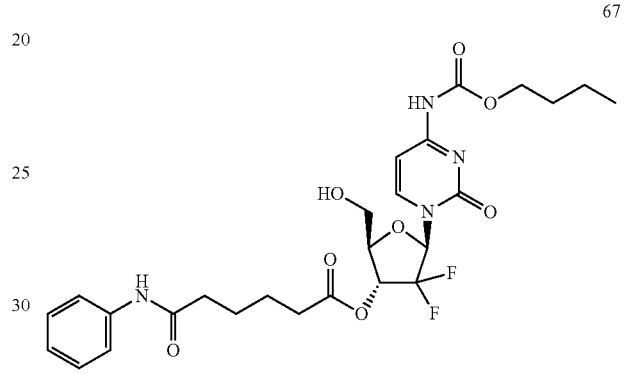

Preparation of 1-[(2R,4R,5R)-4-(6-Anilino-6-oxo-hexanoyloxy)-3,3-difluoro-5-hydroxymethyl-oxolan-2-yl]-4-butyloxycarbonylamino-1,2-dihydro-pyrimidin-2-one (67)

Using Method G and 6-anilino-6-oxo-hexanoic acid, 63 was converted to 67 (white solid, 63% yield): $^1$H NMR (500 MHz, DMSO-d$_6$) δ10.91 (s, 1H), 9.91 (s, 1H), 8.21-8.22 (d, 1H), 7.61-7.63 (d, 2H), 7.30-7.33 (t, 2H), 7.16-7.18 (d, 1H), 7.04-7.07 (t, 1H), 6.31-6.34 (t, 1H), 5.39-5.45 (m, 1H), 5.34-5.36 (t, 1H), 4.27-4.28 (t, 1H), 4.15-4.17 (t, 2H), 3.80-3.83 (m, 1H), 3.68-3.72 (m, 1H), 2.35-2.38 (t, 2H), 1.64-1.66 (m, 8H), 1.40-1.42 (m, 2H), 0.92-0.95 (t, 3H).

Example 50

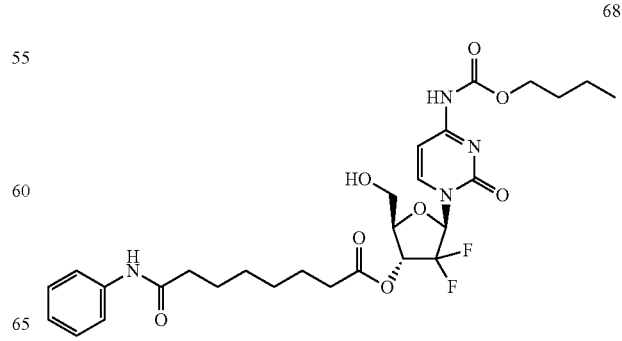

Preparation of 1-[(2R,4R,5R)-4-(8-Anilino-8-oxo-octanoyloxy)-3,3-difluoro-5-hydroxymethyl-oxolan-2-yl]-4-butyloxycarbonylamino-1,2-dihydro-pyrimidin-2-one (68)

Using Method G and 8-anilino-8-oxo-octanoic acid, 63 was converted to 68 (white solid, 53% yield): ¹H NMR (500 MHz, DMSO-d₆) δ10.91 (s, 1H), 9.88 (s, 1H), 8.21-8.22 (d, 1H), 7.61-7.63 (d, 2H), 7.29-7.33 (t, 2H), 7.16-7.18 (d, 1H), 7.03-7.06 (t, 1H), 6.30-6.34 (t, 1H), 5.39-5.45 (m, 1H), 5.34-5.35 (t, 1H), 4.26-4.28 (t, 1H), 4.15-4.17 (t, 2H), 3.80-3.83 (m, 1H), 3.66-3.71 (m, 1H), 2.48-2.51 (t, 2H), 2.31-2.34 (t, 2H), 1.60-1.64 (m, 6H), 1.40-1.42 (m, 6H), 0.92-0.95 (t, 3H).

Example 51

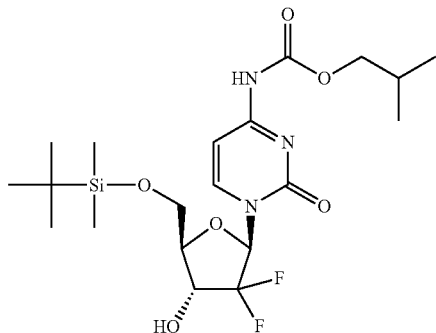

69

Preparation of 1-[(2R,4R,5R)-5-tert-Butydimethylsilyloxymethyl-3,3-difluoro-4-hydroxy-oxolan-2-yl]-1,2-dihydro-4-(2-methylpropyloxycarbonyl-amino)pyrimidin-2-one (69)

Using Method F, 22 was converted to 69 (white solid, 77% yield): ¹H NMR (500 MHz, DMSO-d₆) δ10.93 (s, 1H), 8.14-8.16 (d, 1H), 7.12-7.14 (d, 1H), 6.43-6.45 (d, 1H), 6.20-6.23 (t, 1H), 4.19-4.21 (m, 1H), 3.98-4.02 (m, 2H), 3.94-3.95 (d, 2H), 3.87-3.90 (m, 1H), 1.90-1.98 (m, 1H), 0.95 (d, 6H), 0.94 (s, 9H), 0.14 (s, 6H).

70

Preparation of 1-[(2R,4R,5R)-3,3-Difluoro-5-hydroxymethyl-4-(3-phenylpropanoyloxy)oxolan-2-yl]-1,2-dihydro-4-(2-methylpropyloxycarbonyl-amino)pyrimidin-2-one (70)

Using Method G and 3-phenylpropanoic acid, 69 was converted to 70 (white solid, 71% yield): ¹H NMR (500 MHz, DMSO-d₆) δ10.94 (s, 1H), 8.20-8.22 (d, 1H), 7.22-7.34 (m, 5H), 7.15-7.16 (d, 1H), 6.30-6.33 (t, 1H), 5.38-5.41 (m, 1H), 5.27-5.33 (m, 1H), 4.22-4.24 (m, 1H), 3.94-3.95 (d, 2H), 3.77-3.79 (d, 1H), 3.61-3.64 (d, 1H), 2.92-2.94 (d, 2H), 2.82-2.85 (t, 2H), 1.92-1.97 (m, 1H), 0.94-0.96 (d, 6H).

Example 52

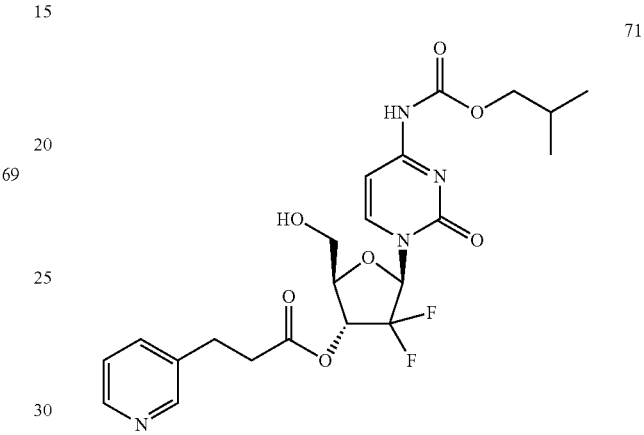

Preparation of 1-[(2R,4R,5R)-3,3-Difluoro-5-hydroxymethyl-4-(3-(3-pyridyl)propanoyloxy)oxolan-2-yl]-1,2-dihydro-4-(2-methylpropyloxycarbonyl-amino)pyrimidin-2-one (71)

Using Method G and 3-(3-pyridyl)propanoic acid, 69 was converted to 71 (white solid, 74% yield): ¹H NMR (500 MHz, DMSO-d₆) δ10.94 (s, 1H), 8.52 (s, 1H), 8.45-8.46 (d, 1H), 8.20-8.21 (d, 1H), 7.72-7.73 (d, 1H), 7.34-7.36 (m, 1H), 7.15-7.16 (d, 1H), 6.29-6.33 (t, 1H), 5.38-5.41 (m, 1H), 5.34 (s, 1H), 4.24-4.25 (m, 1H), 3.94-3.95 (d, 2H), 3.78-3.80 (d, 1H), 3.63-3.65 (d, 1H), 2.94-2.95 (d, 2H), 2.89-2.91 (d, 1H), 1.92-1.97 (m, 2H), 0.94-0.96 (d, 6H).

Example 53

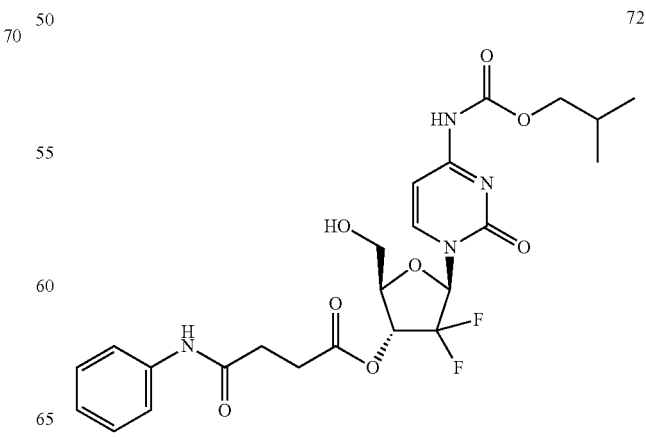

Preparation of 1-[(2R,4R,5R)-4-(4-Anilino-4-oxo-butanoyloxy)-3,3-difluoro-5-hydroxymethyl-oxolan-2-yl]-1,2-dihydro-4-(2-methylpropyloxy-carbonylamino)pyrimidin-2-one (72)

Using Method G and 4-anilino-4-oxo-butanoic acid, 69 was converted to 72 (white solid, 88% yield): ¹H NMR (200 MHz, DMSO-d₆) δ 10.94 (s, 1H), 10.06 (s, 1H), 8.21-8.25 (d, 1H), 7.58-7.62 (d, 2H), 7.28-7.36 (t, 2H), 7.14-7.18 (d, 1H), 7.02-7.09 (t, 1H), 6.29-6.37 (t, 1H), 5.32-5.51 (m, 2H), 4.25-4.29 (m, 1H), 3.93-3.96 (d, 2H), 3.79-3.88 (m, 1H), 3.64-3.74 (m, 1H), 2.77-2.79 (d, 2H), 2.71-2.73 (d, 2H), 1.88-2.01 (m, 1H), 0.93-0.96 (d, 6H).

Example 54

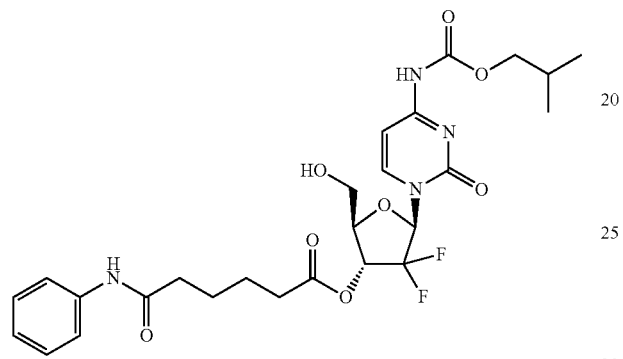

73

Preparation of 1-[(2R,4R,5R)-4-(6-Anilino-6-oxo-hexanoyloxy)-3,3-difluoro-5-hydroxymethyl-oxolan-2-yl]-1,2-dihydro-4-(2-methylpropyloxycarbonylamino)pyrimidin-2-one (27)

Using Method G and 6-anilino-6-oxo-hexanoic acid, 69 was converted to 73 (white solid, 39% yield): ¹H NMR (400 MHz, DMSO-d₆) δ10.94 (s, 1H), 9.92 (s, 1H), 8.21-8.23 (d, 1H), 7.61-7.63 (d, 2H), 7.30-7.34 (t, 2H), 7.16-7.18 (d, 1H), 7.03-7.07 (t, 1H), 6.30-6.35 (t, 1H), 5.60-5.62 (d, 1H), 5.39-5.46 (m, 1H), 5.34-5.37 (t, 1H), 4.26-4.29 (m, 1H), 3.94-3.95 (d, 1H), 3.81-3.84 (d, 1H), 3.67-3.72 (m, 1H), 2.37 (s, 2H), 1.91-1.98 (m, 1H), 1.65 (s, 6H), 0.94-0.96 (d, 6H).

Example 55

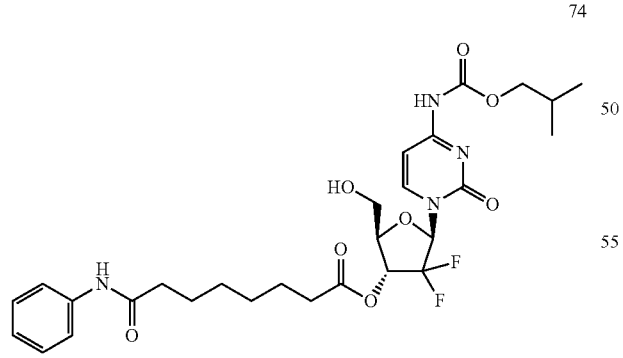 [SMILES: CCCCOC(=O)Nc1ccn([C@@H]2O[C@H](CO)[C@@H](OC(=O)CCCCCCC(=O)Nc3ccccc3)C2(F)F)c(=O)n1]

74

Preparation of 1-[(2R,4R,5R)-4-(8-Anilino-8-oxo-octanoyloxy)-3,3-difluoro-5-hydroxymethyl-oxolan-2-yl]-1,2-dihydro-4-(2-methylpropyloxy-carbonylamino)pyrimidin-2-one (74)

Using Method G and 8-anilino-8-oxo-octanoic acid, 69 was converted to 74 (white solid, 53% yield): ¹H NMR (500 MHz, DMSO-d₆) δ 10.95 (s, 1H), 9.88 (s, 1H), 8.21-8.22 (d, 1H), 7.61-7.62 (d, 2H), 7.30-7.33 (t, 2H), 7.15-7.17 (d, 1H), 7.03-7.06 (t, 1H), 6.30-6.34 (t, 1H), 5.39-5.43 (m, 1H), 5.35 (m, 1H), 4.26-4.28 (m, 1H), 3.94-3.95 (d, 2H), 3.80-3.83 (d, 1H), 3.68-3.69 (d, 1H), 2.48-2.51 (t, 2H), 2.31-2.34 (t, 2H), 1.92-1.96 (m, 1H), 1.60-1.62 (d, 4H), 1.35 (s, 4H), 0.94-0.96 (d, 6H).

Example 56

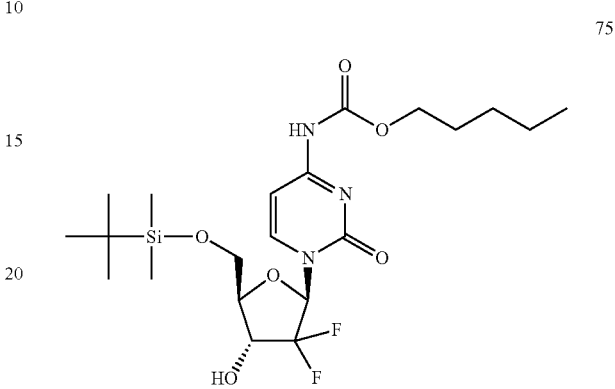

75

Preparation of 1-[(2R,4R,5R)-5-tert-Butyldimethyl-silyloxymethyl-3,3-difluoro-4-hydroxy-oxolan-2-yl]-1,2-dihydro-4-(pentyloxycarbonylamino)-pyrimidin-2-one (75)

Using Method F, 29 was converted to the 75 (colorless oil, 68% yield): ¹H NMR (200 MHz, DMSO-d₆) δ10.90 (s, 1H), 8.13-8.17 (d, 1H), 7.12-7.16 (d, 1H), 6.42-6.44 (d, 1H), 6.18-6.25 (t, 1H), 4.11-4.18 (m, 3H), 3.96-4.08 (m, 2H), 3.84-3.92 (m, 1H), 1.61-1.67 (t, 2H), 1.30-1.39 (t, 4H), 0.94 (s, 9H), 0.94 (t, 3H), 0.14 (s, 6H).

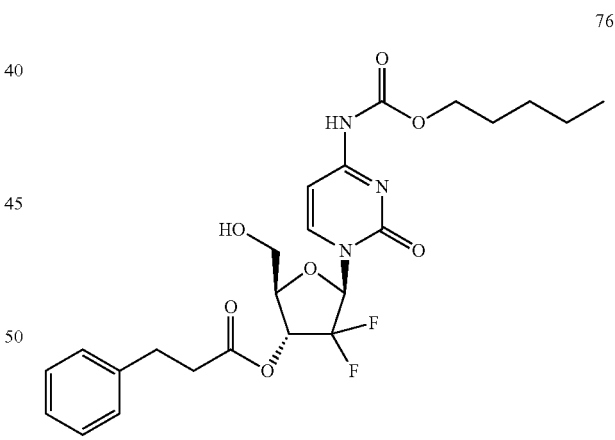

76

Preparation of 1-[(2R,4R,5R)-3,3-Difluoro-5-hydroxymethyl-4-(3-phenylpropanoyloxy)oxolan-2-yl]-1,2-dihydro-4-(pentyloxycarbonylamino)-pyrimidin-2-one (76)

Using Method G and 3-phenylpropanoic acid, 75 was converted to 76 (colorless oil, 90% yield): ¹H NMR (200 MHz, DMSO-d₆) δ10.91 (s, 1H), 8.19-8.23 (d, 1H), 7.21-7.37 (m, 5H), 7.14-7.18 (d, 1H), 6.27-6.36 (t, 1H), 5.31-5.48 (m, 2H), 4.22-4.25 (m, 1H), 4.12-4.18 (t, 2H), 3.76-3.82 (d, 1H), 3.57-3.68 (m, 1H), 2.91-2.99 (t, 2H), 2.79-2.87 (t, 2H), 1.61-1.68 (t, 2H), 1.30-1.38 (t, 4H), 0.89-0.95 (t, 3H).

Example 57

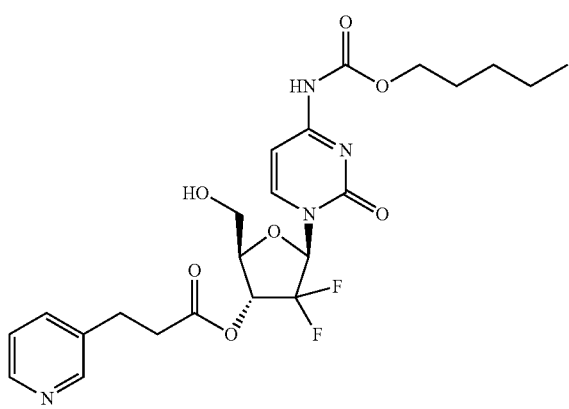

77

Preparation of 1-[(2R,4R,5R)-3,3-Difluoro-5-hydroxymethyl-4-(3-(3-pyridyl)propanoyloxy)oxolan-2-yl]-1,2-dihydro-4-(pentyloxycarbonylamino)-pyrimidin-2-one (77)

Using Method G and 3-(3-pyridyl)propanoic acid, 75 was converted to 77 (white solid, 51% yield): $^1$H NMR (200 MHz, DMSO-d$_6$) δ10.91 (s, 1H), 8.52 (s, 1H), 8.44-8.46 (d, 1H), 8.18-8.22 (d, 1H), 7.70-7.74 (d, 1H), 7.31-7.38 (m, 1H), 7.14-7.18 (d, 1H), 6.27-6.35 (t, 1H), 5.31-5.43 (m, 2H), 4.21-4.26 (m, 1H), 4.11-4.18 (t, 2H), 3.76-3.82 (d, 1H), 3.58-3.69 (m, 1H), 2.89-2.95 (t, 4H), 1.61-1.68 (t, 2H), 1.30-1.39 (t, 4H), 0.88-0.95 (t, 3H).

Example 58

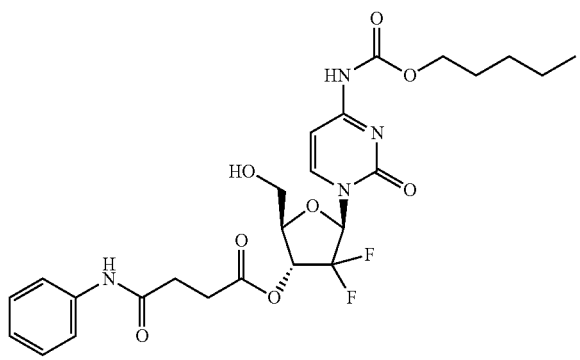

78

Preparation of 1-[(2R,4R,5R)-4-(4-Anilino-4-oxo-butanoyloxy)-3,3-difluoro-5-hydroxymethyl-oxolan-2-yl]-1,2-dihydro-4-(pentyloxycarbonylamino)-pyrimidin-2-one (78)

Using Method G and 4-anilino-4-oxo-butanoic acid, 75 was converted to 78 (white solid, 59% yield): $^1$H NMR (200 MHz, DMSO-d$_6$) δ10.90 (s, 1H), 10.06 (s, 1H), 8.20-8.24 (d, 1H), 7.59-7.62 (d, 2H), 7.28-7.36 (t, 2H), 7.14-7.18 (d, 1H), 7.02-7.10 (t, 1H), 6.29-6.37 (t, 1H), 5.32-5.51 (m, 2H), 4.25-4.29 (m, 1H), 4.11-4.18 (t, 2H), 3.80-3.95 (m, 1H), 3.69-3.72 (m, 1H), 2.77-2.79 (d, 2H), 2.71-2.73 (d, 2H), 1.61-1.68 (t, 2H), 1.31-1.37 (t, 4H), 0.88-0.95 (t, 3H).

Example 59

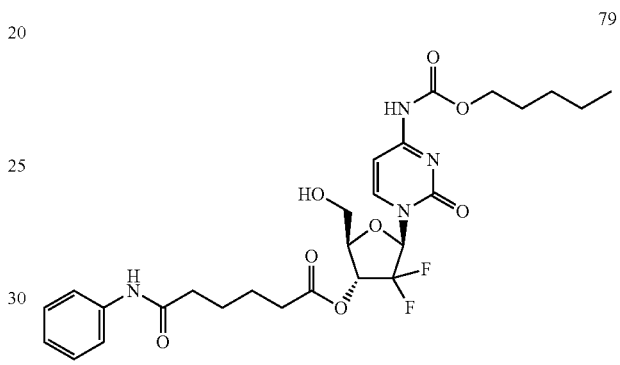

79

Preparation of 1-[(2R,4R,5R)-4-(6-Anilino-6-oxo-hexanoyloxy)-3,3-difluoro-5-hydroxymethyl-oxolan-2-yl]-1,2-dihydro-4-(pentyloxycarbonylamino)-pyrimidin-2-one (79)

Using Method G and 6-anilino-6-oxo-hexanoic acid, 75 was converted to 79 (white solid, 88% yield): $^1$H NMR (200 MHz, DMSO-d$_6$) δ10.91 (s, 1H), 9.91 (s, 1H), 8.20-8.23 (d, 1H), 7.60-7.64 (d, 2H), 7.28-7.36 (t, 2H), 7.15-7.19 (d, 1H), 7.01-7.09 (t, 1H), 6.28-6.37 (t, 1H), 5.32-5.49 (m, 2H), 4.26-4.29 (m, 1H), 4.12-4.18 (t, 2H), 3.79-3.87 (m, 1H), 3.70-3.75 (m, 1H), 2.54 (s, 2H), 2.37 (s, 2H), 1.66 (s, 6H), 1.32-1.37 (t, 4H), 0.88-0.95 (t, 3H).

Example 60

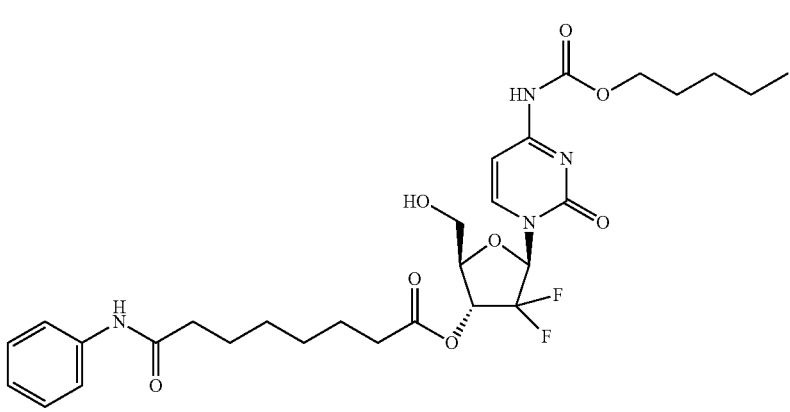

80

Preparation of 1-[(2R,4R,5R)-4-(8-Anilino-8-oxo-octanoyloxy)-3,3-difluoro-5-hydroxymethyl-oxolan-2-yl]-1,2-dihydro-4-(pentyloxycarbonylamino)-pyrimidin-2-one (80)

Using Method G and 8-anilino-8-oxo-octanoic acid, 75 was converted to 80 (white solid, 79% yield): $^1$H NMR (200 MHz, DMSO-$d_6$) δ10.92 (s, 1H), 9.88 (s, 1H), 8.19-8.23 (d, 1H), 7.60-7.64 (d, 2H), 7.27-7.35 (t, 2H), 7.14-7.18 (d, 1H), 7.01-7.08 (t, 1H), 6.28-6.36 (t, 1H), 5.35-5.49 (m, 2H), 4.25-4.29 (m, 1H), 4.11-4.18 (t, 2H), 3.65-3.85 (m, 2H), 2.46-2.53 (t, 2H), 2.29-2.36 (t, 2H), 1.66 (s, 6H), 1.31-1.35 (t, 8H), 0.88-0.95 (t, 3H).

Example 61

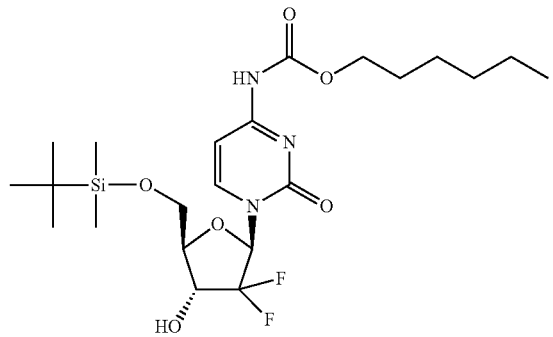

81

Preparation of 1-[(2R,4R,5R)-5-tert-Butyldimethyl-silyloxymethyl-3,3-difluoro-4-hydroxy-oxolan-2-yl]-1,2-dihydro-4-(hexyloxycarbonylamino)-pyrimidin-2-one (81)

Using Method F, 36 was converted to 81 (colorless oil, 70% yield): $^1$H NMR (400 MHz, DMSO-$d_6$) δ10.90 (s, 1H), 8.14-8.16 (d, 1H), 7.13-7.15 (d, 1H), 6.44-6.46 (d, 1H), 6.19-6.23 (t, 1H), 4.18-4.25 (m, 1H), 4.12-4.16 (t, 2H), 3.98-4.04 (m, 2H), 3.86-3.90 (m, 1H), 1.61-1.65 (t, 2H), 1.31-1.34 (d, 6H), 0.94 (s, 9H), 0.94 (t, 3H), 0.14 (s, 6H).

Preparation of 1-[(2R,4R,5R)-3,3-Difluoro-5-hydroxymethyl-4-(3-phenylpropanoyloxy)oxolan-2-yl]-1,2-dihydro-4-(hexyloxycarbonylamino)-pyrimidin-2-one (82)

Using Method G and 3-phenylpropanoic acid, 81 was converted to 82 (white solid, 92% yield): $^1$H NMR (400 MHz, DMSO-$d_6$) δ10.92 (s, 1H), 8.20-8.22 (d, 1H), 7.27-7.32 (m, 5H), 7.15-7.17 (d, 1H), 6.29-6.31 (t, 1H), 5.37-5.44 (m, 1H), 5.34 (s, 1H), 4.23-4.24 (t, 1H), 4.13-4.16 (t, 2H), 3.77-3.80 (d, 1H), 3.61-3.64 (d, 1H), 2.92-2.94 (d, 2H), 2.84-2.86 (d, 2H), 1.62-1.65 (t, 2H), 1.27-1.37 (d, 6H), 0.89-0.91 (t, 3H).

Example 62

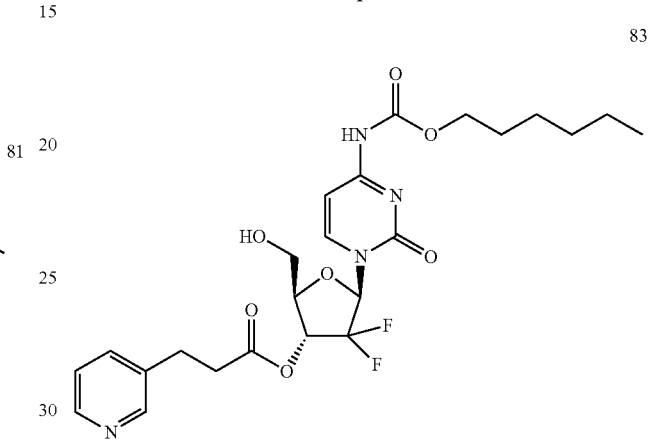

83

Preparation of 1-[(2R,4R,5R)-3,3-Difluoro-5-hydroxymethyl-4-(3-(3-pyridyl)propanoyloxy)oxolan-2-yl]-1,2-dihydro-4-(hexyloxycarbonylamino)-pyrimidin-2-one (83)

Using Method G and 3-(3-pyridyl)propanoic acid, 81 was converted to 83 (white solid, 46% yield): $^1$H NMR (400 MHz, DMSO-$d_6$) δ10.92 (s, 1H), 8.52 (s. 1H), 8.45-8.46 (d, 1H), 8.20-8.21 (d, 1H), 7.71-7.73 (d, 1H), 7.33-7.36 (t, 1H), 7.15-7.17 (d, 1H), 6.29-6.33 (t, 1H), 5.38-5.44 (m, 1H), 5.33-5.36 (t, 1H), 4.24-4.25 (t, 1H), 4.13-4.16 (t, 2H), 3.77-3.80 (d, 1H), 3.61-3.66 (d, 1H), 2.94-2.95 (d, 2H), 2.89-2.91 (d, 2H), 1.62-1.65 (t, 2H), 1.32-1.37 (d, 6H), 0.89-0.90 (t, 3H).

Example 63

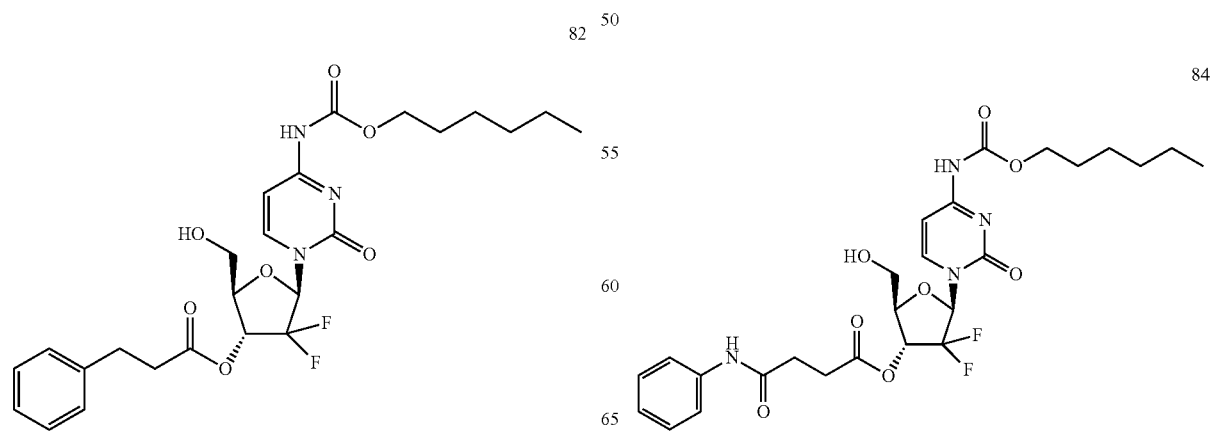

Preparation of 1-[(2R,4R,5R)-4-(4-Anilino-4-oxo-butanoyloxy)-3,3-difluoro-5-hydroxymethyl-oxolan-2-yl]-1,2-dihydro-4-(hexyloxycarbonylamino)-pyrimidin-2-one (84)

Using Method G and 4-anilino-4-oxo-butanoic acid, 81 was converted to 84 (white solid, 61% yield): $^1$H NMR (400 MHz, DMSO-d$_6$) δ10.91 (s, 1H), 10.06 (s, 1H), 8.21-8.23 (d, 1H), 7.60-7.61 (d, 2H), 7.30-7.34 (t, 2H), 7.15-7.17 (d, 1H), 7.04-7.08 (t, 1H), 6.31-6.35 (t, 1H), 5.40-5.47 (m, 1H), 5.34-5.37 (t, 1H), 4.26-4.29 (m, 1H), 4.13-4.16 (t, 2H), 3.80-3.83 (d, 1H), 3.66-3.72 (m, 1H), 2.78-2.82 (t, 2H), 2.69-2.72 (t, 2H), 1.60-1.67 (m, 2H), 1.31-1.39 (m, 6H), 0.89-0.92 (t, 3H).

Example 64

Preparation of 1-[(2R,4R,5R)-4-(8-Anilino-8-oxo-octanoyloxy)-3,3-difluoro-5-hydroxymethyl-oxolan-2-yl]-1,2-dihydro-4-(hexyloxycarbonylamino)-pyrimidin-2-one (86)

Using Method G and 8-anilino-8-oxo-octanoic acid, 81 was converted to 86 (white solid, 57% yield): $^1$H NMR (400 MHz, DMSO-d$_6$) δ10.92 (s, 1H), 9.98 (s, 1H), 8.21-8.22 (d, 1H), 7.61-7.63 (d, 2H), 7.29-7.33 (t, 2H), 7.16-7.18 (d, 1H), 7.03-7.06 (t, 1H), 6.30-6.34 (t, 1H), 5.39-5.46 (m, 1H), 5.34-5.37 (t, 1H), 4.26-4.28 (t, 1H), 4.13-4.16 (t, 2H), 3.80-3.84 (d, 1H), 3.66-3.71 (m, 1H), 2.48-2.51 (t, 2H), 2.31-2.35 (t, 2H), 1.60-1.65 (m, 6H), 1.31-1.36 (m, 10H), 0.89-0.92 (t, 3H).

Example 66

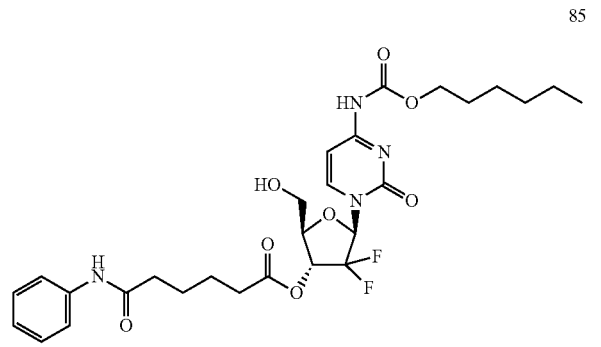 [SMILES: CCCCCCOC(=O)Nc1ccn([C@@H]2O[C@H](CO)[C@@H](OC(=O)CCCCC(=O)Nc3ccccc3)C2(F)F)c(=O)n1]

Preparation of 1-[(2R,4R,5R)-4-(6-Anilino-6-oxo-hexanoyloxy)-3,3-difluoro-5-hydroxymethyl-oxolan-2-yl]-1,2-dihydro-4-(hexyloxycarbonylamino)-pyrimidin-2-one (85)

Using Method G and 6-anilino-6-oxo-hexanoic acid, 81 was converted to 85 (white solid, 80% yield): $^1$H NMR (400 MHz, DMSO-d$_6$) δ10.91 (s, 1H), 9.92 (s, 1H), 8.21-8.23 (d, 1H), 7.61-7.63 (d, 2H), 7.30-7.34 (t, 2H), 7.16-7.18 (d, 1H), 7.03-7.07 (t, 1H), 6.30-6.35 (t, 1H), 5.39-5.46 (m, 1H), 5.34-5.37 (t, 1H), 4.28-4.29 (t, 1H), 4.13-4.16 (t, 2H), 3.81-3.84 (d, 1H), 3.67-3.72 (m, 1H), 2.54 (s, 2H), 2.37 (s, 2H), 1.65 (s, 6H), 1.32 (s, 6H), 0.89-0.91 (t, 3H).

Example 65

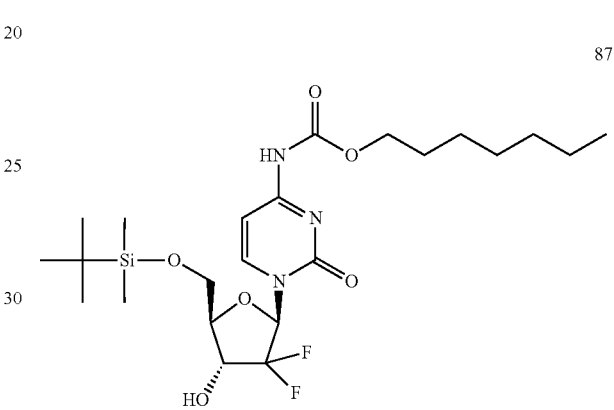

Preparation of 1-[(2R,4R,5R)-5-tert-Butyldimethyl-silyloxymethyl-3,3-difluoro-4-hydroxy-oxolan-2-yl]-1,2-dihydro-4-(heptyloxycarbonylamino)-pyrimidin-2-one (87)

Using Method F, 43 was converted to 87 (white solid, 70% yield): $^1$H NMR (200 MHz, DMSO-d$_6$) δ10.91 (s, 1H), 8.13-8.16 (d, 1H), 7.12-7.16 (d, 1H), 6.42-6.44 (d, 1H), 6.18-6.25 (t, 1H), 4.11-4.23 (m, 3H), 3.86-4.08 (m, 3H), 1.60-1.67 (t, 2H), 1.31 (s, 8H), 0.94 (s, 9H), 0.94 (t, 3H), 0.14 (s, 6H).

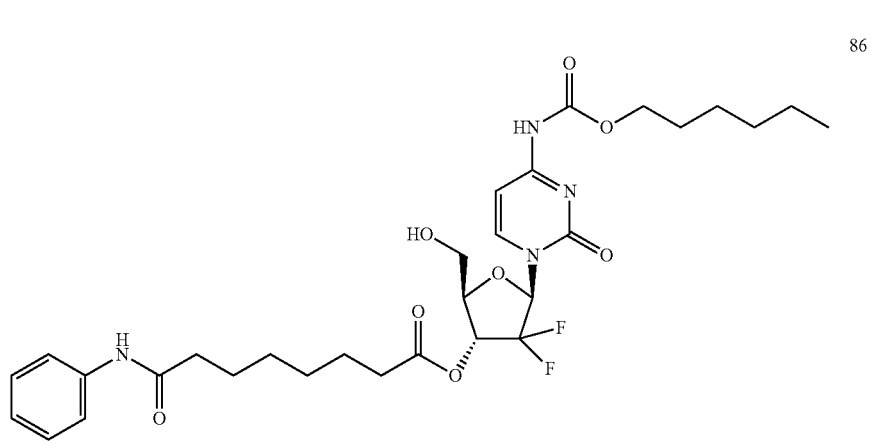 [SMILES: CCCCCCOC(=O)Nc1ccn([C@@H]2O[C@H](CO)[C@@H](OC(=O)CCCCCCC(=O)Nc3ccccc3)C2(F)F)c(=O)n1]

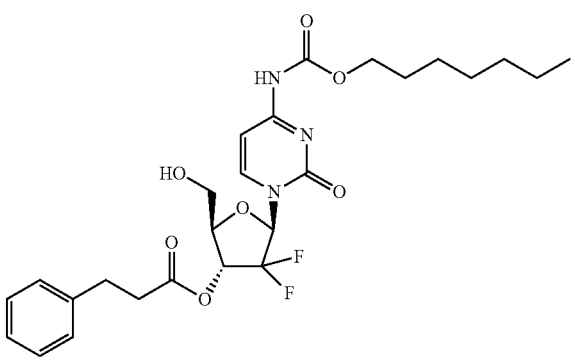

88

Preparation of 1-[(2R,4R,5R)-3,3-Difluoro-5-hydroxymethyl-4-(3-phenyl-propanoyloxy)oxolan-2-yl]-1,2-dihydro-4-(heptyloxycarbonylamino)-pyrimidin-2-one (88)

Using Method G and 3-phenylpropanoic acid, 87 was converted to 88 (white solid, 57% yield): $^1$H NMR (200 MHz, DMSO-$d_6$) δ10.92 (s, 1H), 8.19-8.23 (d, 1H), 7.27-7.32 (m, 5H), 7.14-7.18 (d, 1H), 6.27-6.36 (t, 1H), 5.25-5.48 (m, 2H), 4.22-4.27 (m, 1H), 4.11-4.18 (t, 2H), 3.76-3.82 (d, 1H), 3.57-3.68 (m, 1H), 2.91-2.97 (t, 2H), 2.80-2.87 (t, 2H), 1.61-1.67 (t, 2H), 1.27-1.37 (t, 8H), 0.87-0.93 (t, 3H).

Example 67

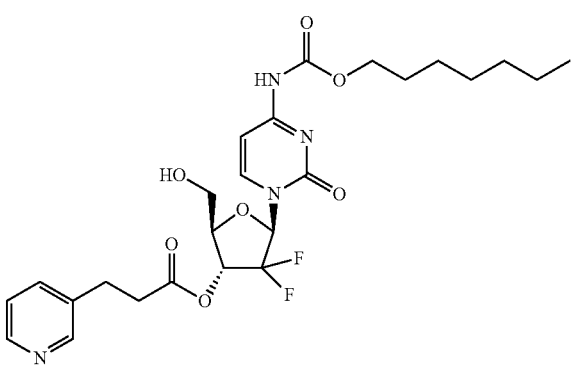

89

Preparation of 1-[(2R,4R,5R)-3,3-Difluoro-5-hydroxymethyl-4-(3-(3-pyridyl)propanoyloxy)oxolan-2-yl]-1,2-dihydro-4-(heptyloxycarbonylamino)-pyrimidin-2-one (89)

Using Method G and 3-(3-pyridyl)propanoic acid, 87 was converted to 89 (white solid, 76% yield): $^1$H NMR (200 MHz, DMSO-$d_6$) δ10.92 (s, 1H), 8.51-8.52 (d, 1H), 8.43-8.47 (m, 1H), 8.18-8.21 (d, 1H), 7.70-7.75 (m, 1H), 7.31-7.38 (m, 1H), 7.14-7.18 (d, 1H), 6.27-6.35 (t, 1H), 5.31-5.48 (m, 2H), 4.23-4.26 (m, 1H), 4.11-4.18 (t, 2H), 3.76-3.82 (d, 1H), 3.58-3.69 (m, 1H), 2.89-2.95 (t, 4H), 1.61-1.67 (t, 2H), 1.30-1.31 (t, 8H), 0.87-0.93 (t, 3H).

Example 68

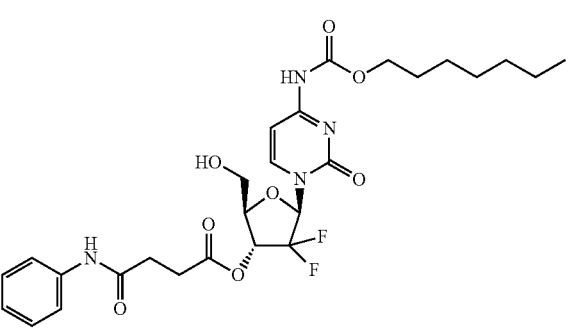

90

Preparation of 1-[(2R,4R,5R)-4-(4-Anilino-4-oxobutanoyloxy)-3,3-difluoro-5-hydroxymethyl-oxolan-2-yl]-1,2-dihydro-4-(heptyloxycarbonylamino)-pyrimidin-2-one (90)

Using Method G and 4-anilino-4-oxo-butanoic acid 87 was converted to 90 (white solid, 47% yield): $^1$H NMR (200 MHz, DMSO-$d_6$) δ10.91 (s, 1H), 10.05 (s, 1H), 8.20-8.24 (d, 1H), 7.59-7.62 (d, 2H), 7.28-7.36 (t, 2H), 7.14-7.18 (d, 1H), 7.02-7.09 (t, 1H), 6.29-6.37 (t, 1H), 5.36-5.51 (m, 2H), 4.25-4.29 (m, 1H), 4.11-4.18 (t, 2H), 3.79-3.86 (d, 1H), 3.64-3.72 (d, 1H), 2.77-2.82 (t, 2H), 2.69-2.73 (t, 2H), 1.60-1.67 (t, 2H), 1.30-1.31 (d, 8H), 0.86-0.93 (t, 3H).

Example 69

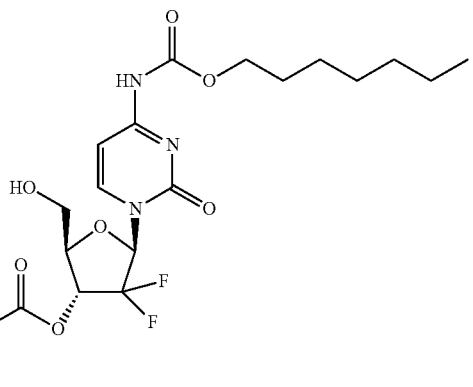

91

Preparation of 1-[(2R,4R,5R)-4-(6-Anilino-6-oxo-hexanoyloxy)-3,3-difluoro-5-hydroxymethyl-oxolan-2-yl]-1,2-dihydro-4-(heptyloxycarbonylamino)-pyrimidin-2-one (91)

Using Method G and 6-anilino-6-oxo-hexanoic acid, 87 was converted to 91 (white solid, 77% yield): $^1$H NMR (200 MHz, DMSO-d$_6$) δ10.91 (s, 1H), 9.91 (s, 1H), 8.20-8.23 (d, 1H), 7.60-7.64 (d, 2H), 7.28-7.36 (t, 2H), 7.15-7.19 (d, 1H), 7.01-7.09 (t, 1H), 6.28-6.37 (t, 1H), 5.35-5.49 (m, 2H), 4.26-4.29 (m, 1H), 4.11-4.18 (t, 2H), 3.66-3.94 (m, 2H), 2.54 (s, 2H), 2.37 (s, 2H), 1.66 (s, 6H), 1.32 (s, 8H), 0.87-0.93 (t, 3H).

Example 70

Preparation of 1-[(2R,4R,5R)-5-tert-Butyldimethyl-silyloxymethyl-3,3-difluoro-4-hydroxy-oxolan-2-yl]-1,2-dihydro-4-(2-methoxyethyloxycarbonyl-amino) pyrimidin-2-one (93)

Using Method F, 50 was converted to 93 (colorless solid, 82% yield): $^1$H NMR (500 MHz, DMSO-d$_6$) δ10.97 (s, 1H), 8.14-8.16 (d, 1H), 7.12-7.14 (d, 1H), 6.42-6.44 (d, 1H), 6.20-6.23 (t, 1H), 4.28-4.30 (t, 2H), 4.19-4.21 (m, 1H), 3.98-4.02 (m, 2H), 3.87-3.90 (m, 1H), 3.58-3.60 (t, 2H), 3.31 (s, 3H), 0.94 (s, 9H), 0.14 (s, 6H).

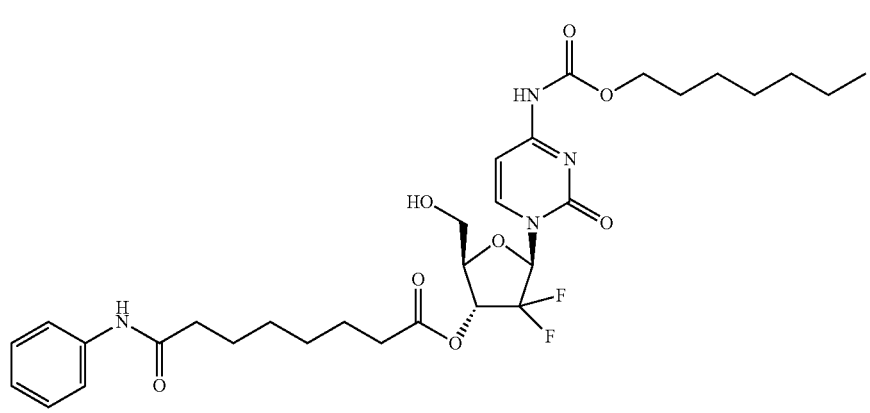

92

Preparation of 1-[(2R,4R,5R)-4-(8-Anilino-8-oxo-octanoyloxy)-3,3-difluoro-5-hydroxymethyl-oxolan-2-yl]-1,2-dihydro-4-(heptyloxycarbonylamino)-pyrimidin-2-one (92)

Using Method G and 8-anilino-8-oxo-octanoic acid, 87 was converted to 92 (white solid, 36% yield): $^1$H NMR (200 MHz, DMSO-d$_6$) δ10.91 (s, 1H), 9.88 (s, 1H), 8.19-8.23 (d, 1H), 7.60-7.64 (d, 2H), 7.27-7.35 (t, 2H), 7.15-7.18 (d, 1H), 7.01-7.09 (t, 1H), 6.28-6.36 (t, 1H), 5.35-5.49 (m, 2H), 4.25-4.29 (m, 1H), 4.11-4.18 (t, 2H), 3.64-3.85 (m, 2H), 2.46-2.52 (t, 2H), 2.29-2.36 (t, 2H), 1.58-1.64 (t, 6H), 1.30-1.35 (t, 12H), 0.86-0.93 (t, 3H).

Example 71

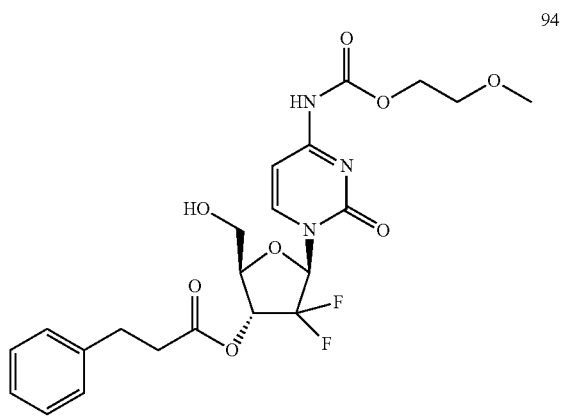 [SMILES: COCCOC(=O)Nc1ccn([C@@H]2O[C@H](CO)[C@@H](OC(=O)CCc3ccccc3)C2(F)F)c(=O)n1]

94

Preparation of 1-[(2R,4R,5R)-3,3-Difluoro-5-hydroxymethyl-4-(3-phenylpropanoyloxy)oxolan-2-yl]-1,2-dihydro-4-(2-methoxyethyloxycarbonyl-amino)pyrimidin-2-one (94)

Using Method G and 3-phenylpropanoic acid, 93 was converted to 94 (white solid, 66% yield): $^1$H NMR (500 MHz, DMSO-d$_6$) δ10.97 (s, 1H), 8.20-8.22 (d, 1H), 7.22-7.34 (m, 5H), 7.14-7.16 (d, 1H), 6.30-6.33 (t, 1H), 5.38-5.41 (m, 1H), 5.33 (s, 1H), 4.28-4.30 (t, 2H), 4.23-4.24 (m, 1H), 3.77-3.79 (d, 1H), 3.64 (s, 1H), 3.59-3.61 (t, 2H), 3.31 (s, 3H), 2.93-2.95 (t, 2H), 2.82-2.85 (t, 2H).

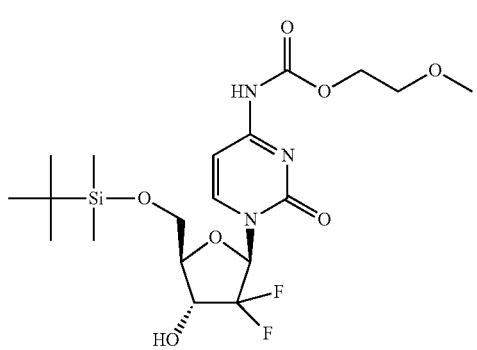

93

Example 72

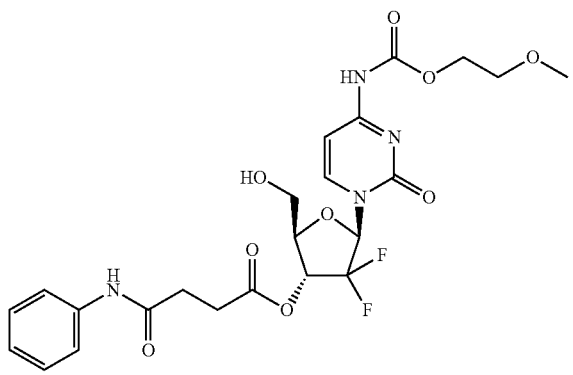

95

Preparation of 1-[(2R,4R,5R)-4-(4-Anilino-4-oxo-butanoyloxy)-3,3-difluoro-5-hydroxymethyl-oxolan-2-yl]-1,2-dihydro-4-(2-methoxyethyloxy-carbonylamino)pyrimidin-2-one (95)

Using Method G and 4-anilino-4-oxo-butanoic acid, 93 was converted to 95 (white solid, 88% yield): $^1$H NMR (400 MHz, DMSO-d$_6$) δ 10.95 (s, 1H), 10.01 (s, 1H), 8.31-8.33 (d, 1H), 7.60-7.62 (d, 2H), 7.28-7.36 (t, 2H), 7.11-7.13 (d, 1H), 7.03-7.07 (t, 1H), 6.38-6.39 (d, 1H), 5.36-5.38 (t, 2H), 4.27-4.30 (m, 2H), 4.8-4.25 (m, 1H), 3.82-3.86 (d, 1H), 3.67-3.71 (d, 1H), 3.58-3.60 (m, 2H), 3.31 (s, 3H), 2.61-2.67 (m, 4H).

Example 73

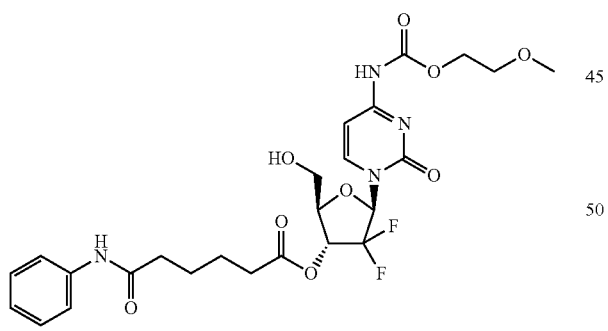

96

Preparation of 1-[(2R,4R,5R)-4-(6-Anilino-6-oxo-hexanoyloxy)-3,3-difluoro-5-hydroxymethyl-oxolan-2-yl]-1,2-dihydro-4-(2-methoxyethyloxy-carbonylamino)pyrimidin-2-one (96)

Using Method G and 6-anilino-6-oxo-hexanoic acid, 93 was converted to 96 (white solid, 91% yield): $^1$H NMR (400 MHz, DMSO-d$_6$) δ 10.97 (s, 1H), 9.93 (s, 1H), 8.21-8.23 (d, 1H), 7.61-7.62 (d, 2H), 7.30-7.34 (t, 2H), 7.15-7.17 (d, 1H), 7.03-7.07 (t, 1H), 6.30-6.34 (t, 1H), 5.36-5.45 (m, 2H), 4.27-4.30 (m, 3H), 3.80-3.84 (m, 1H), 3.66-3.71 (m, 1H), 3.58-3.61 (m, 2H), 3.31 (s, 3H), 2.53-2.55 (t, 2H), 2.35-2.38 (t, 2H), 1.64-1.66 (t, 4H).

Example 74

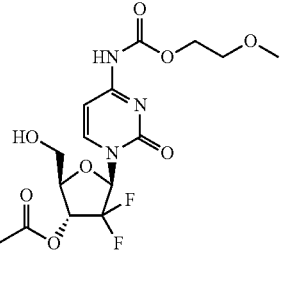

97

Preparation of 1-[(2R,4R,5R)-4-(8-Anilino-8-oxo-octanoyloxy)-3,3-difluoro-5-hydroxymethyl-oxolan-2-yl]-1,2-dihydro-4-(2-methoxyethyloxy-carbonylamino)pyrimidin-2-one (97)

Using Method G and 8-anilino-8-oxo-octanoic acid, 93 was converted to 97 (white solid, 97% yield): $^1$H NMR (500 MHz, DMSO-d$_6$) δ 10.96 (s, 1H), 9.88 (s, 1H), 8.21-8.22 (d, 1H), 7.61-7.62 (d, 2H), 7.30-7.33 (t, 2H), 7.15-7.16 (d, 1H), 7.03-7.06 (t, 1H), 6.30-6.33 (t, 1H), 5.39-5.43 (m, 2H), 4.27-4.30 (t, 3H), 3.80-3.83 (d, 1H), 3.68-3.69 (d, 1H), 3.59-3.61 (t, 2H), 3.31 (s, 3H), 2.48-2.51 (t, 2H), 2.31-2.34 (t, 2H), 1.60-1.63 (t, 4H), 1.35 (s, 4H).

Example 75

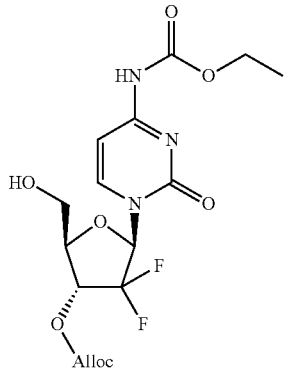

98

Preparation of 1-[(2R,4R,5R)-4-Allyloxycarbonyloxy-3,3-difluoro-5-(hydroxymethyl)oxolan-2-yl]-1,2-dihydro-4-(ethoxycarbonylamino)-pyrimidin-2-one (98)

Using Method B and allyl chloroformate, 8 was converted to 98 (white solid, 54% yield): $^1$H NMR (400 MHz, DMSO-d$_6$) δ10.91 (s, 1H), 8.18-8.20 (d, 1H), 7.16-7.19 (d, 1H), 6.31-6.36 (t, 1H), 5.96-6.03 (m, 1H), 5.31-5.39 (m, 3H), 5.43 (s, 1H), 4.73-4.76 (t, 2H), 4.30-4.33 (dd, 1H), 4.17-4.23 (dd, 2H), 3.81-3.87 (m, 1H), 3.70-3.76 (m, 1H), 1.26-1.29 (t, 3H); MS (HR-ESI): m/z 442.1035 [M+Na]⁺.

Example 76

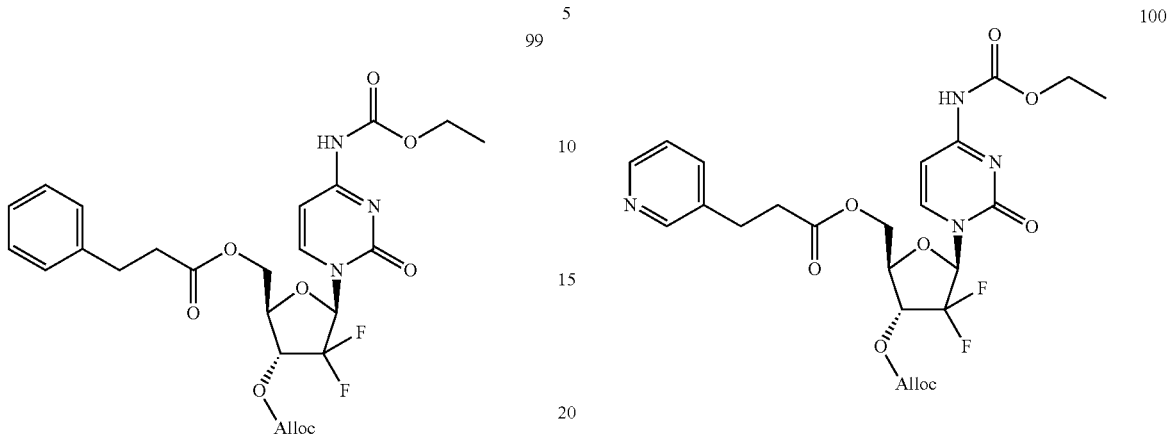

Preparation of 1-[(2R,4R,5R)-4-Allyloxycarbony-loxy-3,3-difluoro-5-(3-phenylpropanoyloxymethyl)oxolan-2-yl]-1,2-dihydro-4-(ethoxycarbonylamino)-pyrimidin-2-one (99)

Using Method C and 3-phenylpropanoic acid, 98 was converted to 99 (colorless oil, 54% yield): ¹H NMR (400 MHz, DMSO-d₆) δ10.94 (s, 1H), 8.05-8.07 (d, 1H), 7.17-7.33 (m, 6H), 6.34 (t, 1H), 5.95-6.00 (m, 1H), 5.38-5.43 (d, 2H), 5.30-5.34 (d, 1H), 4.72-4.75 (t, 2H), 4.47-4.51 (d, 2H), 4.41-4.44 (m, 1H), 4.18-4.23 (dd, 2H), 2.87-2.92 (t, 2H), 2.70-2.75 (t, 2H), 1.25-1.29 (t, 3H); MS (HR-ESI): m/z 550.1629 [M−H]⁻.

Preparation 1-[(2R,4R,5R)-4-Allyloxycarbonyloxy-3,3-difluoro-5-(3-(3-pyridyl)-propanoyloxymethyl)oxolan-2-yl]-1,2-dihydro-4-(ethoxycarbonylamino)-pyrimidin-2-one (100)

Using Method C and 3-(3-pyridyl) acid, 98 was converted to 100 (colorless oil, 63% yield): ¹H NMR (400 MHz, DMSO-d₆) δ10.94 (s, 1H), 8.49-8.50 (d, 1H), 8.42-8.44 (d, 1H), 8.05-8.07 (d, 1H), 7.69-7.71 (d, 1H), 7.31-7.34 (m, 1H), 7.17-7.19 (d, 1H), 6.34 (t, 1H), 5.95-6.02 (m, 1H), 5.38-5.43 (dd, 2H), 5.30-5.34 (d, 1H), 4.73-4.74 (d, 2H), 4.49-4.53 (m, 2H), 4.40-4.48 (m, 1H), 4.20-4.22 (m, 2H), 2.89-2.93 (t, 2H), 2.75-2.79 (t, 2H), 1.25-1.29 (t, 3H).

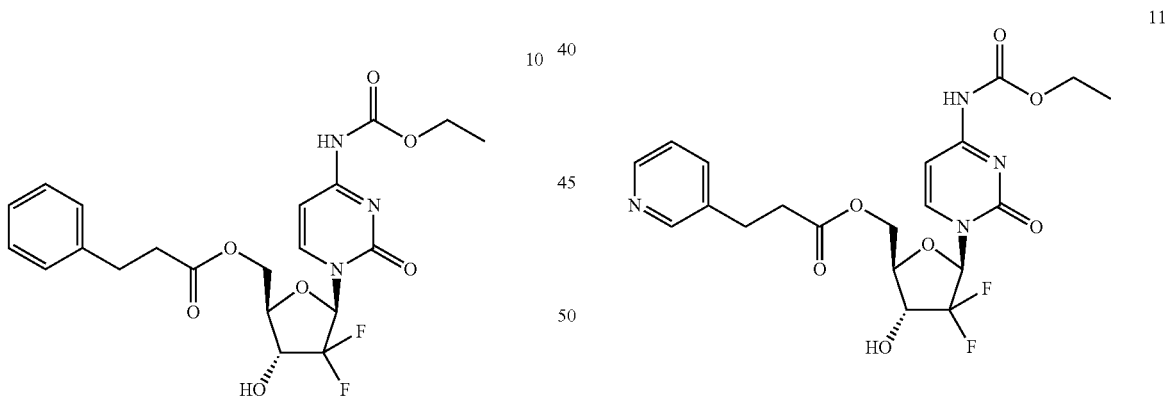

Preparation of 1-[(2R,4R,5R)-3,3-Difluoro-4-hydroxy-5-(3-phenylpropanoyloxymethyl)oxolan-2-yl]-1,2-dihydro-4-(ethoxycarbonylamino)-pyrimidin-2-one (10)

Using method C, 99 was converted to 10 (colorless solid, 98% yield): ¹H NMR (400 MHz, DMSO-d₆) δ10.89 (s, 1H), 7.99-8.02 (d, 1H), 7.15-7.33 (m, 6H), 6.49-6.52 (d, 1H), 6.21-6.26 (t, 1H), 4.34-4.46 (m, 2H), 4.17-4.28 (m, 3H), 4.04-4.13 (m, 1H), 2.88-2.93 (t, 2H), 2.74-2.77 (t, 2H), 1.26-1.29 (t, 3H); MS (HR-ESI): m/z 490.1405 [M+H]⁺.

Preparation of 1-[(2R,4R,5R)-3,3-Difluoro-4-hydroxy-5-(3-(3-pyridyl)-propanoyloxymethyl)oxolan-2-yl]-1,2-dihydro-4-(ethoxycarbonylamino)-pyrimidin-2-one (11)

Using Method C, 100 was converted to 11 (yellow solid, 73% yield): ¹H NMR (400 MHz, DMSO-d₆) δ10.89 (s, 1H), 8.50 (s, 1H), 8.42-8.45 (dd, 1H), 7.99-8.02 (d, 1H), 7.69-7.72 (d, 1H), 7.31-7.35 (m, 1H), 7.15-7.18 (d, 1H), 6.50-6.52 (d, 1H), 6.21-6.26 (t, 1H), 4.34-4.46 (m, 2H), 4.17-4.24 (m, 3H), 4.04-4.12 (m, 1H), 2.90-2.95 (t, 2H), 2.78-2.82 (t, 2H), 1.25-1.29 (t, 3H); MS (FAB): m/z 469.1528 [M+H]⁺

Example 77

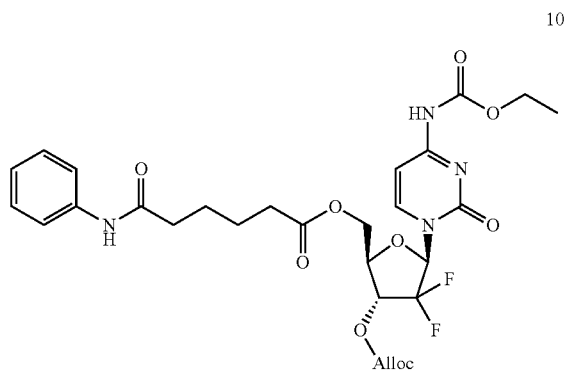

Preparation of 1-[(2R,4R,5R)-4-Allyloxycarbonyloxy-5-(((6-anilino-oxo-hexanoyloxy)methyl)-3,3-difluoro-oxolan-2-yl]-1,2-dihydro-4-(ethoxycarbonylamino)-pyrimidin-2-one (101)

Using Method C and 6-anilino-6-oxo-hexanoic acid, 98 was converted to 101 (colorless oil, 84% yield): $^1$H NMR (400 MHz, DMSO-$d_6$) δ10.94 (s, 1H), 9.89 (s, 1H), 8.07-8.10 (d, 1H), 7.59-7.62 (d, 2H), 7.28-7.33 (t, 2H), 7.18-7.20 (d, 1H), 7.02-7.07 (t, 1H), 6.33-6.38 (t, 1H), 5.94-6.04 (m, 1H), 5.31-5.43 (m, 3H), 4.72-4.75 (m, 2H), 4.49-4.53 (d, 2H), 4.40-4.45 (m, 1H), 4.19-4.21 (dd, 2H), 2.42-2.45 (t, 2H), 2.32-2.36 (t, 2H), 1.62 (s, 4H), 1.27-1.29 (t, 3H).

Example 78

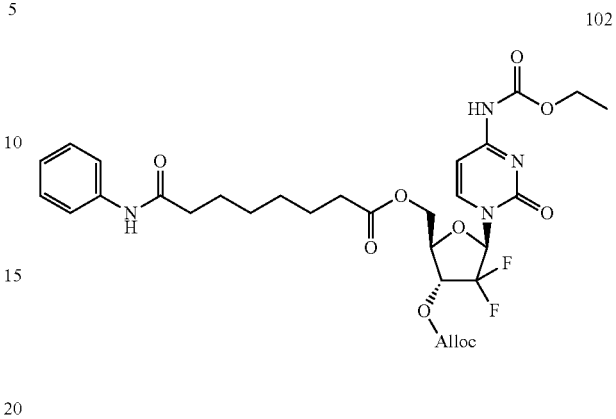

Preparation of 1-[(2R,4R,5R)-4-Allyloxycarbonyloxy-5-((8-anilino-8-oxo-octanoyloxy)methyl)-3,3-difluoro-oxolan-2-yl]-1,2-dihydro-4-(ethoxycarbonylamino)-pyrimidin-2-one (102)

Using Method C and 8-anilino-8-oxo-octanoic acid, 98 was converted to 102 (colorless oil, 34% yield): $^1$H NMR (400 MHz, DMSO-$d_6$) δ10.84 (s, 1H), 9.86 (s, 1H), 8.07-8.10 (d, 1H), 7.60-7.63 (d, 2H), 7.28-7.32 (t, 2H), 7.18-7.20 (d, 1H), 7.02-7.06 (t, 1H), 6.34-6.36 (m, 1H), 5.95-6.03 (m, 1H), 5.31-5.43 (m, 3H), 4.73 (s, 2H), 4.49-4.52 (d, 2H), 4.41-4.45 (m, 1H), 4.17-4.22 (dd, 2H), 2.37-2.41 (t, 2H), 2.30-2.34 (t, 2H), 1.55-1.63 (dd, 4H), 1.34 (s, 4H), 1.24-1.28 (t, 3H).

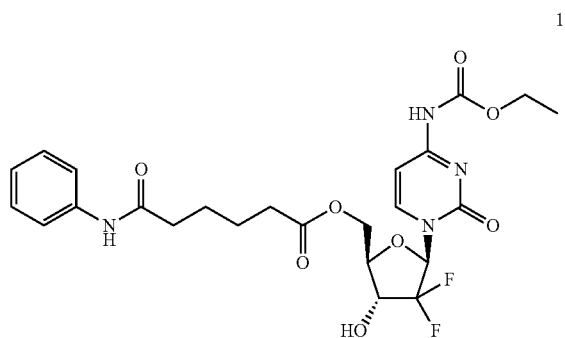

Preparation of 1-[(2R,4R,5R)-5-((6-Anilino-6-oxo-hexanoyloxy)methyl)-3,3-difluoro-4-hydroxy-oxolan-2-yl]-1,2-dihydro-4-(ethoxycarbonylamino)-pyrimidin-2-one (13)

Using Method C, 101 was converted to 13 (white solid, 56% yield): $^1$H NMR (400 MHz, DMSO-$d_6$) δ10.88 (s, 1H), 9.88 (s, 1H), 8.02-8.05 (d, 1H), 7.59-7.65 (d, 2H), 7.29-7.35 (t, 2H), 7.16-7.19 (d, 1H), 7.03-7.07 (t, 1H), 6.50-6.53 (d, 1H), 6.23-6.26 (t, 1H), 4.35-4.47 (m, 2H), 4.18-4.35 (m, 3H), 4.05-4.08 (d, 1H), 2.44-2.46 (t, 2H), 2.34-2.36 (t, 2H), 1.63 (s, 4H), 1.24-1.28 (t, 3H); MS (HR-ESI): m/z 561.1762 [M+Na]$^+$.

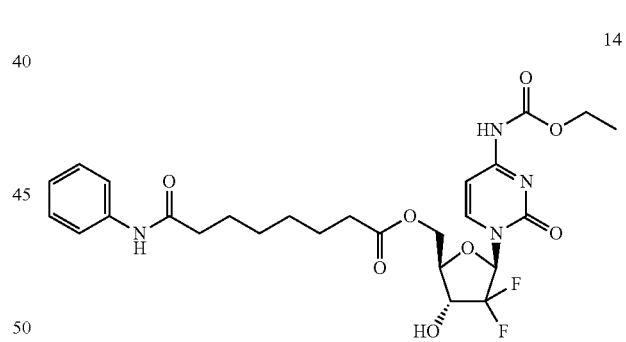

Preparation of 1-[(2R,4R,5R)-5-((8-Anilino-8-oxo-octanoyloxy)methyl)-3,3-difluoro-4-hydroxy-oxolan-2-yl]-1,2-dihydro-4-(ethoxycarbonylamino)-pyrimidin-2-one (14)

Using Method C, 102 was converted to 14 (white solid, 66% yield): $^1$H NMR (400 MHz, DMSO-$d_6$) δ10.88 (s, 1H), 9.85 (s, 1H), 8.02-8.04 (d, 1H), 7.60-7.63 (d, 2H), 7.28-7.33 (t, 2H), 7.16-7.19 (d, 1H), 7.02-7.07 (t, 1H), 6.50-6.53 (d, 1H), 6.22-6.27 (t, 1H), 4.34-4.47 (m, 2H), 4.11-4.30 (m, 4H), 2.39-2.44 (t, 2H), 2.30-2.34 (t, 2H), 1.57-1.64 (m, 4H), 1.33-1.36 (t, 4H), 1.24-1.28 (t, 3H); MS (HR-ESI): m/z 565.2112 [M−H]$^-$.

Example 79

Method H: In Vitro Metabolic Conversion Assay Using Human Liver S9 Fractions

A representative sampling of prodrug compounds was incubated with human liver S9 fractions (Life Technologies Corporation) at 10 µM in duplicates. Incubations were carried out at 37° C. in a shaker water bath. Samples were taken at 0 and 60 minutes. Negative controls (without S9 fractions) and positive controls (7-ethoxycoumarin and 7-hydroxycoumarin) were run concurrently with the test articles in duplicates. All samples were analyzed using LC/MS/MS; depletion of the parent compounds and the formation of gemcitabine were monitored, though the latter was not quantitatively monitored. The test results are tabulated in Table 1.

TABLE 1

| Test Sample | Compound | % of Parent Remaining | Formation of Gemcitabine |
|---|---|---|---|
| 1 | 3 | 1% | ✓ |
| 2 | 6 | 8% | ✓ |
| 3 | 10 | 0% | ✓ |
| 4 | 11 | 0% | ✓ |
| 5 | 13 | 13% | ✓ |
| 6 | 14 | 0% | ✓ |
| 7 | 58 | 0% | ✓ |
| 8 | 59 | 1% | ✓ |
| 9 | 62 | 2% | ✓ |

After incubation with human liver S9 fractions for 60 minutes, depletion of each test compound was observed along with formation of gemcitabine as a metabolite.

Example 80

Method I: Efficacy Evaluation in HCT116 Tumor Cell Xenograft Model in Nude Mice

Compounds 17, 18, 19 and 32 were evaluated for oral activity against human HCT116 colorectal adenocarcinoma in female nude mice. For the treatment groups, the above compounds were given perorally in 15% Tween 80 at a dose of 20 mg/kg once daily for 14 days. As a reference group, gemcitabine was administered intraperitoneally at 160 mg/kg once every three days for 4 doses. A control group received only the vehicle on the same peroral schedule as that of the treatment groups. Treatment began on Day 1 in all groups of female nude mice (n=8) bearing subcutaneous tumors of ~180 mm³ in size; the study duration was 14 days. Treatment results were presented as Tumor Growth Inhibition (TGI) as a percentage of average tumor size of untreated mice in the control group at Day 14. Compounds 17, 18, 19 and 32 showed TGI's of 77.3%, 81.1%, 75.8% and 86.7% respectively, as compared to a TGI of 85.6% for gemcitabine as a reference.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound having the formula:

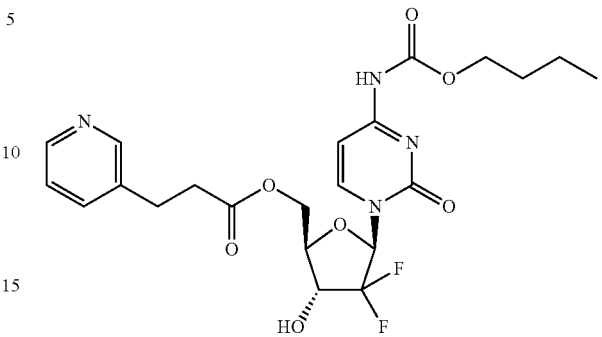

or a pharmaceutically acceptable salt thereof.

2. A pharmaceutical composition comprising a compound having the formula:

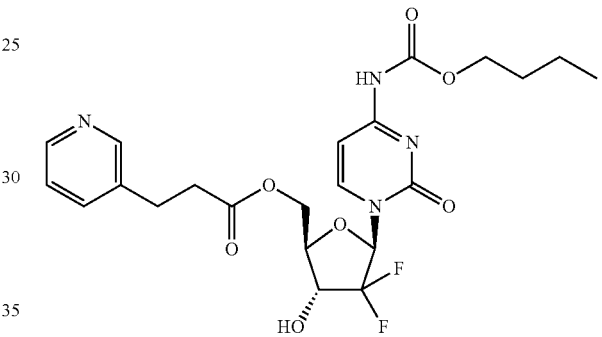

or a pharmaceutically acceptable salt thereof; and a pharmaceutically acceptable carrier.

3. A method for treating a cancer selected from the group consisting of pancreatic cancer, non-small cell lung cancer, breast cancer, ovarian cancer, bladder cancer, colorectal cancer, bile duct cancer, cervical cancer, gall bladder cancer and lymphoma by inhibiting the growth of cancer cells, the method comprising administering to a subject an effective amount of a pharmaceutical composition comprising: a compound having the formula:

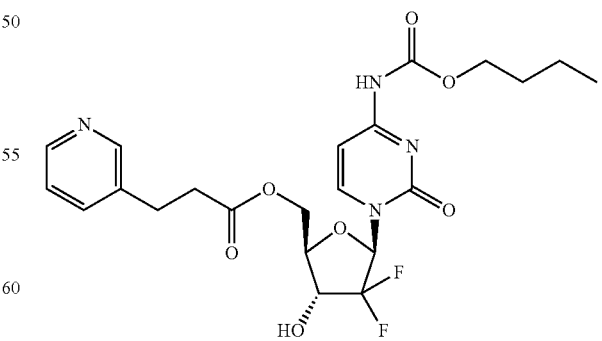

or a pharmaceutically acceptable salt thereof; and
a pharmaceutically acceptable carrier, thereby treating a cancer selected from the group consisting of pancreatic cancer, non-small cell lung cancer, breast cancer, ovarian cancer, bladder cancer, colorectal cancer, bile duct cancer, cervical cancer, gall bladder cancer and lymphoma.

4. The method according to claim 3, further comprising administering to the subject an anti-cancer agent.

5. The method according to claim 4, wherein the anti-cancer agent is selected from the group consisting of a conventional chemotherapeutic agent, a targeted therapeutic agent, a radiotherapeutic agent and a mixture thereof.

6. The method according to claim 4, wherein the anti-cancer agent is selected from the group consisting of cisplatin, oxaliplatin, carboplatin, erlotinib, gefitinib, lapatinib, cetuximab, zalutumumab, minotuzumab, matuzumab, capecitabine, docetaxel, and paclitaxel.

7. The method according to claim 3, wherein administering the composition is conducted orally.

8. The method according to claim 3, wherein administering the composition is conducted parenterally.

\* \* \* \* \*